(12) United States Patent
Nagase et al.

(10) Patent No.: US 7,090,689 B2
(45) Date of Patent: *Aug. 15, 2006

(54) SURGICAL INSTRUMENT

(75) Inventors: Toru Nagase, Tachikawa (JP); Katsumi Sasaki, Tokyo (JP)

(73) Assignee: Olympus Corporation (JP)

( * ) Notice: Subject to any disclaimer, the term of this patent is extended or adjusted under 35 U.S.C. 154(b) by 296 days.

This patent is subject to a terminal disclaimer.

(21) Appl. No.: 10/125,129

(22) Filed: Apr. 17, 2002

(65) Prior Publication Data

US 2002/0156497 A1 Oct. 24, 2002

(30) Foreign Application Priority Data

| Apr. 18, 2001 | (JP) | 2001-119901 |
| Apr. 18, 2001 | (JP) | 2001-119902 |
| Apr. 18, 2001 | (JP) | 2001-119903 |
| Apr. 18, 2001 | (JP) | 2001-119904 |
| Apr. 18, 2001 | (JP) | 2001-119905 |
| Nov. 15, 2001 | (JP) | 2001-350765 |
| Nov. 15, 2001 | (JP) | 2001-350766 |
| Nov. 15, 2001 | (JP) | 2001-350767 |
| Apr. 8, 2002 | (JP) | 2002-105376 |

(51) Int. Cl.
*A61B 17/28* (2006.01)
*A61B 17/32* (2006.01)

(52) U.S. Cl. .................. 606/205; 606/170; 606/174
(58) Field of Classification Search ........ 606/205–208, 606/170, 174
See application file for complete search history.

(56) References Cited

U.S. PATENT DOCUMENTS

| 2,028,635 A | 1/1936 | Wappler | 174/89 |
| 4,763,669 A | 8/1988 | Jaeger | 128/751 |
| 4,872,456 A | 10/1989 | Hasson | 128/321 |
| 5,275,608 A | 1/1994 | Forman et al. | 606/170 |
| 5,282,826 A | 2/1994 | Quadri | |
| 5,332,142 A | 7/1994 | Robinson et al. | |

(Continued)

FOREIGN PATENT DOCUMENTS

DE 197 03 600 A1 8/1998

(Continued)

OTHER PUBLICATIONS

European Patent Office Search Report dated Mar. 25, 2003 relative to application EP 02 00 8209 with three new references, the other references previously filed in PTO on Dec. 4, 2002.

(Continued)

*Primary Examiner*—Julian W. Woo
*Assistant Examiner*—Sarah Webb
(74) *Attorney, Agent, or Firm*—Ostrolenk, Faber, Gerb & Soffen, LLP

(57) ABSTRACT

A surgical instrument of the present invention comprises a tool section provided at a distal end of the insert section, having first and second tool pieces connected to each other by a first opening/closing pivot axis, and a manipulating section provided at a proximal end of the insert section, having first and second manipulating bodies connected to each other by a second opening/closing pivot axis wherein the first opening/closing pivot axis is positioned at a first side relative to the longitudinal center axis of the insert section, the second opening/closing pivot axis is positioned at a second side relative to the longitudinal center axis of the insert section, and the first side and second side are established to obtain a positional relationship which is substantially symmetrical to each other relative to the longitudinal center axis of the insert section.

3 Claims, 42 Drawing Sheets

U.S. PATENT DOCUMENTS

| | | | | |
|---|---|---|---|---|
| 5,350,391 A * | 9/1994 | Iacovelli | ...................... | 606/207 |
| 5,383,888 A | 1/1995 | Zvenyatsky et al. | ......... | 606/206 |
| 5,474,571 A | 12/1995 | Lang | .......................... | 606/205 |
| 5,520,678 A | 5/1996 | Heckele et al. | ................ | 606/1 |
| 5,582,617 A | 12/1996 | Klieman et al. | ............ | 606/170 |
| 5,607,450 A | 3/1997 | Zvenyatsky et al. | ......... | 606/206 |
| 5,702,408 A * | 12/1997 | Wales et al. | ................ | 606/205 |
| 5,704,925 A | 1/1998 | Otten et al. | | |
| 5,766,205 A | 6/1998 | Zvenyatsky et al. | ......... | 606/206 |
| 5,782,859 A | 7/1998 | Nicholas et al. | ............ | 606/205 |
| 5,997,565 A | 12/1999 | Inoue | .......................... | 606/205 |
| 6,206,903 B1 | 3/2001 | Ramans | | |
| 6,936,061 B1 * | 8/2005 | Sasaki | ......................... | 606/205 |

FOREIGN PATENT DOCUMENTS

| | | |
|---|---|---|
| EP | 0600182 | 10/1993 |
| EP | 0621009 | 4/1994 |
| FR | 1430639 | 1/1966 |
| JP | 63-109114 | 7/1988 |
| JP | 1-274727 | 11/1989 |
| JP | 5-285079 | 11/1993 |
| JP | 6-197906 | 7/1994 |
| JP | 10-174689 | 6/1998 |
| JP | 2000-254135 | 9/2000 |
| JP | 2001-46329 | 2/2001 |
| JP | 2001-61770 | 3/2001 |
| JP | WO01/82807 | 11/2001 |

OTHER PUBLICATIONS

Untranslated Office Action issued by Japanese Patent Office on Aug. 9, 2005 in in connection with corresponding Japanese application No. 2001-119905.

English translation of Japanese Office Action dated Aug. 9, 2005 issued in connection with corresponding Japanese application No. 2001-119905.

Untranslated Office Action issued by Japanese Patent Office on Aug. 2, 2005 in in connection with corresponding Japanese application No. 2001-119904.

English translation of Japanese Office Action dated Aug. 2, 2005 issued in connection with corresponding Japanese application No. 2001-119904.

Untranslated Office Action issued by Japanese Patent Office on Nov. 8, 2005 in in connection with corresponding Japanese application No. 2001-119904.

English translation of Japanese Office Action dated Nov. 8, 2005 issued in connection with corresponding Japanese application No. 2001-119904.

Untranslated Office Action issued by Japanese Patent Office on Nov. 21, 2005 in in connection with corresponding Japanese application No. 2001-350766.

English translation of Japanese Office Action dated Nov. 21, 2005 issued in connection with corresponding Japanese application No. 2001-350766.

Japanese Office Action dated Jan. 17, 2006 and English translation thereof.

* cited by examiner

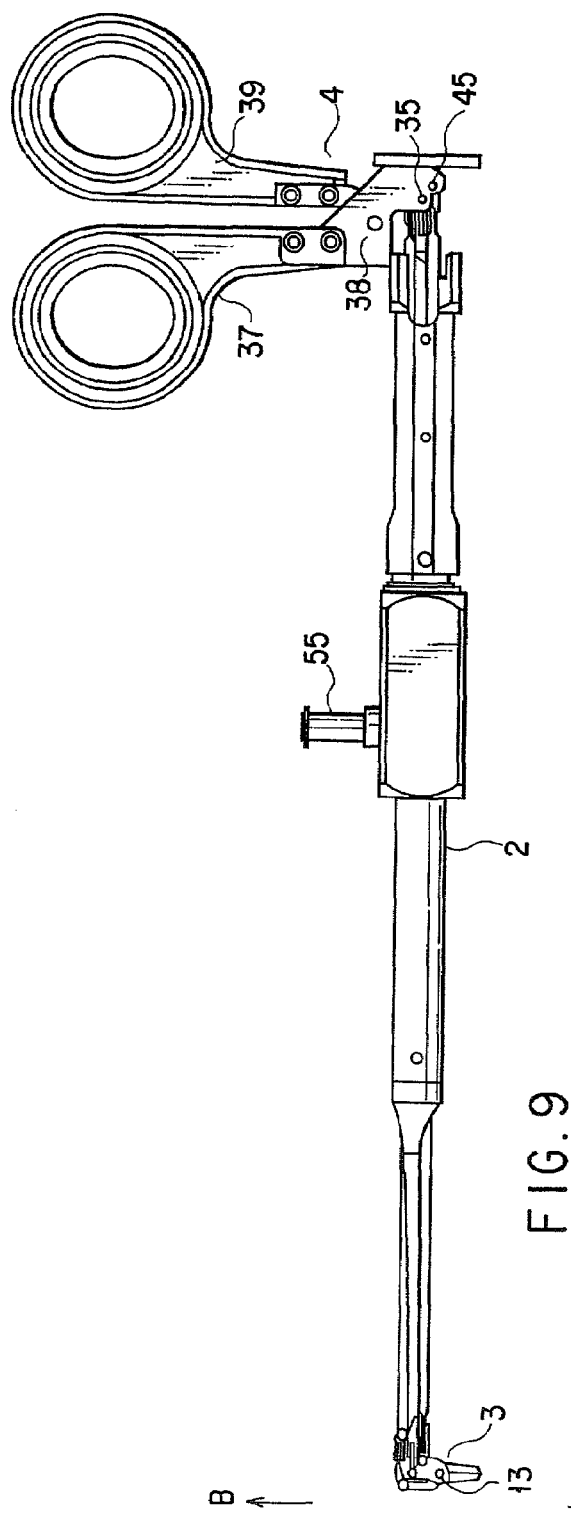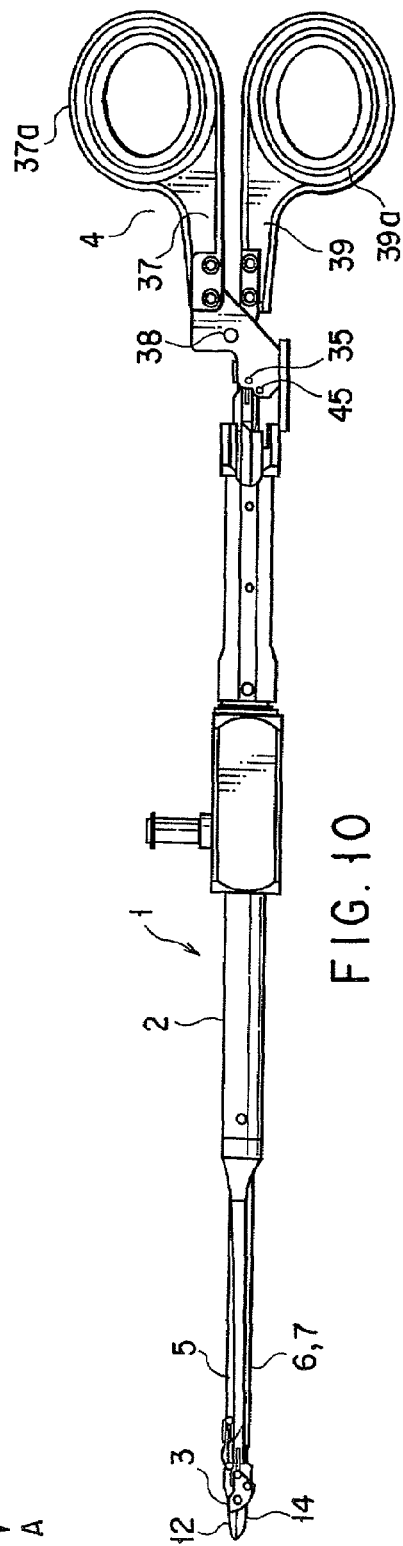
FIG. 9
FIG. 10

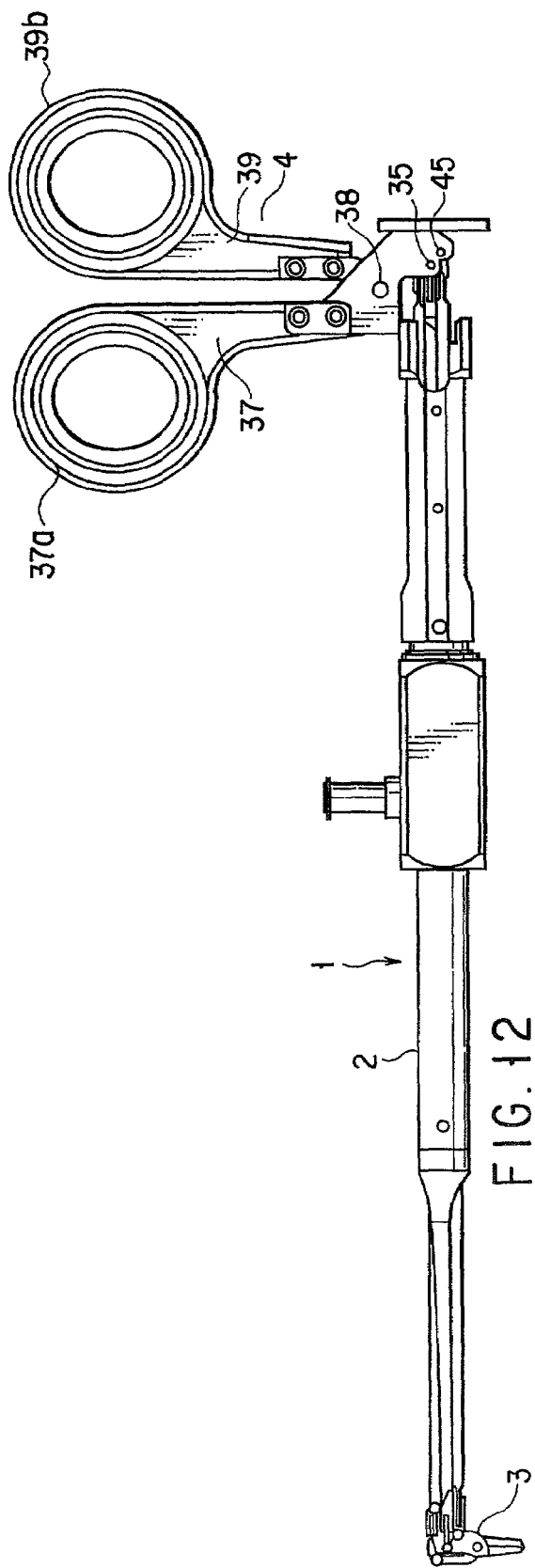
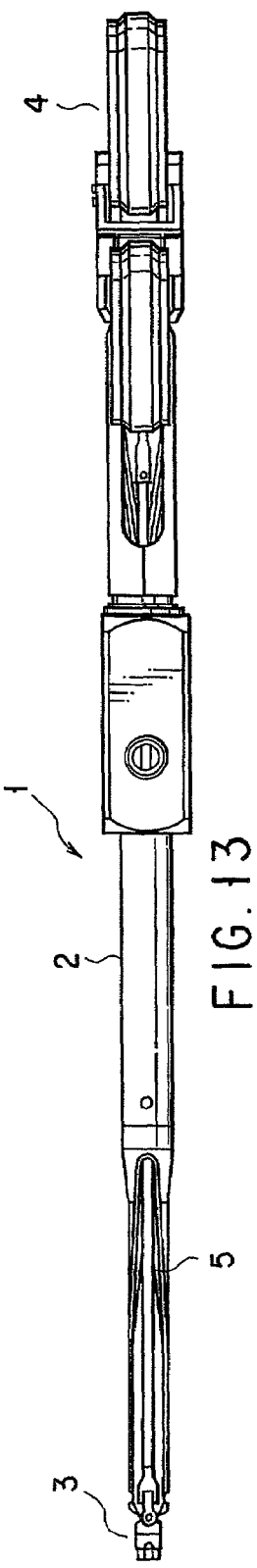
FIG. 12
FIG. 13

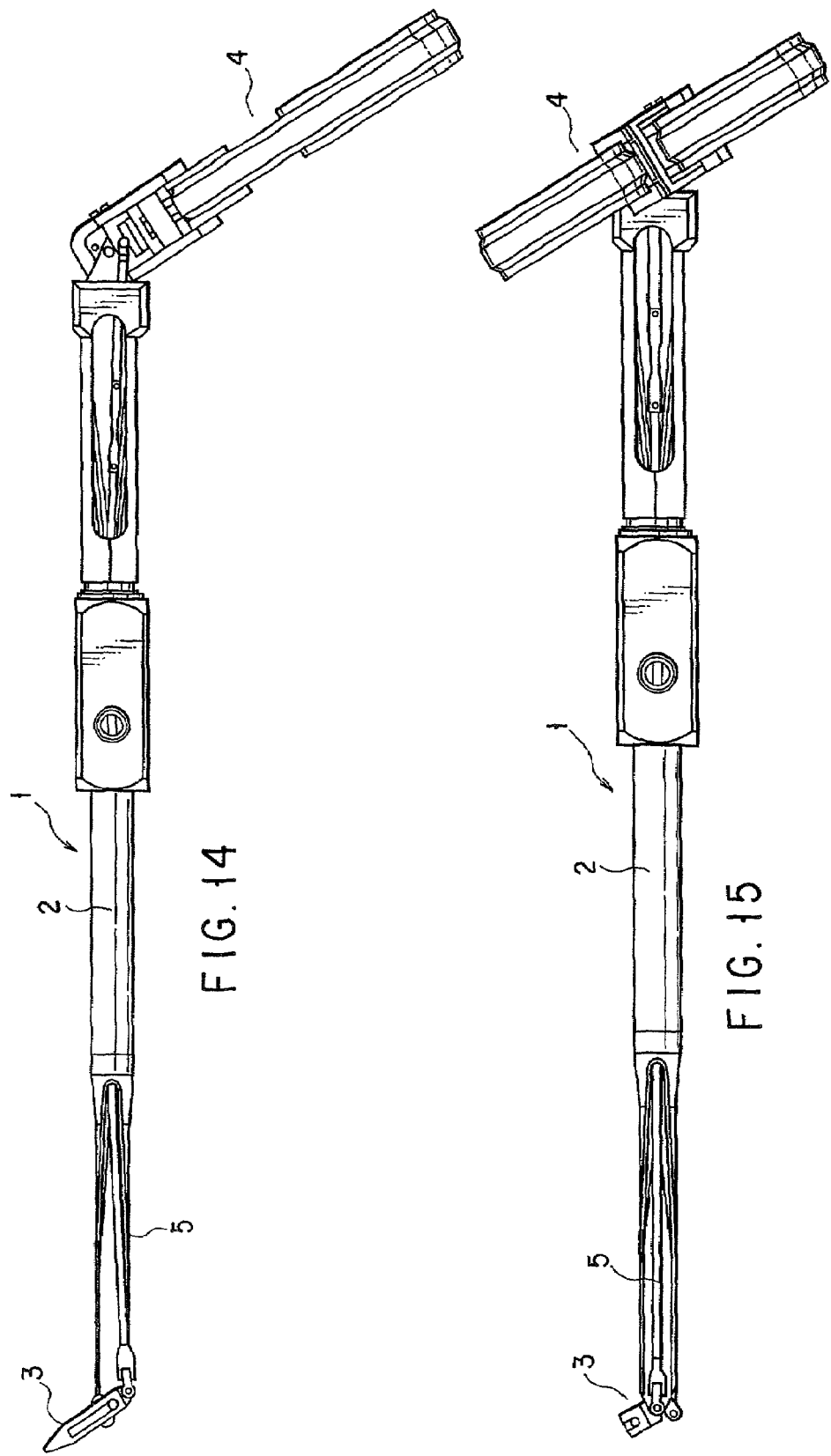

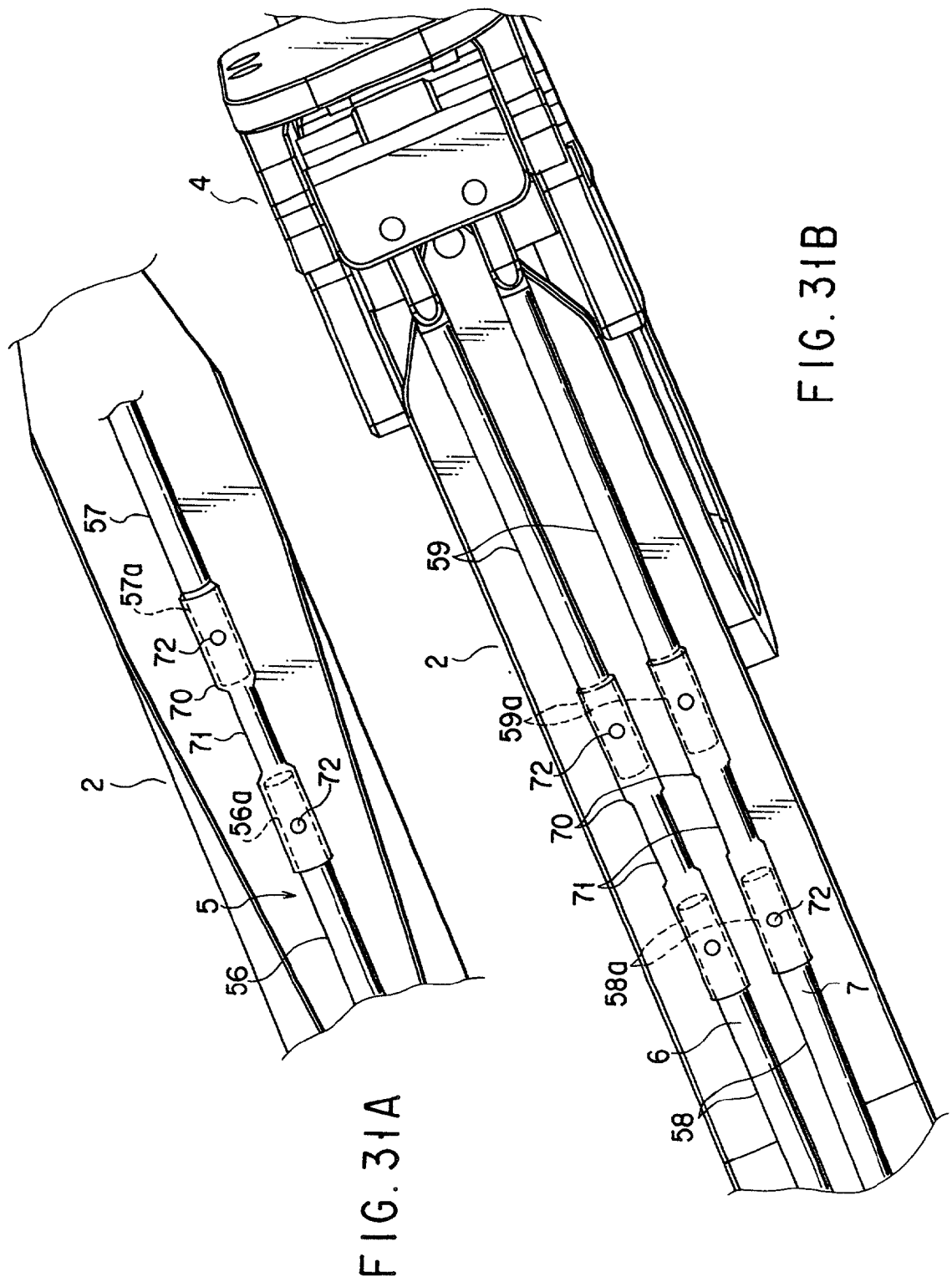

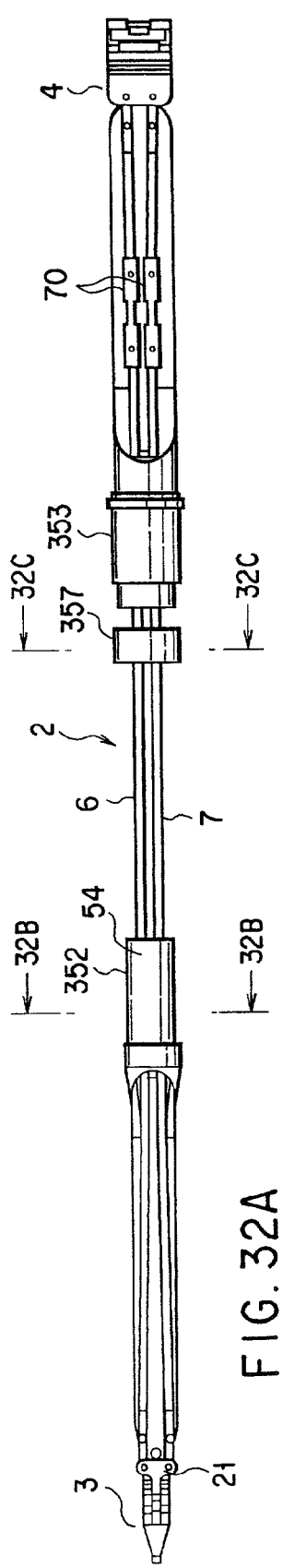
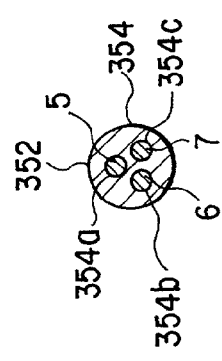
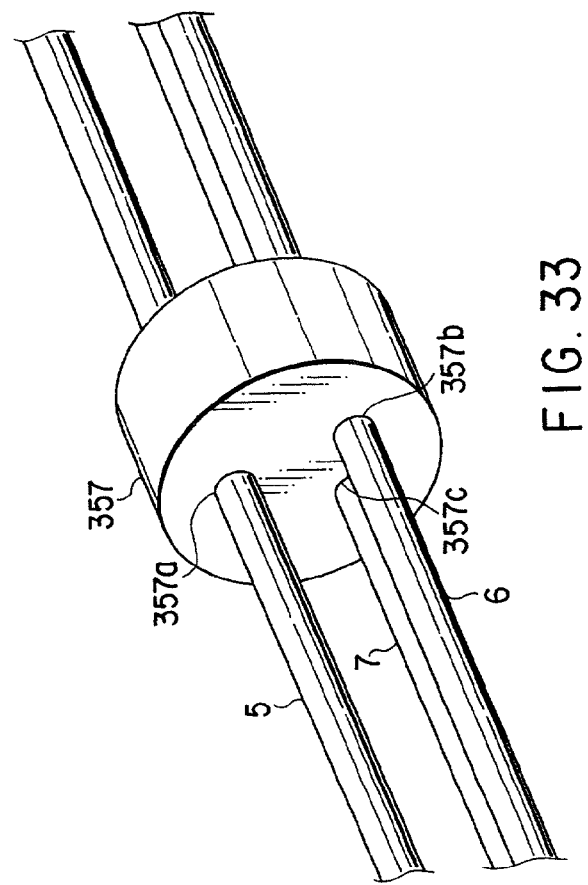
FIG. 32A
FIG. 32B
FIG. 32C
FIG. 33

SURGICAL INSTRUMENT

CROSS-REFERENCE TO RELATED APPLICATIONS

This application is based upon and claims the benefit of priority from the prior Japanese Patent Applications No. 2001-119901, filed Apr. 18, 2001, No. 2001-119902, filed Apr. 18, 2001, No. 2001-119903, filed Apr. 18, 2001, No. 2001-119904, filed Apr. 18, 2001, No. 2001-119905, filed Apr. 18, 2001, No. 2001-350765, filed Nov. 15, 2001, No. 2001-350766, filed Nov. 15, 2001, No. 2001-350767, filed Nov. 15, 2001; and No. 2002-105376, filed Apr. 8, 2002, the entire contents of all of which are incorporated herein by reference.

BACKGROUND OF THE INVENTION

1. Field of the Invention

The present invention relates to a surgical instrument comprising: an insert section inserted into a patient's body; a manipulating section provided at a proximal end section of the insert section and gripped by a surgeon; and a tool section provided at a distal end of the insert section and articulated and opened/closed by the manipulating section.

2. Description of the Related Art

Surgical instruments carrying out surgical operation are disclosed in U.S. Pat. Nos. 5,275,608, 5,702,408, 5,383,888, and 4,763,669.

The surgical instrument disclosed in U.S. Pat. No. 5,275,608 is composed of: a shaft, an openable/closable tool section provided at a proximal end section of this shaft; and a handle provided at a distal end section of the shaft. The tool section is composed so that it can be articulated in the same plane by means of a handle manipulation other than an opening/closing manipulation.

The surgical instrument disclosed in U.S. Pat. No. 5,702,408 comprises: a link lever shaped first link; and second and third links connected to the first link, wherein the second and third links can be moved inwardly each other, and a fourth link is connected to both link end sections. The tool section and manipulating section are set at the same angle by means of a parallel link mechanism for articulating the first link in a first direction and articulating the fourth link in the first direction.

The surgical instrument disclosed in U.S. Pat. No. 5,383,888 is composed of: a shaft; an openable/closable and articulable tool section provided at the proximal end section of this shaft; and a handle provided at the distal end section of the shaft. A tool section is opened/closed by a handle manipulation, and a manipulating wire is advanced/retracted by a lever provided at the handle side, whereby the tool section is articulated.

The surgical instrument disclosed in U.S. Pat. No. 4,763,669 is composed of a shaft; an openable/closable and articulable tool section provided at the distal end section of this shaft; and a handle provided at the proximal end section of the shaft. The tool section is opened/closed by the handle manipulation, and a push rod is advanced/retracted by a lever provided at a handle side, whereby the tool section is articulated.

However, almost of the previously-described conventional surgical instrument is articulated on only a single plane. Thus, in particular, when a complicated manipulation for suturing/ligating tissues is achieved, the degree of freedom for articulating is insufficient.

The previously-described surgical instrument can articulate and rotate the tool section from the manipulating section side. However, while a single thumb and fingers other than the thumb are hooked on the manipulating section, it is difficult to turn the tool section and approach it to a target site by manipulation using the same one hand and to close and open the tool section at the target site. Thus, it is difficult to divert the previously-described surgical instrument for suturing and ligating. In actuality, there does not exist a surgical instrument suitable for suturing/ligating, the surgical instrument being capable of being articulated in an arbitrary direction and being capable of being opened/closed by one hand.

The previously-described surgical instrument disclosed in U.S. Pat. No. 5,272,608 basically has a link in which the manipulating section and tool section move at an equal angle. However, a link composed of: a manipulating section side member made of a disk having a fixed rotary shaft at its center; a main shaft and a movable shaft parallel to this main shaft; and a tool section side member having a fixed rotary shaft at its center, is housed in an insert shaft at its proximal end side. Thus, in fact, the effective width of the manipulating section side member cannot be set to a necessary and sufficient value. In addition, an articulating torque generated by articulating of the manipulating section cannot be sufficiently obtained. Further, the main shaft extends the center of the insert section. Thus, a substantial link width is reduced, and similar effect is considered. U.S. Pat. No. 5,275,608 discusses only articulating on one plane. An articulating ratio between the manipulating section side member and tool section side member cannot be set in a plurality of articulating planes, or alternatively, an articulating manipulation cannot be executed. A flexible member is used for an opening/closing mechanism in order to cope with displacement of a mechanism caused by an articulating manipulation. As a result, the required opening/closing gripping force and direct manipulation may be degraded.

An articulating mechanism caused by a parallel link is disclosed in the previously-described U.S. Pat. No. 5,702,408. However, a mechanism for opening/closing manipulation is not suggested, and an embodiment of the surgical instrument having an equal articulating angle at the manipulating section side and at the tool section side is merely disclosed. In the art disclosed in U.S. Pat. No. 5,702,408, the manipulating section and tool section are connected to each other by means of a simple pair of links, and thus, the entire link is moved in a diameter direction of the insert section by manipulation of the manipulating section. Therefore, a sufficient space is required so that a link does not interfere with an internal hole of the insert section. As a result, there is a problem that the insert section is increased in diameter. When the link is long, an error easily occurs between an articulating manipulation quantity of the manipulating section and articulating movement quantity of the tool section due to slackness of the link itself.

A general problem in the previously-described prior art is that, when the tool section is set into the desirable articulating state by articulating the manipulating section, if a surgeon turns a manipulating section excessively, or if a surgeon articulates a manipulating section with an excessive force, the tool section may be deformed or destroyed so that a normal operation may be failed.

In general, when tissues are ligated by the surgical instrument, a so-called thread manipulation of surgical ligation or the like, for winding a suture thread connected to a suture needle around the surgical instrument for manipulating it, is carried out. However, a transmission member such as link for transmitting manipulation of the manipulating section to the tool section is articulably connected to the insert section each other by a pivot pin. In general, a step is generated at a connecting section between the transmission members. Thus, the suture thread is hooked on the step, and there is a possibility that smooth ligating manipulation is inhibited.

BRIEF SUMMARY OF THE INVENTION

It is an object of the present invention to provide a surgical instrument with its excellent operability and durability, in which, while a single thumb and fingers other than the thumb are engaged with a manipulating section, a tool section can be articulated in an arbitrary direction relative to an insert section with such one hand, and tissue suturing/ligating manipulation can be easily executed by opening/closing the tool section.

An object of the present invention is achieved by the following surgical instrument. That is, a surgical instrument according to one aspect of the present invention comprises:

an insert section inserted into a patient's body;

a tool section which is provided at a distal end of the insert section, which has first and second tool pieces connected to each other by a first opening/closing pivot axis and opened/closed by being turned relative to each other around the first opening/closing pivot axis, and which is capable of being articulated around at least one first articulating pivot axis orthogonal to a longitudinal center axis of the insert section;

a manipulating section which is provided at a proximal end of the insert section, which has first and second manipulating bodies connected to each other by a second opening/closing pivot axis and opened/closed by being turned relative to each other around the second opening/closing pivot axis, and which is capable of being articulated around at least one second articulating pivot axis orthogonal to the longitudinal center axis of the insert section;

a first link mechanism which connects the first manipulating body and the first tool piece to each other and causes the first tool piece to be articulated around the first articulating pivot axis due to articulating of the first manipulating body around the second articulating pivot axis; and a second link mechanism which connects the second manipulating body and the second tool piece to each other and causes the second tool piece to be turned around the first opening/closing pivot axis due to turning of the second manipulating body around the second opening/closing pivot axis, wherein the first opening/closing pivot axis is positioned at a first side relative to a longitudinal center axis of the insert section, the second opening/closing pivot axis is positioned at a second side relative to a longitudinal center axis of the insert section, and the first side and the second side form a substantially symmetrical position relationship each other relative to the longitudinal center axis of the insert section.

BRIEF DESCRIPTION OF THE SEVERAL VIEWS OF THE DRAWING

FIG. 9 is a side view showing the entirety of the surgical instrument of FIG. 1;

FIG. 10 is a side view showing the surgical instrument of FIG. 1 while the tool section is placed horizontally;

FIG. 12 is a side view showing the surgical instrument of FIG. 1 while the tool section is lowered downwardly;

FIG. 13 is a plan view showing the surgical instrument of FIG. 1 while the tool section is lowered downwardly;

FIG. 14 is a plan view showing the surgical instrument of FIG. 1 while the tool section is placed horizontally, and is articulated in a transverse direction;

FIG. 15 is a plan view showing the surgical instrument of FIG. 1 while the tool section is bent downwardly, and is articulated in the transverse direction;

FIG. 31A is a perspective view showing adjusting means in a first drive rod of a surgical instrument according to a sixth embodiment of the present invention;

FIG. 31B is a perspective view showing adjusting means in second and third drive rods of the surgical instrument according to the sixth embodiment of the present invention;

FIG. 32A is a bottom view showing a state in which a tool section of a surgical instrument according to a seventh embodiment of the present invention is placed straight;

FIG. 32B is a sectional view taken along the line 32B—32B of FIG. 32A;

FIG. 32C is a sectional view taken along the line 32C—32C of FIG. 32A;

FIG. 33 is a perspective view showing a sealing member of a surgical instrument of FIG. 32A;

DETAILED DESCRIPTION OF THE INVENTION

Hereinafter, preferred embodiments of the present invention will be described with reference to the accompanying drawings.

Figure 1:
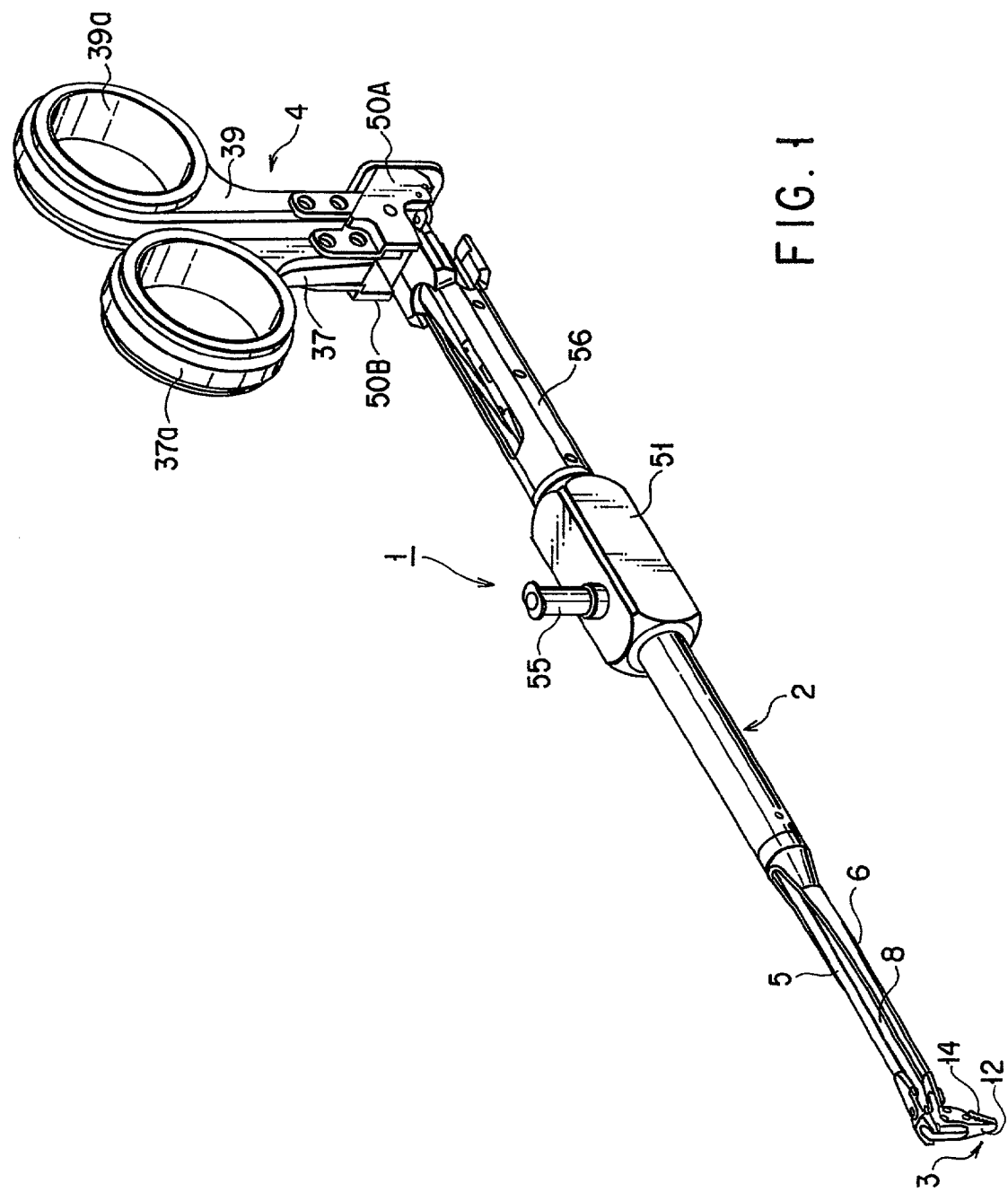
FIG. 1 is a perspective view showing an entire construction of a surgical instrument according to a first embodiment of the present invention.

FIG. 1 to FIG. 16B show a first embodiment of the present invention. As shown in FIG. 1, a surgical instrument 1 according to the present invention is composed of: an insert section 2; a tool section 3 provided at a distal end section of the insert section 2; and a manipulating section 4 provided at a proximal end section of the insert section 2.

As shown in FIG. 2 to FIG. 6, a first drive rod 5 configuring an opening/closing link mechanism that consists of a convergent bar and a second drive rod 6 and a third drive rod 7 each configuring an articulating link mechanism are inserted into the insert section 2 in a parallel or substantially parallel to each other. The first drive rod 5 is disposed eccentrically at one side of the longitudinal center axis of the insert section 2 (upwardly in the present embodiment). The second and third drive rods 6 and 7 are disposed in a transversely symmetrical manner (downwardly in the present embodiment) eccentrically at the opposite side of the first drive rod 5 relative to the longitudinal center axis of the insert section 2. In addition, these drive rods can be advanced/retracted independently of each other in an axial direction.

Figure 2:
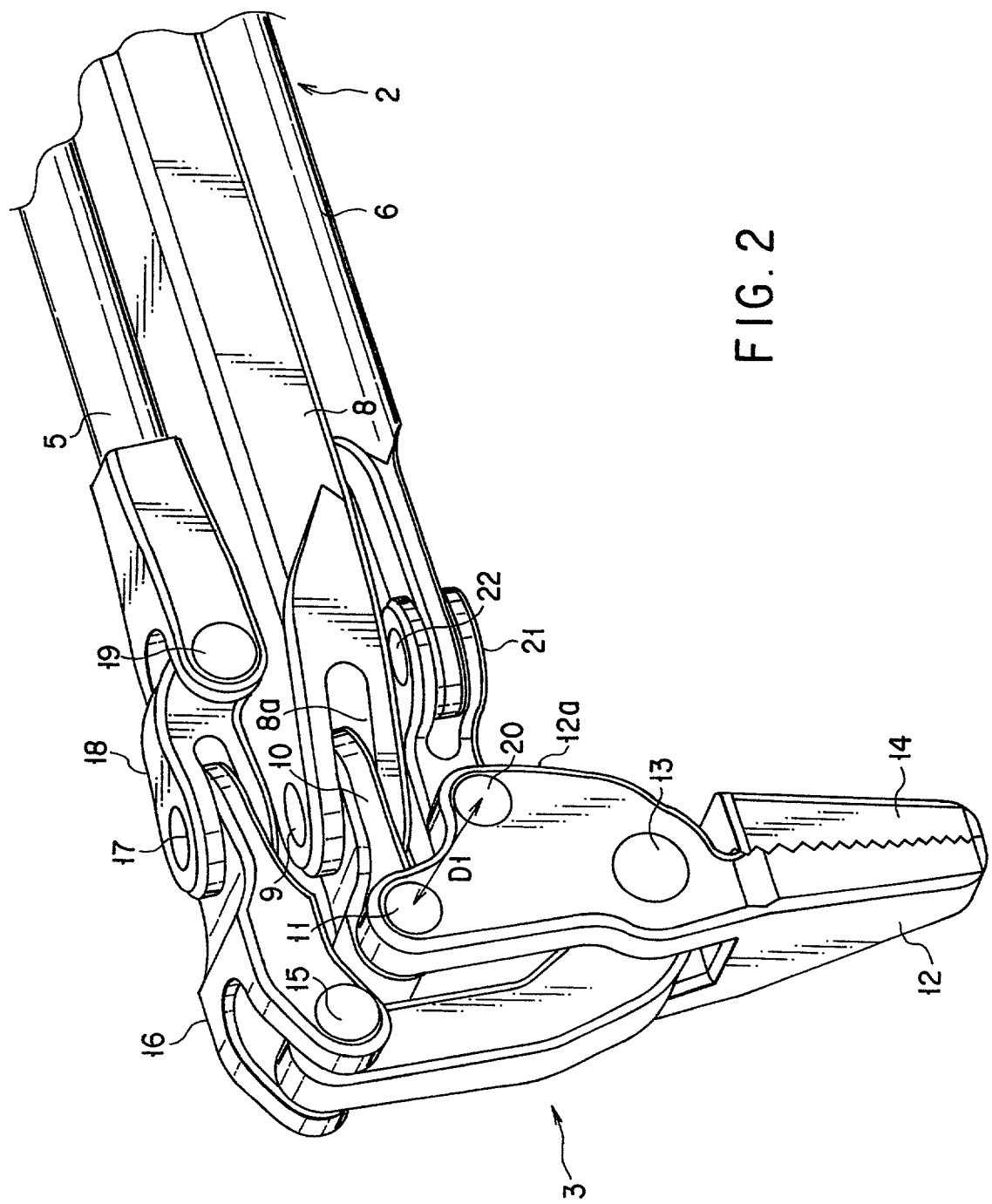
FIG. 2 is a perspective view when a tool section of a surgical instrument of FIG. 1 is seen from the top.
Figure 3:
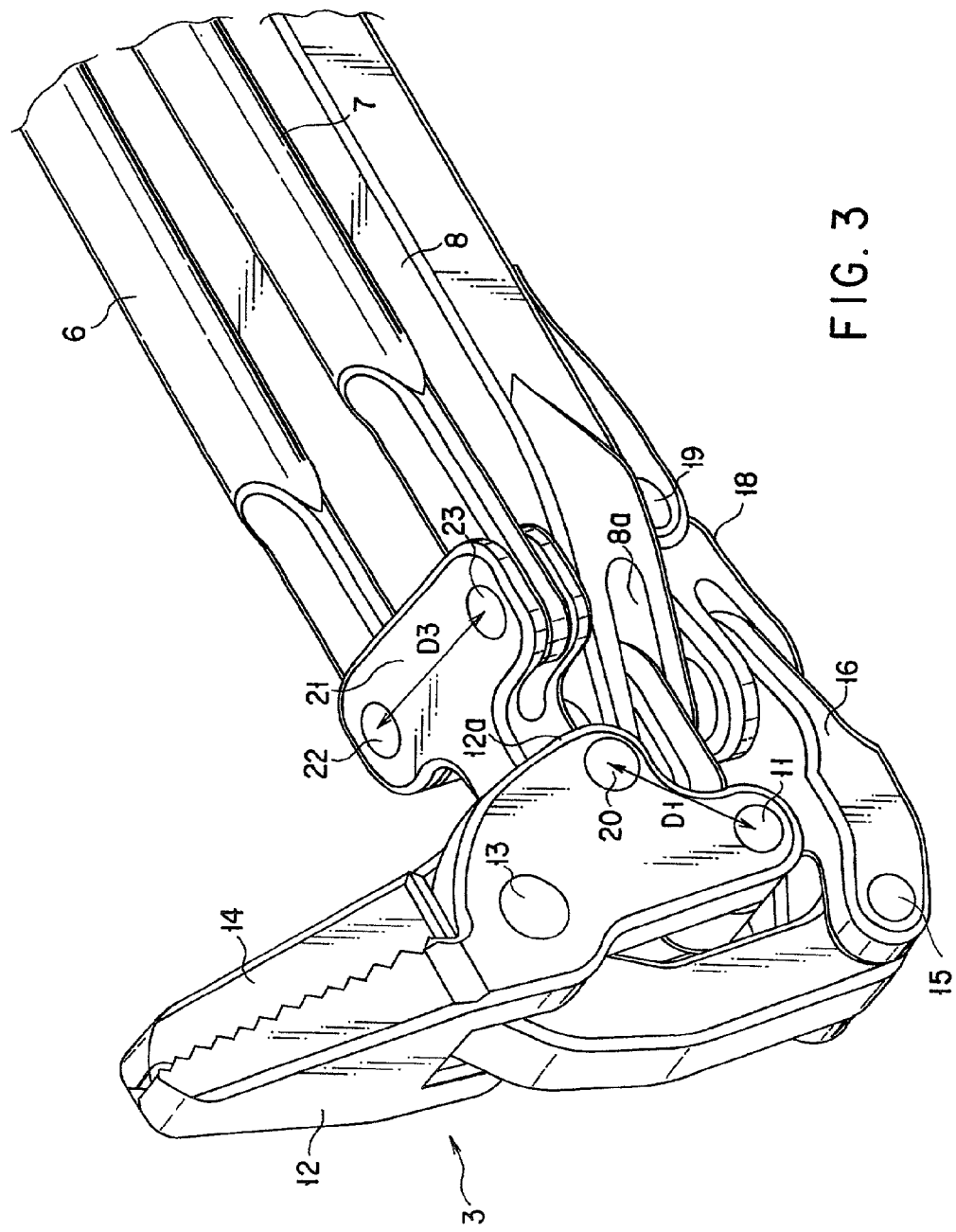
FIG. 3 is a perspective view when the tool section of a surgical instrument of FIG. 1 is seen from the bottom.

FIG. 2 and FIG. 3 show the tool section 3 in detail. As shown in the figures, a first support section 8 forwardly protruded and having rigidity is integrally provided at a distal end section of the insert section 2. A split section 8a is provided at the distal end section of this first support section 8, and a first turn plate 10 which can be articulated in a transverse direction is connected to this split section 8a by means of a first pivot shaft 9 orthogonal to the axial direction of the insert section 2. A first pivot pin 11 is fixed to this first turn plate 10 in a direction orthogonal to the first pivot shaft 9, and a proximal end section of a first tool piece 12 is articulably pivoted to this first pivot pin 11. In addition, a site of the first tool piece 12 positioned in close proximity to the first pivot pin 11 is formed as a bent section 12a, and the second and third drive rods 6 and 7 are connected to this bent section 12a by means described later.

A second tool piece 14 is turnably connected at an intermediate section of the first tool section 12 by means of a first opening/closing pivot pin 13. In this manner, the first tool piece 12 and second tool piece 14 can be turned each other while the first opening/closing pivot pin 13 is defined as a fulcrum. One end of a first connecting member 16 is turnably connected to a proximal end section of the second tool piece 14 via a first connecting pin 15 extending in a transverse direction (a direction orthogonal to the axial direction of the insert section 2), and the other end of the first connecting member 16 is connected to a second connecting member 18 via a second connecting pin 17 orthogonal to the axial direction of the insert section 2. The other end of the second connecting member 18 is turnably connected to the distal end section of the first drive rod 5 via a third connecting pin 19 extending in a transverse direction.

A second turn plate 21 is connected to the bent section 12a of the first tool piece 12 via a second pivot pin 20 extending in a transverse direction. A proximal end side of this second turn plate 21 is wide in a transverse direction. A first turn pin 22 and a second turn pin 23 orthogonal to the axial direction of the insert section 2 are provided to be spaced in a transverse direction. The first turn pin 22 is connected to the second drive rod 6, and the second turn pin 23 is connected to the third drive rod 7.

Figure 4:
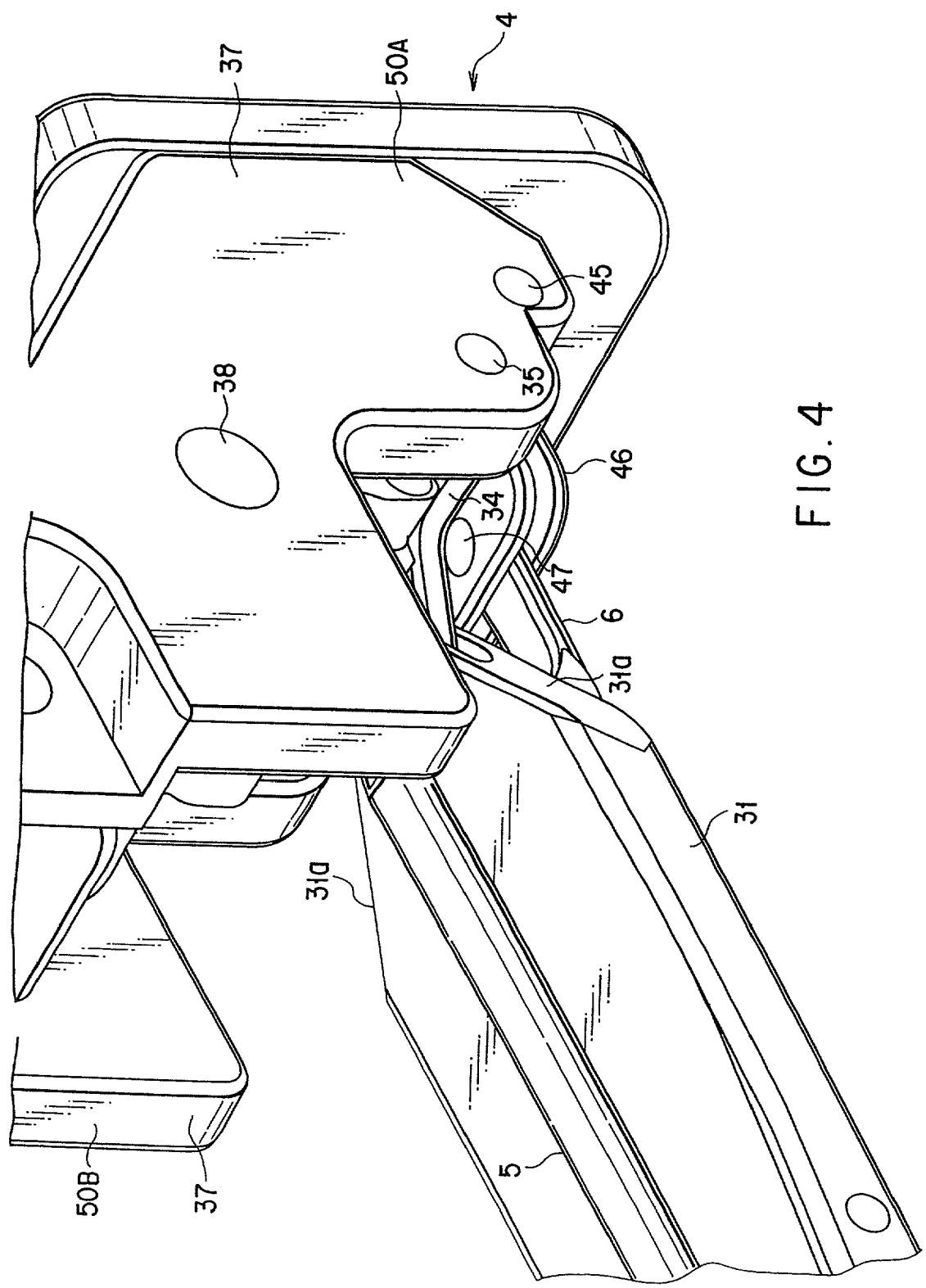
FIG. 4 is a perspective view when a manipulating section of a surgical instrument of FIG. 1 is seen from the top.

Now, a description of a manipulating section 4 will be given with reference to FIG. 4 to FIG. 6.

As is evident from these figures, at the proximal end section of the insert section 2 as well, the first drive rod 5 is disposed so that its proximal end section is eccentric upwardly of the longitudinal center axis of the insert section 2. The second and third drive rods 6 and 7 are disposed so that its proximal end section is symmetric transversely downwardly of the longitudinal center axis of the insert section 2. A second support section 31 protruded backwardly (toward the proximal end side) and having rigidity is provided at the proximal end section of the insert section 2 via a connecting section 51 (refer to FIG. 1). At both sides of the proximal end section of this second support section 31, an abutment receiving face 31a consisting of a convergent taper face is formed toward the proximal end. A first pivot section 33 having a second pivot shaft 32 orthogonal to the axial direction of the insert section 2 is provided at the second support section 31, and a third turn plate 34 that can be articulated around the second pivot shaft 32 is provided at the first pivot shaft 33.

A second pivot section 36 having a third pivot pin 35 extending in a transverse direction is provided at a third turn plate 34. A first handle 37 serving as a first manipulating body that can be vertically articulated around the third pivot pin 35 is connected to this second pivot section 36. At this first handle 37, a second handle 39 serving as a second manipulating body is connected to this first handle 37 vertically turnably. Further, as is clearly shown in FIG. 1, a finger hook ring 37a on which a surgeon hooks one's finger other than thumb during surgeon tool is provided at the first handle 37, and a finger hook ring 39a on which the surgeon hooks one's thumb during manipulation is provided at the second handle 39.

Figure 5:
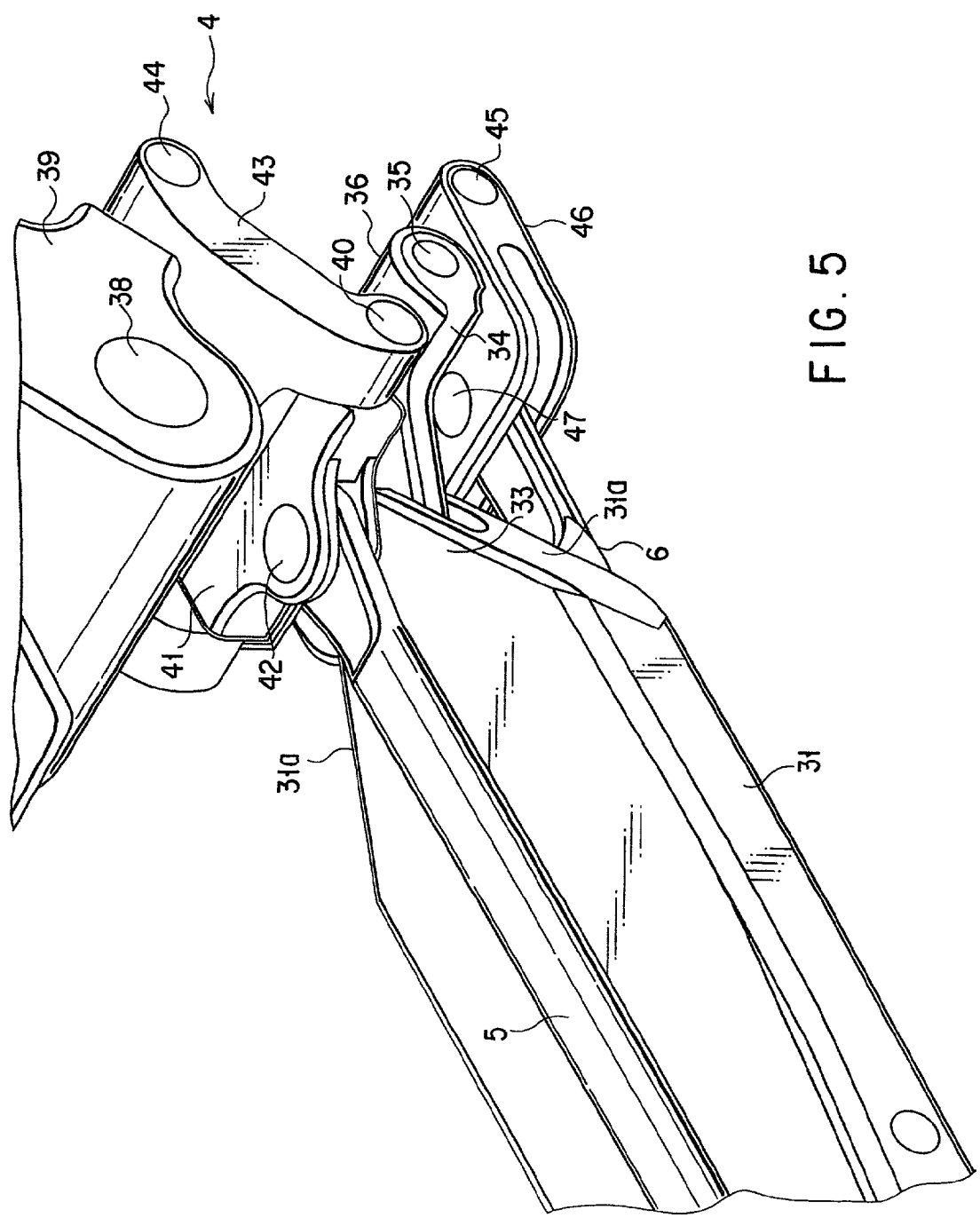
FIG. 5 is a perspective view when the manipulating section of the surgical instrument of FIG. 1 is seen from the top while a cover is removed.
Figure 6:
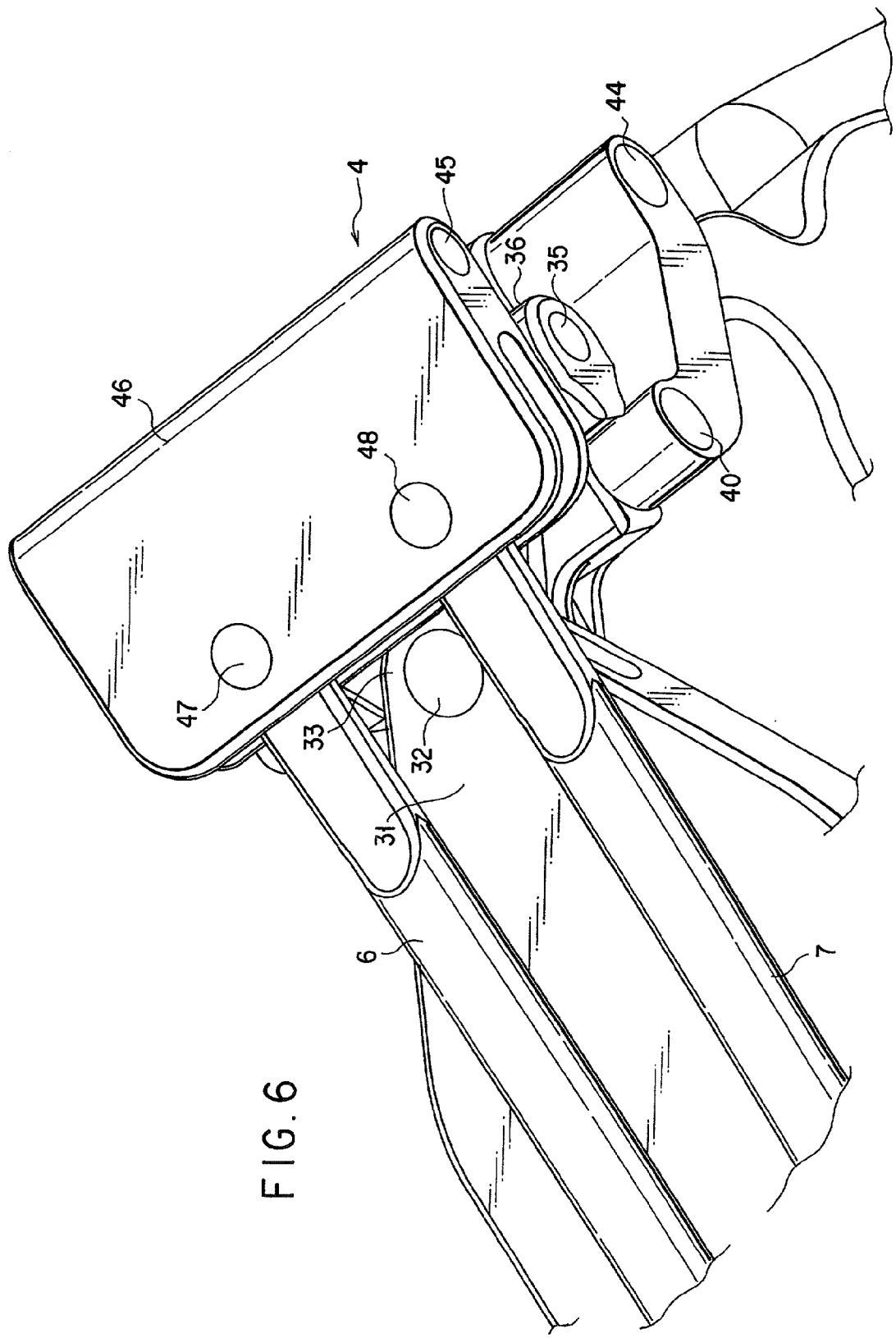
FIG. 6 is a perspective view when the manipulating section of the surgical instrument of FIG. 1 is seen from the bottom while the cover is removed.

As is clearly shown in FIG. 5, a fourth connecting pin 42 orthogonal to the axial direction of the insert section 2 (extending in a vertical direction) is provided at the proximal end section of the first drive rod 5, and a third connecting member 41 is connected to this fourth connecting pin 42 so that the connecting member can be turned in a transverse direction. A fifth connecting pin 40 extending in a transverse direction is provided at this third connecting member 41, and one end of the fourth connecting member 43 is connected to this connecting pin 40 vertically turnably. In addition, a second handle 39 is connected to the other end of the fourth connecting member 43 vertically turnably via a sixth connecting pin 44 extending in a transverse direction.

A fourth pivot pin 45 extending in a transverse direction is positioned in close proximity to the third pivot pin 35 of the first handle 37. This fourth pivot pin 45 is provided at one end of the fourth turn plate 46. The first handle 37 vertically articulating around the third pivot pin 35 is articulably connected to this pin 45. A third turn pin 47 and a fourth turn pin 48 orthogonal to the axial direction of the insert section 2 (extending in a vertical direction) are provided to be transversely spaced at the other end section of the fourth turn plate 46. The proximal end sections of the second and third drive rods 6 and 7 transversely positioned each other is turnably connected to the third turn pin 47 and fourth turn pin 48, respectively. Namely, with this construction, the first and second handles 37 and 39 can be articulated in a transverse direction relative to the second support section 31 around the second pivot shaft 32, and can be articulated in a vertical direction around the third pivot shaft 35.

The periphery of the first pivot section 33 and the second pivot section 36 is covered with covers 50A and 50B that are a part of the first handle 37. As shown in FIG. 1, a connecting section 51 is provided at the substantially intermediate section in the longitudinal direction of the insert section 2, and a wash port 55 communicating with an internal portion of the insert section 2 is provided at this connecting section 51. Then, a syringe or the like is connected to the wash port 55, and a wash liquid is injected into the internal portion of the insert section 2, thereby enabling washing. Reference 56 denotes a guard fixed at a position closer to the manipulating section 4 than the connecting section 51.

Figure 7:
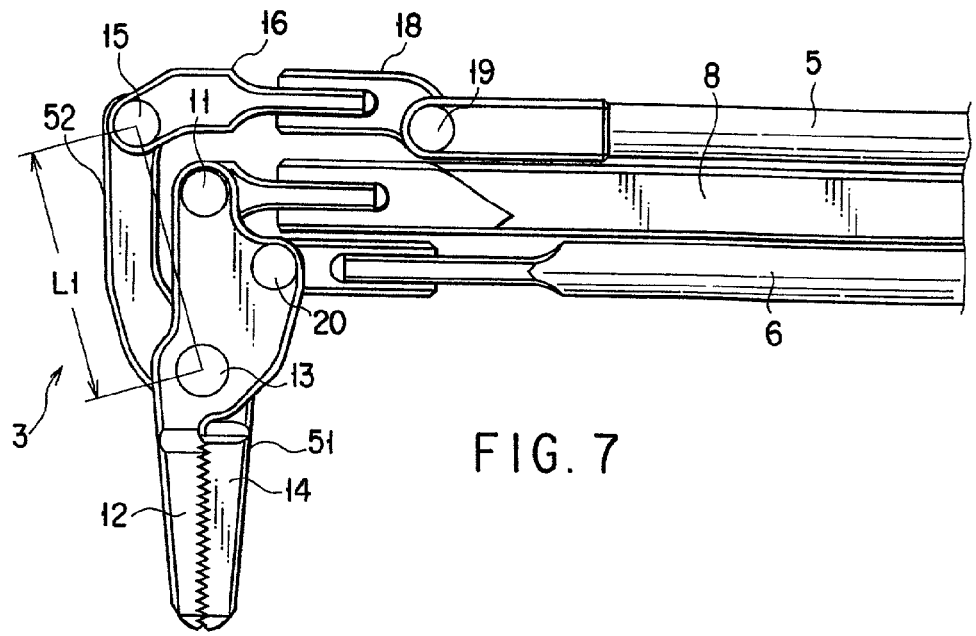
FIG. 7 is a side view showing the tool section of the surgical instrument of FIG. 1.
Figure 8:
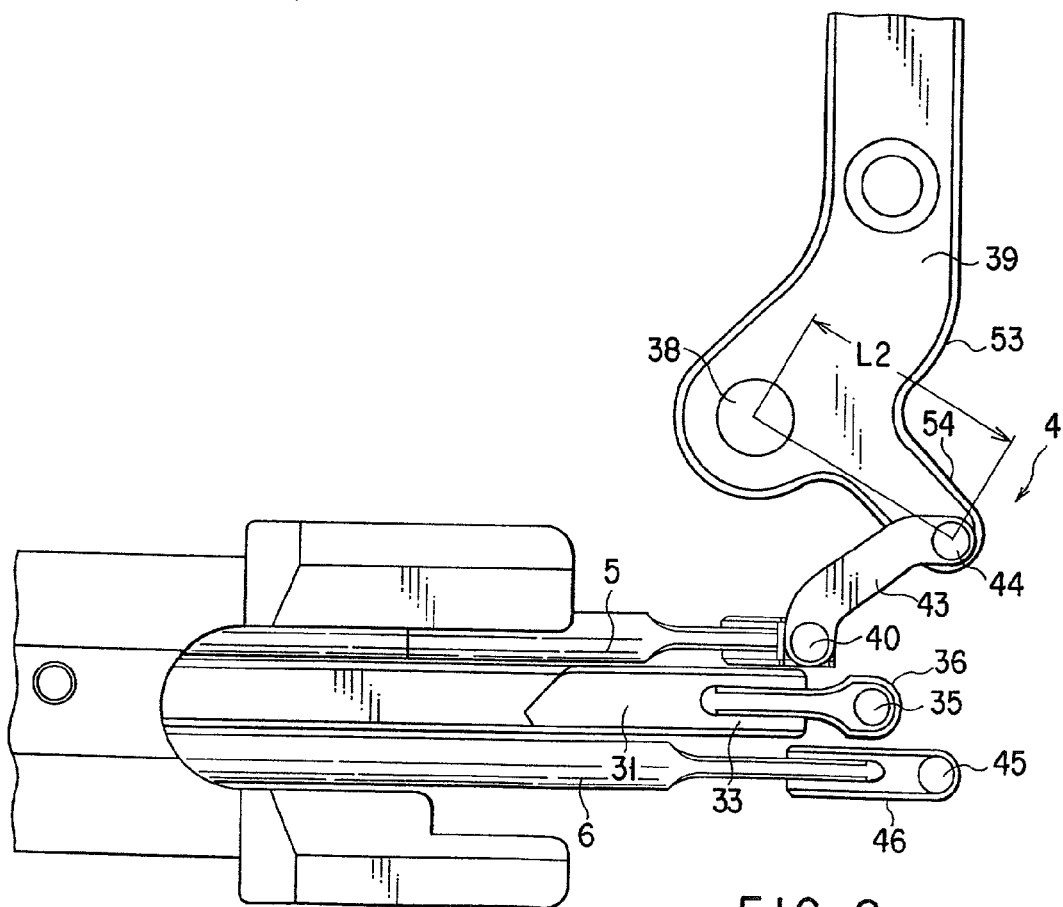
FIG. 8 is a side view showing the manipulating section of the surgical instrument of FIG. 1.

As shown in FIG. 7 that is a side view of the tool section 3, a second tool piece 14 at the tool section 3 is composed of: a grip leg section 51; and a tool section side link leg section 52 extending from this grip leg section 51 over the first opening/closing pivot pin 13. A length of the tool section side link leg section 52 (a distance between the first opening/closing pivot pin 13 and the first connecting pin 15) is defined as L1. As shown in FIG. 8 that is a side view of the manipulating section 4, the second handle 39 serving as a second manipulating body at the manipulating section 4 is composed of: a finger engagement leg section 53; and a manipulating section side link leg section 54 extending over the second opening/closing pivot pin 38 from this finger engagement leg section 53, wherein a length of the manipulating section side link leg section 54 (a distance between the second opening/closing pivot pin 38 and the sixth connecting pin 44) is defined as L2. The length L1 of the tool section side link leg section 52 is defined to be equal to the length L2 of the manipulating section side link leg section 54 so that the second handle 39 is in synchronism with the second tool piece 14.

As shown in FIG. 9 that is a side view of a surgical instrument, the instrument is constructed so that a first opening/closing pivot pin 13 of the second tool piece 14 is positioned at a first side A relative to the longitudinal center axis of the insert section 2 in all the articulating postures of the tool section 3 executed by the first handle 37, and a second opening/closing pivot pin 38 of the second handle 39 is positioned at a second side B relative to the longitudinal center axis of the insert section 2. The first side A and second side B are in a substantially symmetrical position relationship while the longitudinal center axis of the insert section 2 is sandwiched between these sides.

Now, an operation of the surgical instrument 1 constructed as described previously will be described here. When the second and third drive rods 6 and 7 are advanced at the same time from a state shown in FIG. 2 and FIG. 3, a bent section 12a of a first tool piece 12 is extruded forwardly via a second turn plate 21. Thus, a second tool piece 14 connected with the first tool piece 12 as well articulates in the same direction as that of the first tool piece 12 via a first opening/closing pivot pin 13. As a result, the first and second tool pieces 12 and 14 can be articulated up to substantially horizontally around the first pivot pin 11 orthogonal to the longitudinal center axis of the insert section 2.

When a second drive rod 6 is retracted, and a third drive rod 7 is advanced, a first turn plate 10 turns in a clockwise direction (seen from the manipulating section 4 in FIG. 3) around a first pivot shaft 9. Thus, the first and second tool pieces 12 and 14 (the entirety of the tool section 3) are articulated in a clockwise direction (a right-hand direction) around the first pivot shaft 9.

Conversely, when the second drive rod 6 is advanced, and the third drive rod 7 is retracted, the first turn plate 10 turns in a counterclockwise direction (seen from the manipulating section 4 in FIG. 3) around the first pivot shaft 9. Thus, the first and second tool pieces 12 and 14 (the entirety of the tool section 3) are articulated in a counterclockwise direction (a left-hand direction) around the first pivot shaft 9.

In any of the above articulating states as well, if the first drive rod 5 is advanced, the proximal end section of the second tool piece 14 is pressed forwardly via the first connecting member 16 and second connecting member 18. Thus, the second tool piece 14 is turned relative to the first tool piece 12 around the first opening/closing pivot pin 13, whereby the tool section 3 is opened. Conversely, if the first drive rod 5 is retracted from this opened state, the proximal end section of the second tool piece 14 is pulled backwardly via the first connecting member 16 and second connecting member 18. Thus, the second tool piece 14 is turned relative to the first tool piece 12 around the first opening/closing pivot pin 13, and the tool section 3 is closed.

In this way, according to the present embodiment, the entirety of the tool section 3 comprising the openable/closable first and second tool pieces 12 and 14 can be articulated in a vertical direction and a transverse direction. Thus, the first and second tool pieces 12 and 14 can approach a target site easily, and the degree of freedom for tool can be improved.

In actual manipulation, first, any finger other than thumb is hooked on the finger hook ring 37a of the first handle 37 of the manipulating section 4 shown in FIG. 1, and the thumb is hooked on a finger hook ring 39a of a second handle 39. Then, from a horizontal state shown in FIG. 10 and FIG. 11, if the first handle 37 and second handle 39 of the manipulating section 4 are articulated upwardly by 90 degrees at the same time around the third pivot pin 35, the second and third drive rods 6 and 7 are retracted along the insert section 2 via a fourth turn plate 46 at the same time. In addition, together with this retraction, the first drive rod 5 is advanced to the tool section 3 side via the fourth connecting member 43 and the third connecting member 41. Therefore, the bent section 12a of the first tool piece 12 is pulled backwardly via the second turn plate 21, and the first connecting pin 15 is protruded to the distal end side via the first connecting member 16 of the tool section 3 connected to the first drive rod 5. Thus, the first and second tool pieces 12 and 14 are articulated until they are oriented downward by 90 degrees around the first pivot pin 11 while a closed state is maintained without being relatively turned. This state is shown in FIG. 12 and FIG. 13.

Figure 11B:
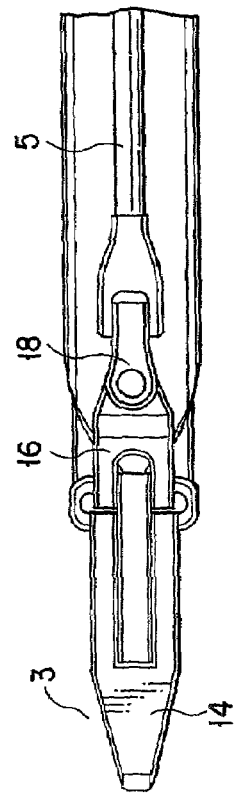
FIG. 11B is an enlarged plan view showing the tool section of the surgical instrument of FIG. 1.
Figure 11A:
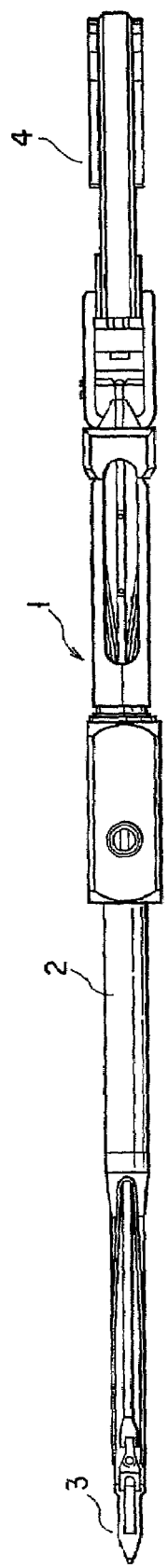
FIG. 11A is a plan view showing the surgical instrument of FIG. 1 while the tool section is placed horizontally.
Figure 11C:
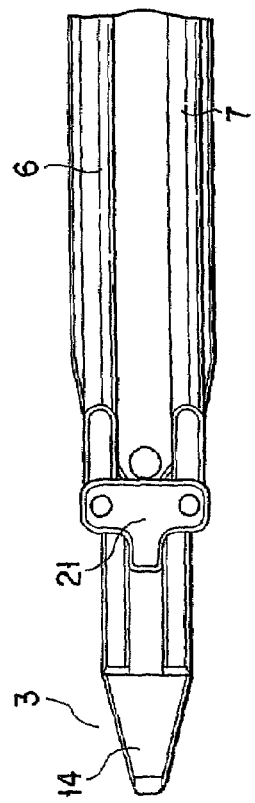
FIG. 11C is an enlarged bottom view showing the tool section of the surgical instrument of FIG. 1.

Conversely, from a state shown in FIG. 12 and FIG. 13, if the first handle 37 and the second handle 39 are articulated downwardly around the third pivot pin 35, whereby the first handle 37 and the second handle 39 are placed horizontally, the second and third drive rods 6 and 7 are advanced along the insert section 2 via the fourth turn plate 46 at the same time. In addition, the first drive rod 5 is retracted to the manipulating section 4 side via the fourth connecting member 43 and the third connecting member 41. Therefore, the bent section 12a of the first tool piece 12 is pushed forwardly via the second turn plate 21. In addition, the first connecting pin 15 is retracted to the manipulating section 4 side via the first connecting member 16 of the tool section 3 side connected to the first drive rod 5 and the second connecting member 18. Thus, the first and second tool pieces 12 and 14 are articulated to be disposed substantially horizontally (straight) around the first pivot pin 11 while the closed state is maintained without being relatively turned. This state is shown in FIG. 10 and FIG. 11.

In this way, in the surgical instrument 1 according to the present embodiment, the first and second handles 37 and 39 of the manipulating section 4 are articulated in a vertical direction around the third pivot pin 35. In this manner, the tool section 3 is positioned straight along the axial direction of the insert section 2, or alternatively, an angle is provided relative to an axis of the insert section 2.

If the first manipulating handle 37 and the second manipulating handle 39 are relatively turned, the first and second tool pieces 12 and 14 are relatively turned, whereby the tool section 3 can be opened. That is, when the second handle 39 is turned relative to the first handle 37 around the second opening/closing pivot pin 38 (when the first handle 37 and the second handle 39 are opened), the first drive rod 5 is advanced or retracted forwardly or backwardly via the fourth connecting member 43 and the third connecting member 41. Therefore, the first connecting pin 15 moves forwardly or backwardly via the first connecting member 16 and the second connecting member 18 at the tool section 3 connected to the first drive rod 5. Thus, the second tool piece 14 is turned relative to the first tool piece 12 around the first opening/closing pivot pin 13, and the tool section 3 opens/closes.

FIG. 14 shows a state in which the first handle 37 and the second handle 39 are articulated together by 60 degrees in the counterclockwise transverse direction (seen from the manipulating section 4). In this state, together with turning of the first handle 37 and second handle 39, the first and second tool pieces 12 and 14 as well are articulated by 60 degrees in the clockwise transverse direction while in their closed state. That is, if the first handle 37 and the second handle 39 are articulated in the counterclockwise direction at the same time around the second pivot shaft 32, the second drive rod 6 is advanced via the fourth turn plate 46, and the third drive rod 7 is retracted. Therefore, the first turn pin 22 at the tool section 3 is advanced, and the second turn pin 23 is retracted. Thus, the first tool piece 12 is articulated in the clockwise direction via the second turn plate 21 around the first pivot shaft 9. As a result, the entirety of the tool section 3 is turned in the clockwise direction.

Conversely, if the first handle 37 and the second handle 39 are articulated in the clockwise direction at the same time around the second pivot shaft 32, the second drive rod 6 is retracted via the fourth turn plate 46, and the third drive rod 7 is advanced. Therefore, the first turn pin 22 at the tool section 3 is retracted, and the second turn pin 23 is advanced. Thus, the first tool piece 12 is articulated in the counterclockwise direction via the second turn plate 21 around the first pivot shaft 9. As a result, the entirety of the tool section 3 is articulated in the counterclockwise direction.

In this way, in the surgical instrument 1 according to the present embodiment, together with articulating in the clockwise direction of the first and second handles 37 and 39, the first and second tool pieces 12 and 14 are articulated in the counterclockwise while these pieces are maintained in substantially parallel to the handles 37 and 39. In addition, together with articulating in the counterclockwise direction of the first and second handles 37 and 39, the first and second tool pieces 12 and 14 are articulated in the clockwise direction while these pieces are maintained in substantially parallel to the handles 37 and 39. That is, the tool section 3 can be oriented in an arbitrary direction by vertical/transverse articulating manipulation of the first and second handles 37 and 39. In a state of FIG. 13, if the first handle 37 and the second handle 39 are articulated by 60 degrees in the counterclockwise transverse direction while in a parallel state, as shown in FIG. 15, the downward first and second tool pieces 12 and 14 are articulated by 60 degrees in the clockwise transverse direction while in a closed state.

Figure 16A:
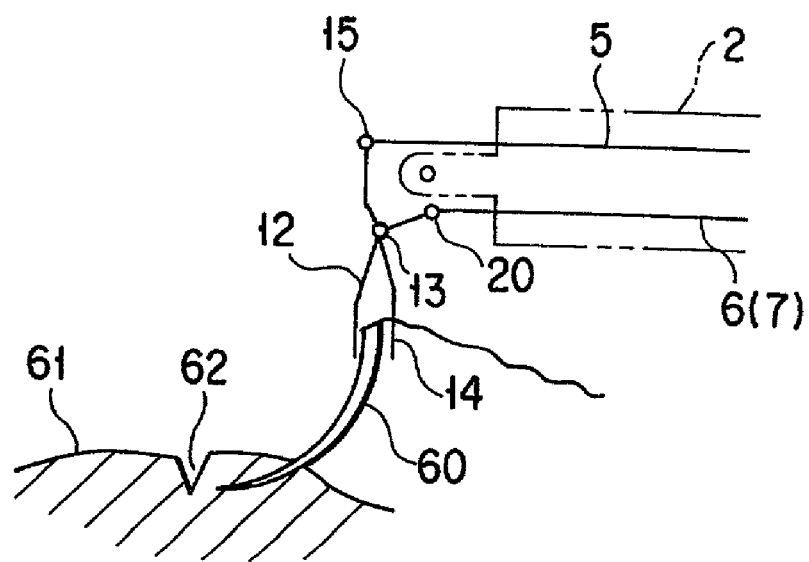
FIG. 16A is a view showing a state in which the surgical instrument of FIG. 1 is used.

Now, a method for suturing a tissue dissecting section using a surgical instrument will be described here. FIG. 16A shows a state in which the second and the third drive rods 6 and 7 are retracted, and the first and second tool pieces 12 and 14 are placed downwardly by being articulated at a substantially right angle relative to the axle of the insert section 2, the state indicating that the threaded suture needle 60 is gripped by the first and second tool pieces 12 and 14. In this state, when the suture needle 60 is positioned in close proximal to a dissecting section 62 of the tissue 61, and the distal end section of the insert section 2 is pushed down in the direction of the tissue 61, the suture needle 60 is punctured into the tissue 61.

Figure 16B:
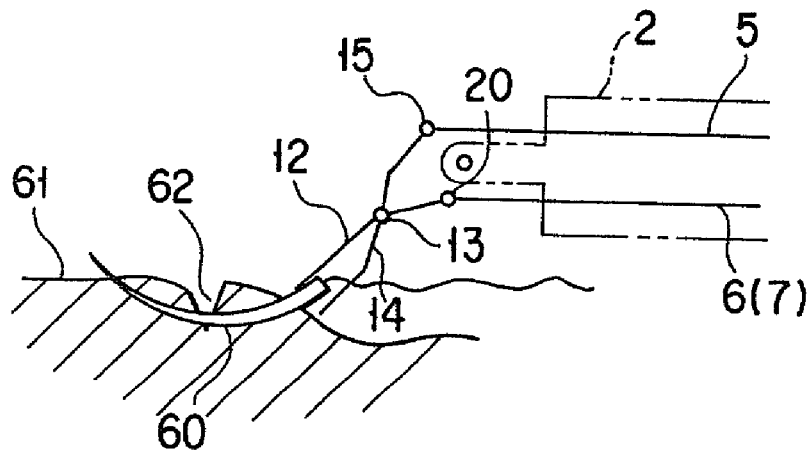
FIG. 16B is a view showing a state in which the surgical instrument of FIG. 1 is used.

When the second and the third drive rods 6 and 7 are advanced, the first tool piece 12 and the second tool piece 14 are articulated forwardly around the first pivot pin 11. Thus, as shown in FIG. 16B, the suture needle 60 is punctured into the tissue 61 having the dissecting section 62, and the distal end section of the suture needle 60 is protruded from a surface layer of the tissue 61. In this way, the first and second tool pieces 12 and 14 can be articulated in the axial direction of the suture needle 60, whereby puncture of the suture needle 60 can be easily carried out.

As described previously, even in a state in which the first and second tool pieces 12 and 14 are oriented in the axial direction of the insert section 2, or alternatively, in a state in which these pieces are articulated to be displaced downwardly at a substantially right angle relative to the axle, the first and second tool pieces 12 and 14 can be opened/closed by turning them. These pieces can approach a target site reliably, and if the shape of the tool pieces 12 and 14 are changed as desired, gripping or exfoliation (separation) of the tissue 61 rather than suturing can be easily carried out.

Further, when the suture needle 60 is gripped by the first and second tool pieces 12 and 14 for suturing, for example, the first and second handles 37 and 39 are articulated in a transverse direction around the first pivot section 32. In this manner, the first and second tool pieces 12 and 14 can be articulated in the transverse direction. Thus, even if the suture direction has an angle relative to the axial direction of the insert section 2, a surgeon can carry out suture operation by means of the suture needle 60 without shifting it from one hand to another hand. In addition, it is unnecessary to make a complicated manipulation that the surgical instrument 1 is inserted again in another direction.

FIG. 17 to FIG. 24 show a second embodiment of the present invention. The present embodiment is directed to a modified example of the first embodiment. Like constituent elements common to those of the first embodiment are designated by like reference numerals. A detailed description thereof is omitted here.

Figure 17:
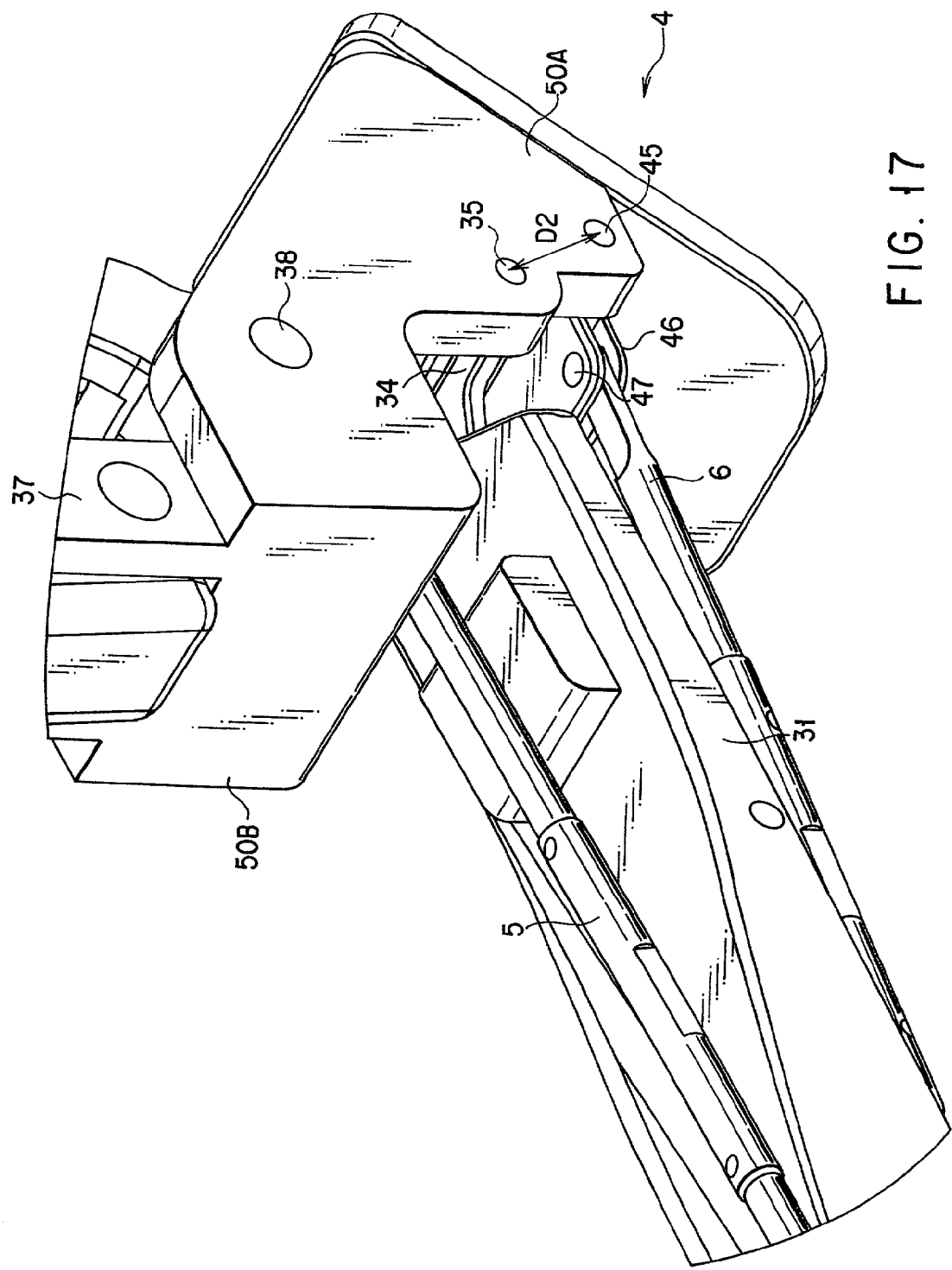
FIG. 17 is a perspective view when a manipulating section of a surgical instrument according to second and third embodiments of the present invention is seen from the top.
Figure 18:
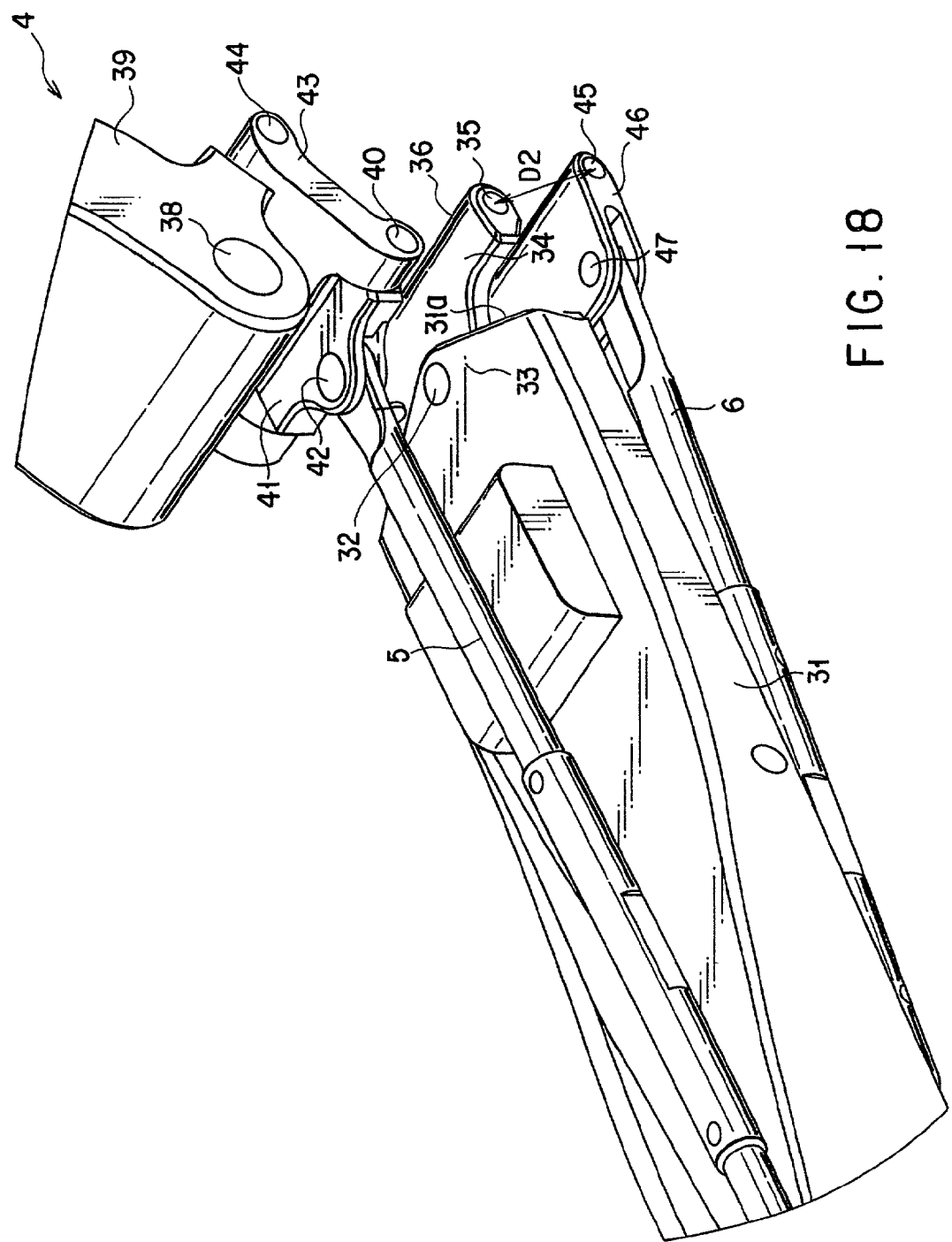
FIG. 18 is a perspective view when a manipulating section of the surgical instrument according to the second and third embodiments of the present invention is seen from the top while the cover is removed.
Figure 19:
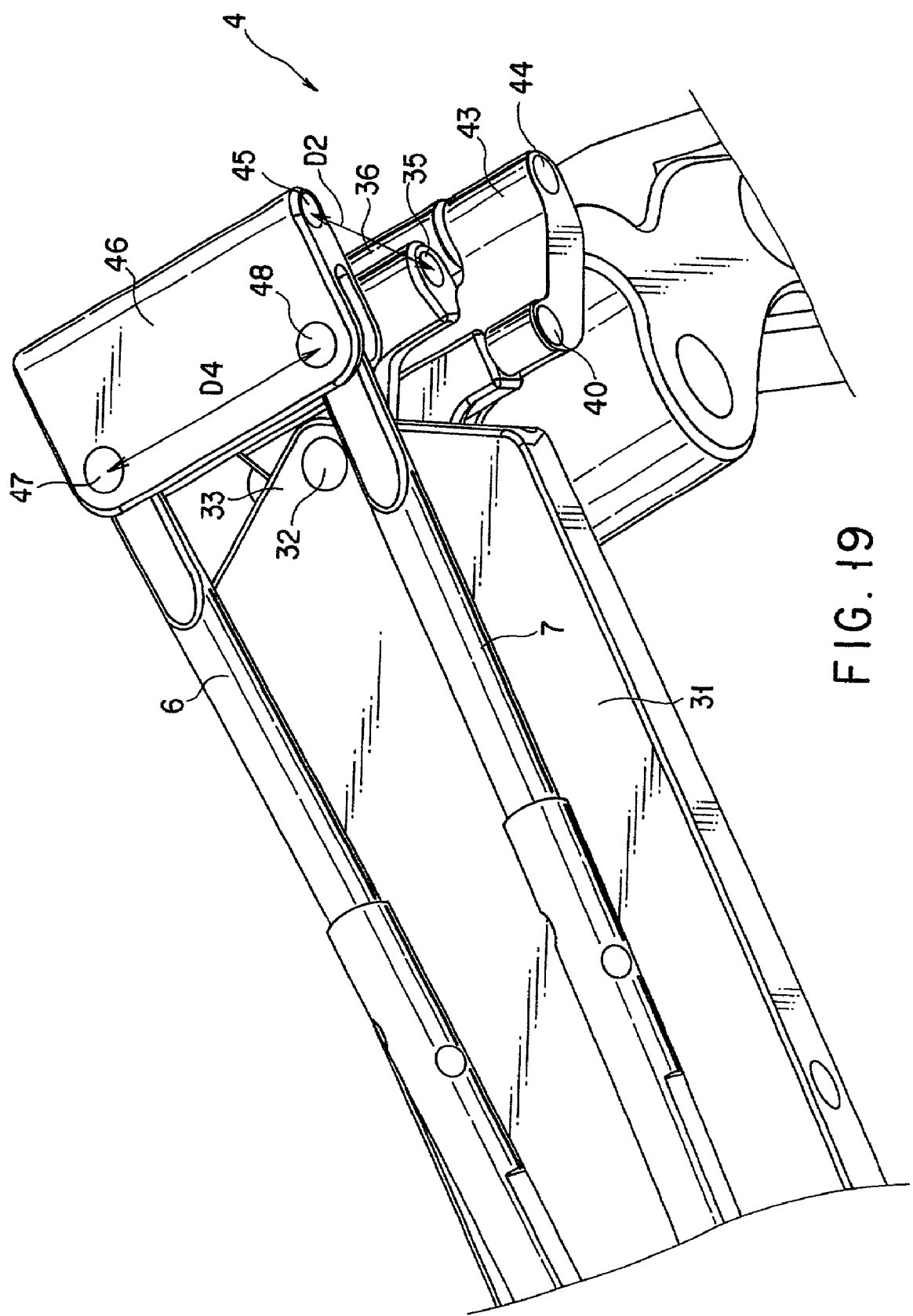
FIG. 19 is a perspective view when the manipulating section of the surgical instrument according to the second and third embodiments of the present invention is seen from the bottom when the cover is removed.

A description of a manipulating section 4 according to the present embodiment will be given here. As shown in FIG. 17 and FIG. 18, even in a proximal end section of the insert section 2, a first drive rod (long side link) 5 is disposed eccentrically upwardly of the axial center of the insert section 2. As shown in FIG. 19, the second and third drive rods (long side links) 6 and 7 are disposed in a transversely symmetrical manner downwardly of the axial center of the insert section 2. As shown in FIG. 17 to FIG. 19, a support section (long side link) 31 protruded backwardly and having rigidity is provided at the proximal end section of the insert section 2. As shown in FIG. 18 and FIG. 19, a first pivot section 33 having a second pivot shaft 32 is provided in the vertical direction of this support section 31, and a third turn plate 34 is provided turnably in the transverse direction at this first pivot section 33.

As shown in FIG. 17, a second pivot section 36 having a third pivot pin 35 is provided in the transverse direction at this third turn plate 34, and a first handle 37 serving as a first manipulating body is articulably provided in the vertical direction at this second pivot section 36. At this first handle 37, a second handle 39 serving as a second manipulating body is turnably provided in the vertical direction by means of a second opening/closing pivot pin 38.

Further, as shown in FIG. 18, a fourth connecting pin 42 is provided in the vertical direction at the proximal end section of the first drive rod 5, and a third connecting member 41 is connected to this connecting pin 42 turnably in the transverse direction. A fifth connecting pin 40 is provided at this third connecting member 41 in the transverse direction, and one end of the fourth connecting member 43 is turnably connected to this connecting pin 40 in the vertical direction. The other end of this fourth connecting member 43 is turnably connected in the vertical direction to the sixth connecting pin 44 provided in the transverse direction at the second handle 39.

A fourth pivot pin 45 is provided in the transverse direction downwardly of the third pivot pin 35 of the first handle 37, and one end of the fourth turn plate 46 is articulably connected to this fourth pivot pin 45 in the vertical direction. As shown in FIG. 19, third and fourth turn pins 47 and 48 are provided in the vertical direction at both right and left ends of the other end section of the fourth turn plate 46. The proximal end sections of the second and third drive rods 6 and 7 are connected to these third and fourth turn pins 47 and 48 respectively.

Therefore, the first and second handles 37 and 39 can be articulated in the transverse direction relative to the support section 31 provided at the proximal end section of the insert section 2 around the second pivot shaft 32. These handles are articulably provided in the vertical direction around the third pivot pin 35. Further, as shown in FIG. 17, the pivot section periphery of the second handle 39 is covered with the covers 50A and 50B that are a part of the first handle 37.

Further, as shown in FIG. 3 and FIG. 19, an intra-axial distance $D_1$ between a first pivot pin 11 and a second pivot pin 20 provided between the insert section 2 and tool section 3 of the surgical instrument 1 is formed to be shorter than an intra-axial distance $D_2$ between a third pivot pin 35 and a fourth pivot pin 45 provided between the insert section 2 and manipulating section 4 ($D_1 < D_2$). Here, these intra-axial distances $D_1$ and $D_2$ are configured to obtain a relationship of $D_1/D_2 \approx 0.541$, for example.

Similarly, an intra-axial direction $D_3$ between the first turn pin 22 and the second turn pin 23 at the tool section 3 of the surgical instrument 1 is formed to be shorter than an intra-axial distance $D_4$ between a third turn pin 47 and a fourth turn pin 48 at the manipulating section 4 ($D_3 < D_4$). Here, these intra-axial distance $D_3$ and $D_4$ are configured to obtain a relationship of $D_3/D_4 \approx 0.577$, for example.

If the first and second handles 37 and 39 are articulated in the vertical direction at the proximal end section of the insert section 2, the first to third drive rods 5, 6, and 7 are advanced forwardly or backwardly, and the first and second tool pieces 12 and 14 are articulated in the vertical direction. Here, the drive rods 5, 6, and 7 each are restricted with mutual intervals by a first support section (long side link) 8 and a second support section 31. A parallel relationship is always maintained at these intervals.

Figure 20:
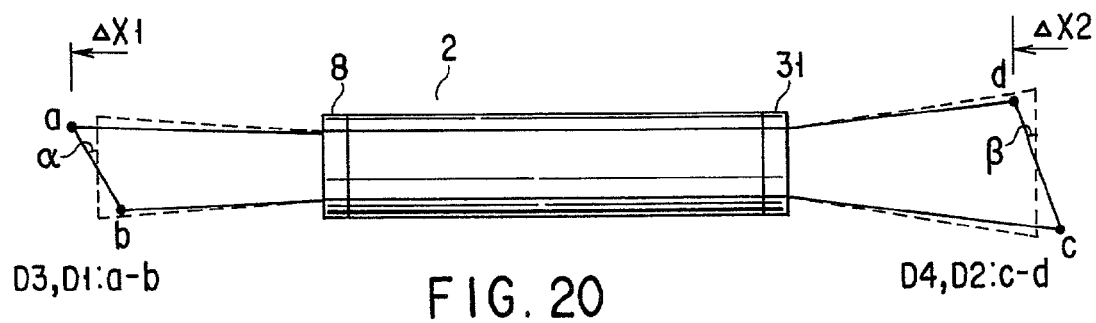
FIG. 20 is a schematic view showing a parallelism shaped link for connecting the tool section and manipulating section of the surgical instrument according to the second and third embodiments of the present invention.

As shown in FIG. 20, rectangle-shaped links in which first to fourth pivot pins 11, 20, 35, and 45 correspond to points "a", "b", "d", and "c" in FIG. 20 respectively, are turned in the vertical direction. Similarly, rectangle-shaped links in which first to fourth turn pins 22, 23, 47, and 48 correspond to points "a", "b", "d", and "c" in FIG. 20 are turned in the transverse direction.

At this time, the previously-described intra-axial distances $D_1$ and $D_2$ are obtained as a relationship of $D_1/D_2 \approx 0.541$, and the intra-axial distance $D_3$ and $D_4$ are obtained as a relationship of $D_3/D_4 \approx 0.577$. When a distance between points "a" and "d" in FIG. 20 is equal to a distance between points "b" and "c", a movement quantity $\Delta X_2$ of point "d" at the manipulating section 4 and a movement quantity $\Delta X_1$ of point "a" at the tool section 3 can be expressed as:

$\Delta X_2 = (D_2/2) \cdot \sin \beta_1$, or alternatively, $\Delta X_2 = (D_4/2) \cdot \sin \beta_2$, $\Delta X_1 = (D_1/2) \cdot \sin \alpha_1$, or alternatively, $\Delta X_1 = (D_3/2) \cdot \sin \alpha_2$.

In an arbitrary posture, $\Delta X_1 = \Delta X_2$ is met, and the movement quantity can be expressed as:

$D_1/D_2 = \sin \beta_1/\sin \alpha_1$ ($=R_1$)

$D_3/D_4 = \sin \beta_2/\sin \alpha_2$ ($=R_2$).

R ($R_1$, $R_2$) denotes a ratio in length of a short side at the tool section 3 of a rectangular link and a short side at the manipulating section 4. Assuming that this ratio $R_1$ is 0.541, for example, as described above, a relationship of a response angle (articulation angle) $\alpha_1 \approx 45$ degrees of the tool section 3 relative to an input angle (articulation angle) $\beta_1 \approx 22.5$ degrees of an input angle (articulation angle) of the manipulating section 4 is obtained. This relationship is indicated by a slid line in FIG. 21.

Figure 22:
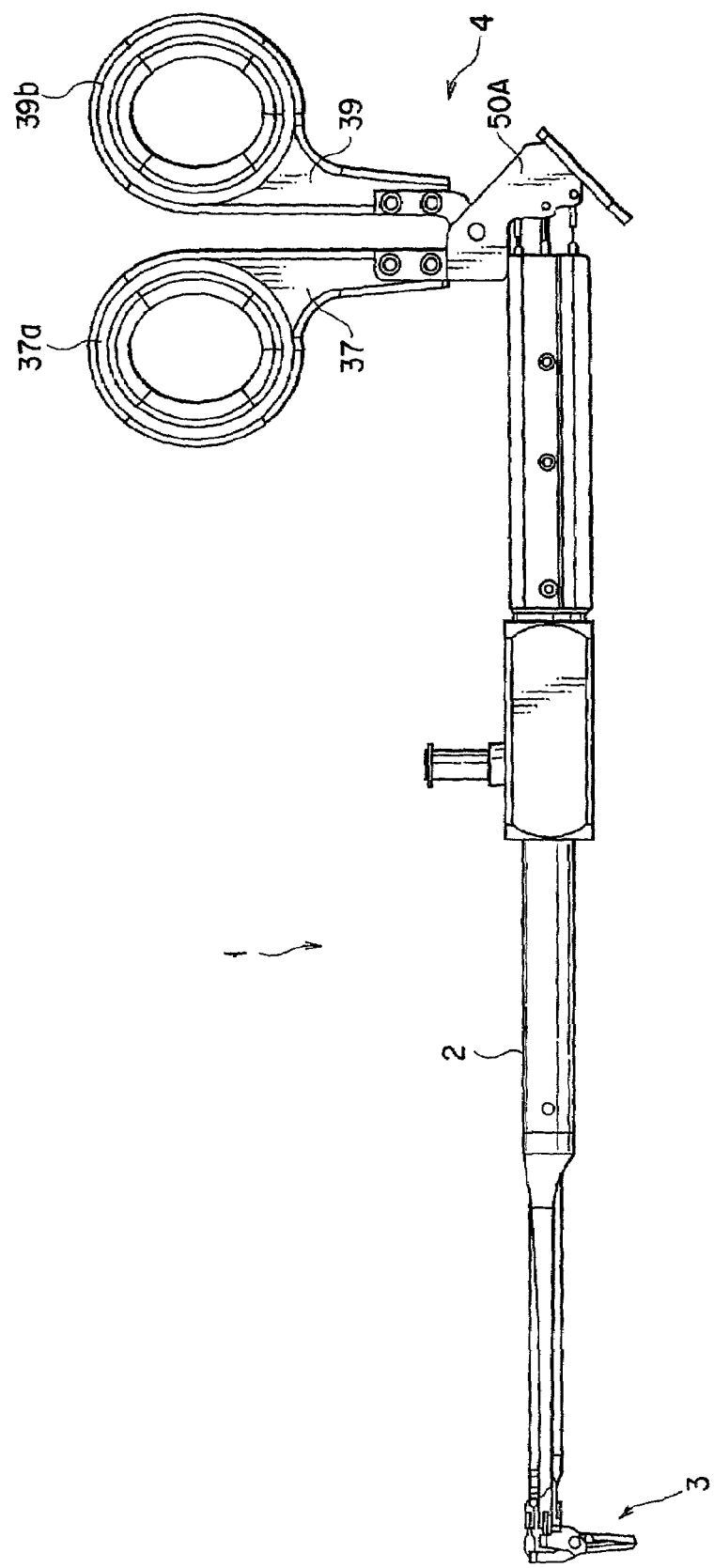
FIG. 22 is a side view showing the surgical instrument according to the second and third embodiments of the present invention while the tool section is lowered downwardly.
Figure 23:
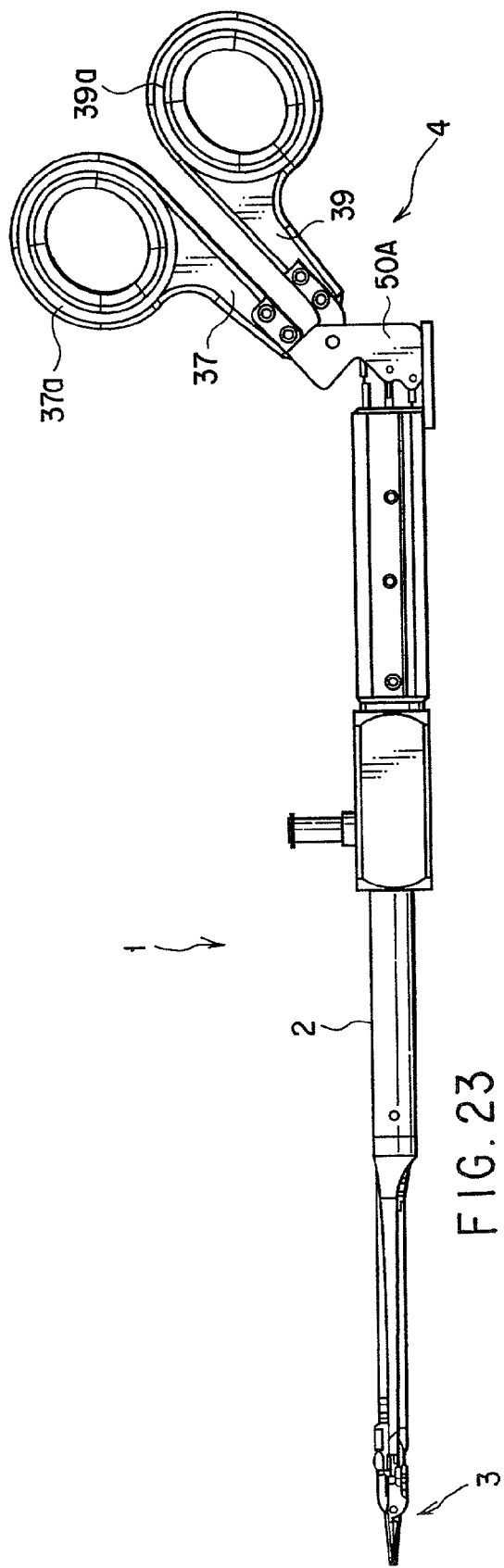
FIG. 23 is a side view showing the surgical instrument according to the second and third embodiments of the present invention while the tool section is placed horizontally.
Figure 24:
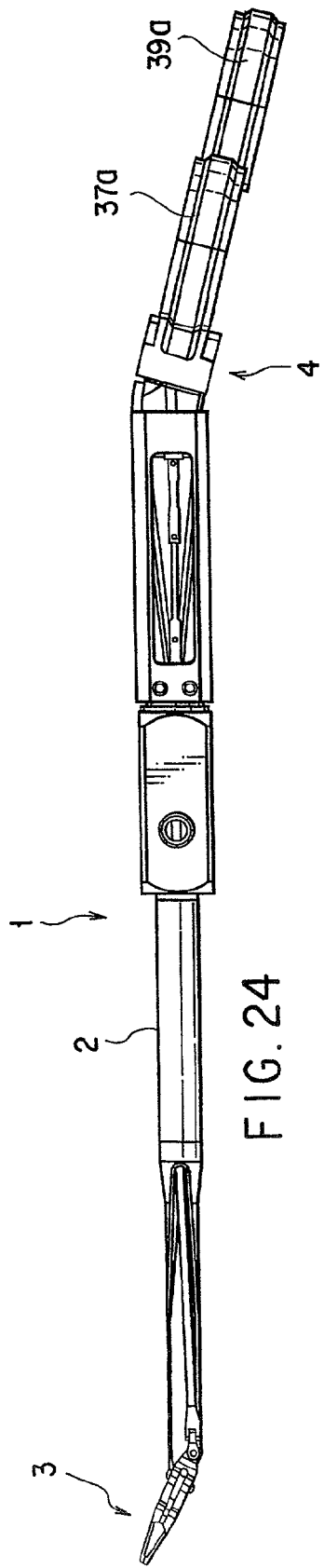
FIG. 24 is a top view showing the surgical instrument according to the second and third embodiments of the present invention while the tool section is articulated transversely.

Considering this fact in an actual manipulation, as shown in FIG. 22, when the manipulating section 4 is inclined upwardly by substantially 90 degrees relative to the axial direction of the insert section 2, the tool section 3 is articulated downwardly by 90 degrees relative to the axial direction of the insert section 2. As shown in FIG. 23, when the manipulating section 4 (first and second handles 37 and 39) is inclined upwardly by substantially 45 degrees relative to the axial direction of the insert section 2, the tool section 3 is placed in a horizontal state extending in the distal end direction of the insert section 2. The covers 50A and 50B act as stoppers for holding the tool section 3 at a position horizontal or vertical to the axial direction of the insert section 2.

Namely, while the manipulating section 4 is turned downwardly by 45 degrees from an articulating posture substantially orthogonal to the insert section 2, the tool section 3 is established in a state shown in FIG. 23 in which the tool section is articulated upwardly by 90 degrees from an articulating posture substantially orthogonal to the insert section 2 to a straight posture coinciding with the axial direction of the insert section 2. At the manipulating section 4, 45 degrees from a posture (state shown in FIG. 23) forming 45 degrees in the axial direction of the insert section 2 to a straight state coinciding with the axial direction of the insert section 2 may be formed as its articulation range.

As described above, assuming that the ratio $R_2$ is 0.577, for example, a relationship of a response angle (articulation angle) $\alpha_2 \approx 60$ degrees of the tool section 3 relative to an input angle (articulation angle) $\beta_2 \approx 30$ degrees of the manipulating section 4 is obtained. This relationship is indicated by a single dotted chain line in FIG. 21. Namely, while the manipulating section 4 is articulated by 30 degrees in a transverse direction from an articulating posture inclined in the transverse direction relative to the axial direction of the insert section 2, the tool section 3 is articulated by 60 degrees in the transverse direction. Thus, when the manipulating section 4 is turned by 60 degrees entirely in the transverse direction, the tool section 3 is articulated by 120 degrees entirely in the transverse direction.

Of course, a value of R may be arbitrarily defined as another value meeting R<1 without being limited to the above value. In this case, when the value is set within the range between about 0.5 and 0.7, a practical effect is increased. In a link according to the present embodiment, the effective width $D_2$ of the short side at the manipulating section 4 is not restricted to a diameter of the insert section 2, and thus, a sufficiently large value can be adopted (R is decreased).

Therefore, according to the present embodiment, a distance $D_2$ between the third and fourth pivot pins 35 and 45 at the manipulating section 4 and a distance $D_4$ between the third and fourth turn pins 47 and 48 are formed to be longer than a distance $D_1$ between first and second pivot pins 11 and 20 at the tool section 3 and a distance $D_3$ between first and second turn pins 22 and 23. Thus, with a comparatively simple construction, an articulation quantity of the manipulating section 4 is increased, and can be transmitted as an articulation quantity at the tool section 3. Thus, unnecessary additional parts are eliminated. When the manipulating section 4 is manipulated during tool, thereby making the tool section 3 movable, the feeling of manipulation that manipulation is directly transmitted is not degraded. Thus, a surgical instrument with its excellent operability can be provided. In actual tool, the movement quantity of the surgeon's wrist can be reduced, and fatigue can be reduced.

That is, a ratio between an articulation angle caused by manipulation of the manipulating section 4 and that of the tool section 3 arbitrarily defined by such a manipulation can be defined relative to a plurality of articulating planes. Thus, the surgeon's fatigue and burden are reduced, and a surgical instrument with its excellent operability can be provided.

Figure 21:
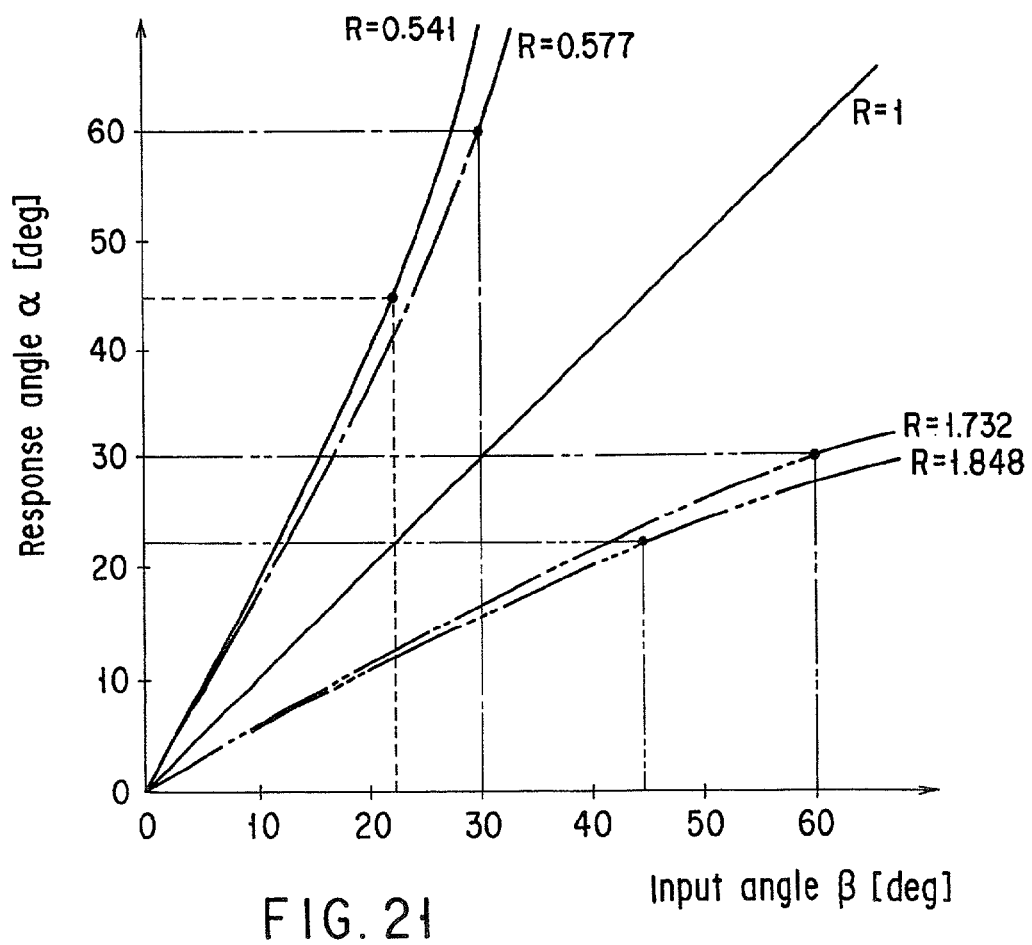
FIG. 21 is a graph depicting a relationship between an articulating angle of the manipulating section and an articulating angle of the tool section of the surgical instrument according to the second and third embodiments of the present invention.

FIG. 20 and FIG. 21 show a third embodiment of the present invention. The present embodiment is directed to a modified example of the second embodiment. Like constituent elements common to those of the second embodiment are designated by like reference numerals. A detailed description is omitted here.

An intra-axial distance $D_1$ between the first pivot pin 11 and the second pivot pin 20 at the tool section 3 of the surgical instrument 1 is formed to be longer than an intra-axial distance $D_2$ between the third pivot pin 35 and the second pivot pin 45 at the manipulating section 4 ($D_1 > D_2$). Here, these intra-axial distances $D_1$ and $D_2$ are configured to obtain a relationship of $D_1/D_2 \approx 1.848$, for example.

Similarly, an intra-axial direction $D_3$ between the first turn pin 22 and the second turn pin 23 at the tool section 3 of the surgical instrument 1 is formed to be longer than an intra-axial distance $D_4$ between a third turn pin 47 and a fourth turn pin 48 at the manipulating section 4 ($D_3 > D_4$). Here, these intra-axial distance $D_3$ and $D_4$ are configured to obtain a relationship of $D_3/D_4 \approx 1.732$, for example.

When the first and second handles 37 and 39 are articulated at the proximal end section of the insert section 2 in the vertical direction, the first to third drive rods 5, 6, and 7 are retracted forwardly or backwardly, and the first and second tool pieces 12 and 14 are articulated in the vertical direction. Here, the drive rods 5, 6, and 7 each are restricted with mutual intervals by means of the first support section 8 and second support section 31, and a parallel relationship is always maintained at these intervals.

As shown in FIG. 20, rectangle-shaped links in which the first to fourth pivot pins 11, 20, 35, and 45 correspond to points "a", "b", "d", and "c" in FIG. 20 respectively are turned in the vertical direction. Similarly, rectangle-shaped links in which the first to fourth turn pins 22, 23, 47, and 48 correspond points "a", "b", "d", and "c" in FIG. 20 respectively are turned in the transverse direction.

At this time, the previously-described intra-axial distances $D_1$ and $D_2$ are defined to obtain a relationship of $D_1/D_2=R_1 \approx 1.848$, and the intra-axial distance $D_3$ and $D_4$ are defined to obtain a relationship of $D_3/D_4=R_2 \approx 1.732$.

When the ratio $R_1$ is defined as 1.848, for example, as described above, a relationship of a response angle (articulation angle) $\alpha 1 \approx 22.5$ degrees of the tool section 3 relative to an input angle (articulation angle) $\beta 1 \approx 45$ degrees of the manipulating section 4 is obtained. This relationship is indicated by a triple dotted chain line in FIG. 21. Namely, while the manipulating section 4 is articulated downwardly by 90 degrees (i.e. 45×2) from a turn posture orthogonal to the axial direction of the insert section 2, the tool section 3 is articulated by about 45 degrees (i.e. 22.5×2) relative to the insert section 2.

When the ratio $R_2$ is defined as 1.732, for example, as described above, a relationship of a response angle (articulation angle) $\alpha 2 \approx 30$ degrees of the tool section 3 relative to an input angle (articulation angle) $\beta 2 \approx 60$ degrees of the manipulating section 4 is obtained. This relationship is indicated by a double dotted chain line in FIG. 21. Namely, while the manipulating section 4 is articulated by 60 degrees in the transverse direction from an articulating posture inclined in the transverse direction relative to the axial direction of the insert section 2, the tool section 3 is articulated by 30 degrees in the transverse direction. Thus, when the manipulating section 4 is articulated by 120 degrees entirely in the transverse direction, the tool section 3 is articulated by 60 degrees entirely in the transverse direction.

Of course, a value of R may be arbitrarily set to another value meeting $R \geq 1$ without being limited to the above value. In this case, when the value is generally set within between 1.5 and 1.9, a practical effect is increased.

Therefore, according to the present embodiment, a distance $D_2$ between the third and fourth pivot pins 35 and 45 at the manipulating section 4 and a distance $D_4$ between the third and fourth turn pins 47 and 48 are formed to be shorter than a distance $D_1$ between the first and second pivot pins 11 and 20 at the tool device 3 and a distance $D_3$ between the first and second turn pins 22 and 23. Thus, with a comparatively simple construction, an articulating quantity of the manipulating section 4 is reduced, and can be transmitted as an articulating quantity at the tool section 3. Therefore, unnecessary parts are eliminated. The manipulating section 4 is manipulated during tool thereby making the tool section movable, and a surgical instrument with its excellent operability can be provided without degrading the feeling of direct manipulation. In actual tool, the tool section 3 can be finely manipulated.

That is, a ratio between a turn angle caused by manipulation of the manipulating section 4 and that of the tool section 3 arbitrarily set by such manipulation can be defined relative to a plurality of articulating planes. Thus, the fatigue and burden of the surgeon are reduced, and a surgical instrument with its excellent operability can be provided. In the second and third embodiments, although a description has been given by assuming that, with the vertical direction and transverse direction, the ratio R is $R<1$ or $R \geq 1$, respectively, the ratio with one of the vertical direction and the transverse direction may be $R<1$ and other ratio may be $R \geq 1$, for example. Alternatively, with both of the vertical direction and the transverse direction, the ratio may be identical to each other.

FIG. 25 to FIG. 29 show a fourth embodiment of the present invention. In the present embodiment, like constituent elements common to those of the previously-described embodiments each are designated by like reference numerals. A duplicate description is omitted here.

In the present embodiment, all constituent elements configuring an articulation link mechanism for articulating (specifically, a mechanism consisting of a link disposed in parallel or in substantially parallel thereto, the link linking the tool section 3 and manipulating section 4, for example) and an opening/closing link mechanism for opening/closing (specifically, a mechanism consisting of a link for linking the tool section 3 and manipulating section 4 in order to open/close the tool section), are formed by a rigid body (for example, a drive rod made of a rigid body). Therefore, strong turn force quantity and opening/closing gripping force can be achieved, and smooth turning manipulation and opening/closing manipulation can be carried out (the required opening/closing gripping force and the feeling of direct manipulation are not degraded).

Figure 27:
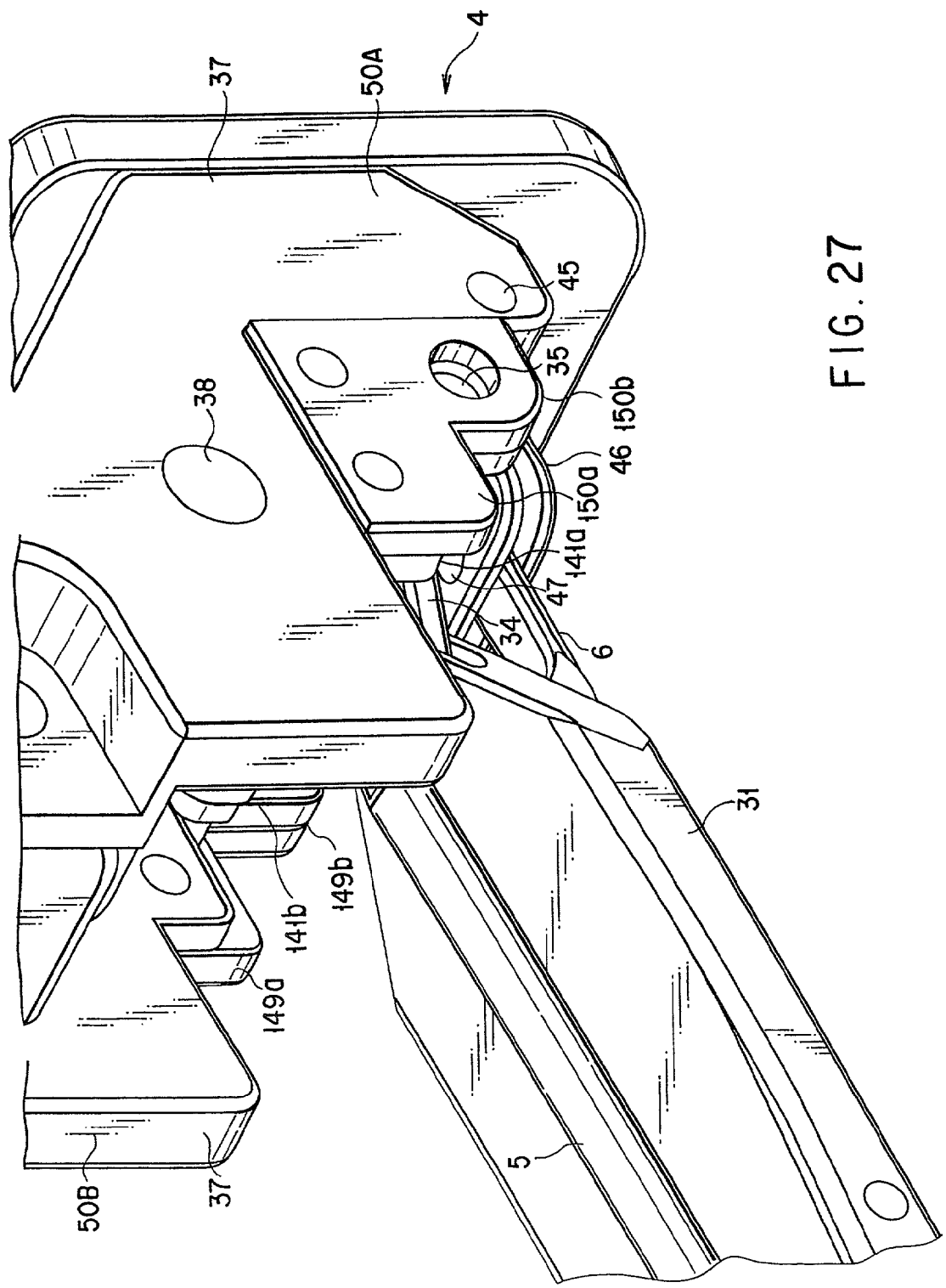
FIG. 27 is a perspective view when the manipulating section of the surgical instrument of FIG. 26 is seen from the top.
Figure 28:
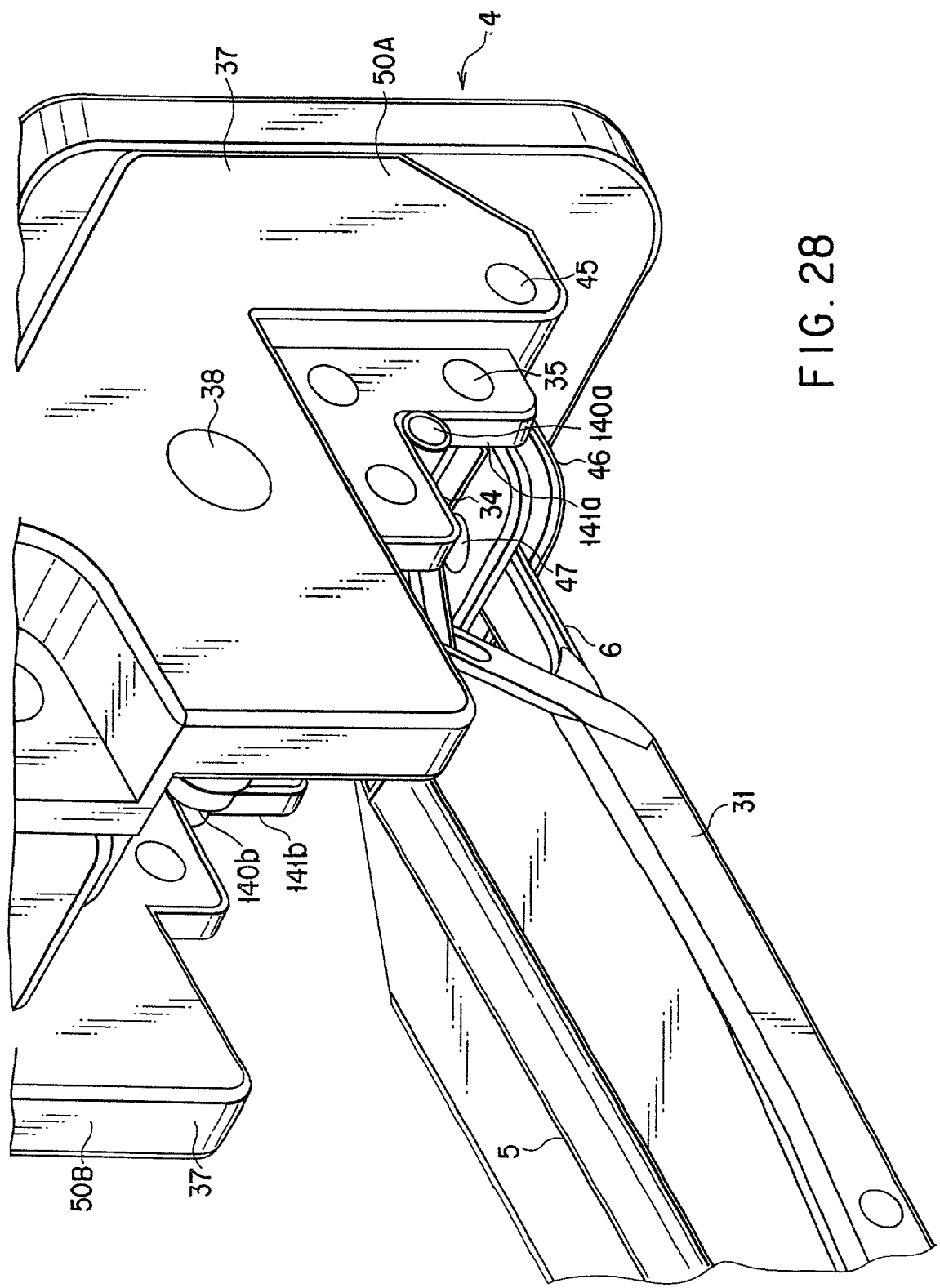
FIG. 28 is a perspective view when the manipulating section of the surgical instrument of FIG. 26 is seen from the top while a cover is partially removed.
Figure 29:
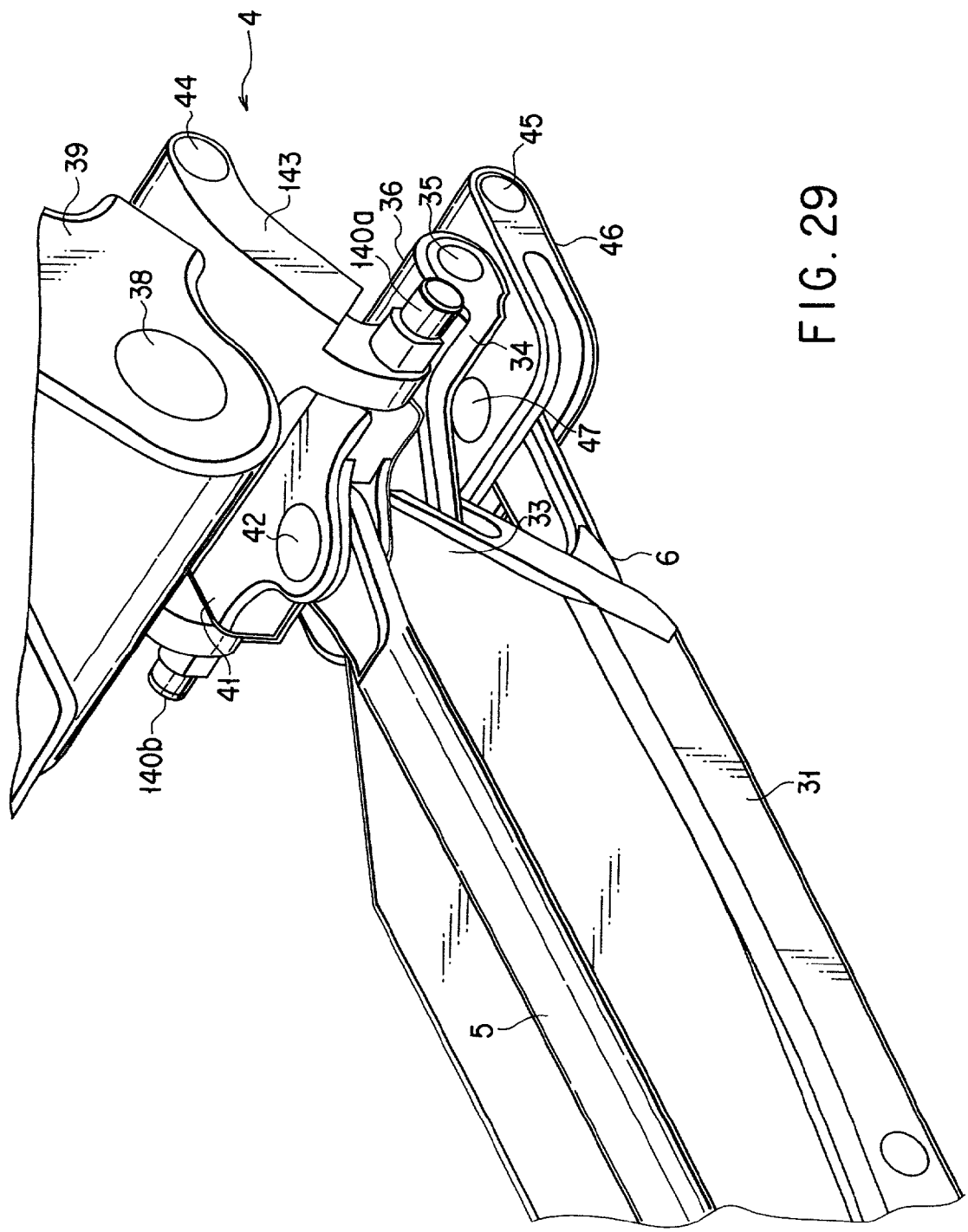
FIG. 29 is a perspective view when the manipulating section of the surgical instrument of FIG. 26 is seen from the top while the cover is fully removed.

In the present embodiment, as shown in FIG. 27 to FIG. 29, the manipulating section 4 is composed of: a connecting member 143 that corresponds to a fourth connecting member 43 of the previously-described embodiments each; pivot shafts 140a and 140b provided at this connecting member 143, the pivot shafts each having a coaxial protrusion section that turnably connects the connecting member 143 to the third connecting member 41 and that protrudes and extends in the transverse direction; pin guide faces 141a and 141b consisting of a plane formed at a part of the covers 50A and 50B of the first handle 37 and abutting against the outer periphery of the protrusion portion of the pivot shafts 140a and 140b; and a cover 149a on the cover 50B installed and the cover 150a on the cover 50A so as to cover these pin guide faces 141a and 141b. The other constituent elements are similar to those of the first embodiment.

Figures 25, 26:
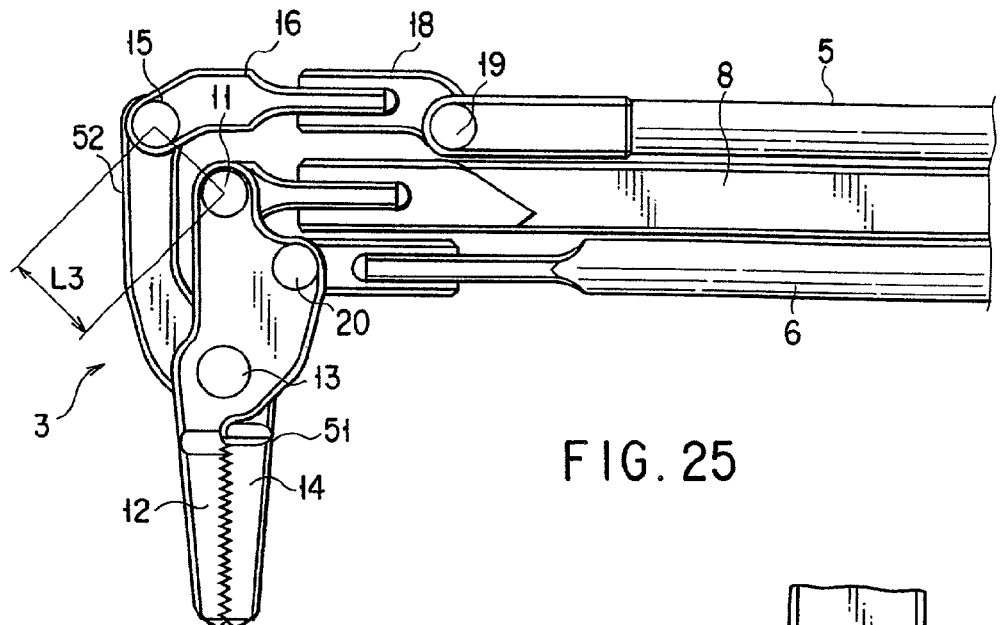
FIG. 25 is a side view showing a tool section of a surgical instrument according to a fourth embodiment of the present invention.
FIG. 26 is a side view showing a manipulating section of the surgical instrument of FIG. 26.

In the meantime, when a comparatively large force is applied when the second handle 39 is turned relative to the first handle 37, thereby closing the handle, the contiguously connecting member 143 is pulled upwardly (upwardly in FIG. 26) in an articulating posture shown in FIG. 26 (that is, in an articulating posture shown in FIG. 12). As a result, the pivot shafts 140a and 140b may be pulled upwardly. In an articulating posture shown in FIG. 10, as a result of the contiguous connecting member 143 being pulled downwardly (downwardly in FIG. 26), the pivot shafts 140a and 140b may be pulled downwardly. In such a case, a position change of the pivot shafts 140a and 140b is provided as a load relative to vertical and transverse articulating manipulations caused by the first handle 37, and smoothness of the articulating manipulation may be lost.

In the present embodiment, as shown in FIG. 26, when the second handle 39 is closed relative to the first handle 37, a distance L4 between the pivot shafts 140a and 140b each (that is, proximal end side joint of opening/closing link) and a third pivot pin 35 (that is, a proximal end side pivot section of turn link) is restricted so as to be constant. Specifically, the outer periphery of the protrusion sections of the pivot shafts 140a and 140b is abutted against the pin guide faces 141a and 141b, and a change in distance L4 is restricted. In the present embodiment, together with such position restriction (restriction of a position change of pivot shafts 140a and 140b), as shown in FIG. 25, a distance L3 between the pivot pin 11 (that is, a distal end side pivot section of articulation link) and a first connecting pin 15 (that is, a distal end side joint of opening/closing link) is set to be equal to a distance L4. That is, in the present embodiment, as long as the second handle 39 is closed relative to the first handle 37, an opening/closing link mechanism from the first connecting pin 15 at the proximal end section of the second tool piece 14 to the pivot shafts 140a and 140b via the first drive rod 5, a turn link mechanism from the third connecting pin 20 at the bent section 12a of the first tool piece 12 to the pivot pin 45 via the second drive rod 6 (and third drive rod 7), and a base mechanism as a basis for the both link mechanisms from the first pivot pin 11 at proximal section of the first tool piece 12 to the pivot pin 35 via the support sections 8 and 31 are disposed to be always in parallel to each other. Therefore, when the pivot shafts 140a and 140b are restricted at proper positions, as described previously, vertical and transverse articulating movement caused by the first handle 37 is smoothly executed.

In this way, according to the present embodiment, with a comparatively simple construction, an opening/closing link can be disposed at a proper position, turning movement of a surgical instrument can be executed smoothly, and operability can be improved.

Figure 30:
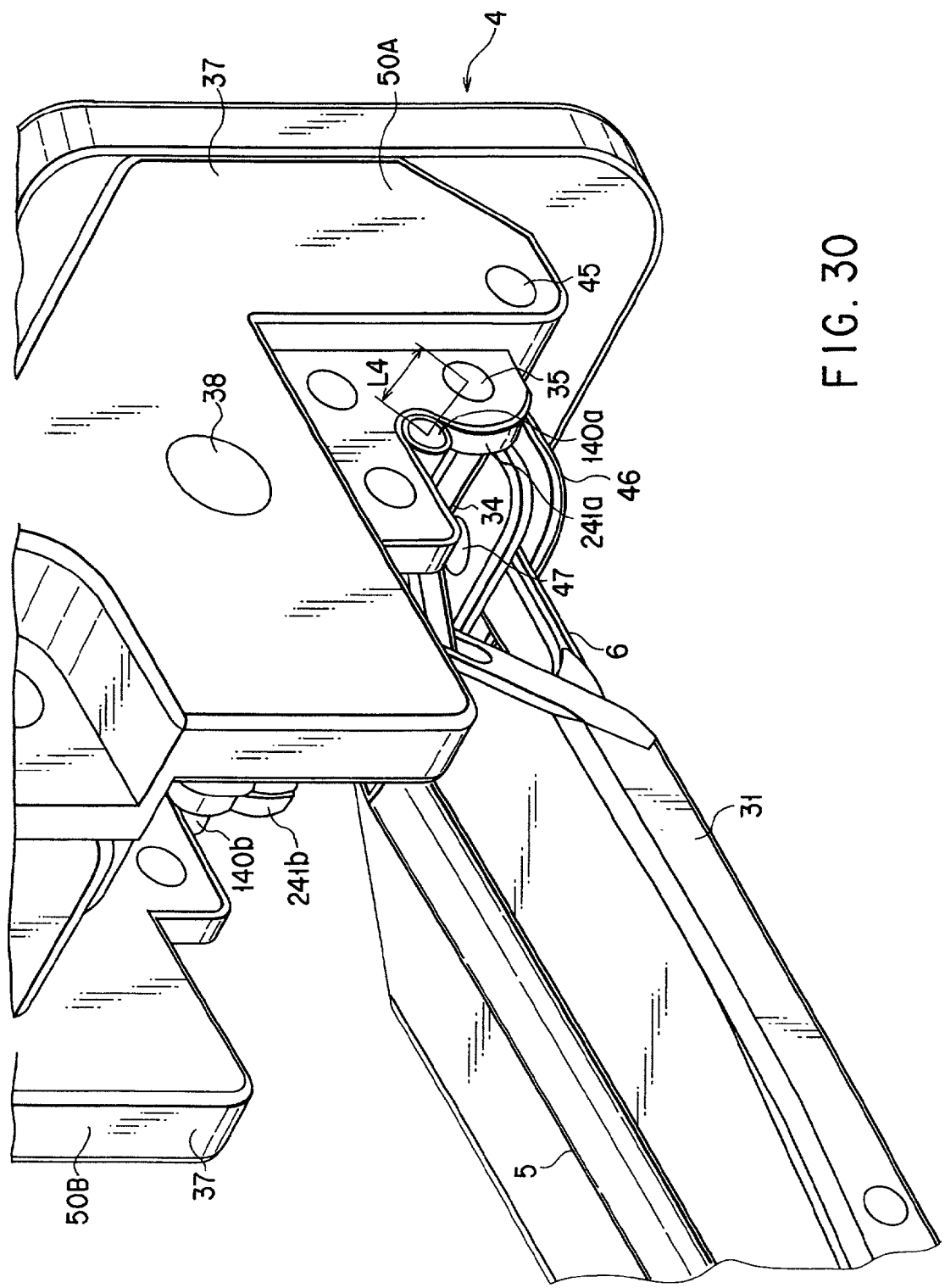
FIG. 30 is a perspective view when a manipulating section of a surgical instrument according to a fifth embodiment of the present invention is seen from the top while the cover is partially removed.
Figure 34:
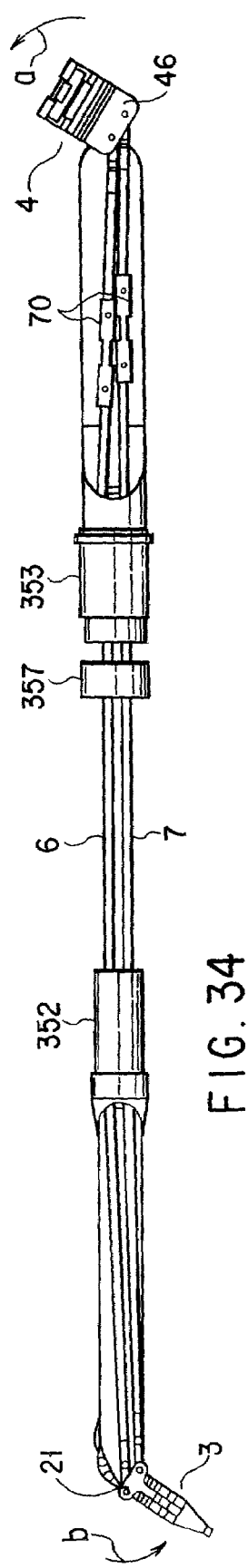
FIG. 34 is a bottom view showing the surgical instrument of FIG. 32A while the tool section is placed horizontally, and is articulated in a transverse direction.
Figure 35:
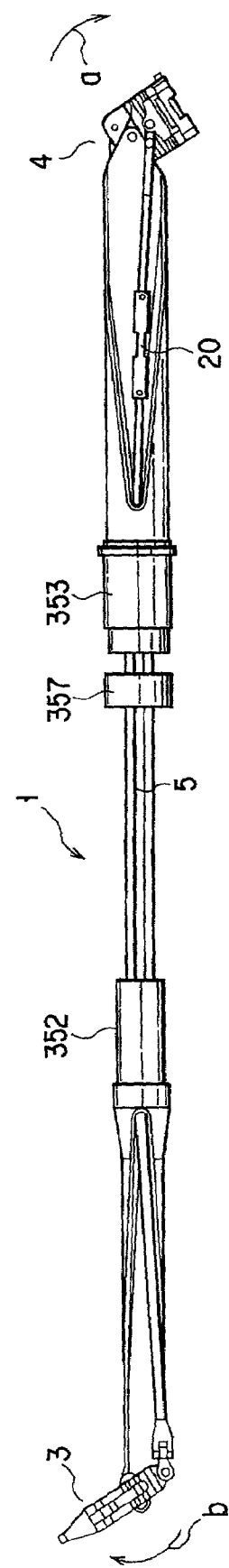
FIG. 35 is a plan view showing the surgical instrument of FIG. 32A while the tool section is placed horizontally, and is articulated in the transverse direction.

FIG. 30 shows a fifth embodiment of the present invention. The present embodiment is directed to a modified example of the fourth embodiment. Constituent elements common to those of the fourth embodiment are designated by like reference numerals. A duplicate description thereof is omitted here.

As shown in FIG. 30, pin guide faces 241a and 241b abutting against the outer periphery of the protrusion portion of the pivot shafts 140a and 140b are formed at a part of the covers SA and 50B. These pin guide faces 241a and 241b are formed as an arc shaped curvature face around the third pivot pin 35. Its radius is set so as to coincide with a distance L4 between the pivot pin 35 and the pivot axes 140a and 140b each. Therefore, the pin guide faces 241a and 241b abut against the outer periphery of the protrusion portion of the pivot shafts 140a and 140b each. In this manner, as long as a position change of the pivot shafts 140a and 140b is restricted, and the second handle 39 is closed relative to the first handle 37, the distance L4 can be maintained constantly. The other constituent elements (for example, L4=L3) is similar to those of the fourth embodiment.

Therefore, in the present embodiment as well, advantageous effect similar to that of the fourth embodiment can be attained.

FIG. 31A and FIG. 31B show a sixth embodiment of the present invention. In the present embodiment, constituent elements common to those of the previously-described embodiments each are designated by like reference numerals. A duplicate description thereof is omitted here.

As shown in FIG. 31A, at the inside of the insert section 2, the proximal end section side of the first drive rod 5 is divided into tow sections, the drive rod 56 at the tool section 3 and the drive rod 57 at the manipulating section 4. A right screw 56a is formed at the end section of these drive rods 56 each, and a left screw 57a is formed at the end section of the drive rod 57. An adjusting member 70 having a screw section at both ends is screwed at the right screw 56a of the drive rod 56 and the left screw 57a of the drive rod 57. The adjusting member 70 is turned clockwise or counterclockwise, whereby a turn buckle capable of adjusting a substantial length of the first drive rod 5 by elongating or shortening a distance between the drive rod 56 and the drive rod 57 is formed.

A D cut 71 engaged with a tool during turning is provided at the intermediate section of the adjusting member 70. An injection port 72 for injecting adhesive or the like after adjusted, thereby locking the adjusting member 70 is provided on the peripheral wall of both ends.

Further, as shown in FIG. 31B, the proximal end section side of the second drive rod 6 and the third drive rod 7 is divided into two sections, a drive rod 58 at the tool section 3 and a drive rod 59 at the manipulating section 4. The right screw 58a is formed at the end section of the drive rod 58, and the left screw 59a is formed at the end section of the drive rod 59. The adjusting member 70 having a screw section at both ends is screwed at the right screw 58a of the drive rod 58 and the left screw 59a of the drive rod 59. The adjusting member 70 is turned clockwise or counterclockwise, whereby a turn buckle capable of adjusting a substantial length of the second drive rod 6 and a third drive rod 7 by elongating or shortening a distance between the drive rod 58 and the drive rod 59 is formed.

A D cut 71 engaged with a tool during turning is provided at the intermediate section of the adjusting member 70, and an injection port 72 for injecting adhesive or the like after adjusted, thereby locking the adjusting member 70 is provided on the peripheral wall of both ends.

When a surgical instrument is assembled, the substantial lengths of the first to third drive rods 5, 6, and 7 each are adjusted by the adjusting member 70, whereby dimensional errors of parts and assembling errors can be corrected by the adjusting member 70. That is, at two articulating postures, i.e., at a first articulating posture at which the tool section 3 and manipulating section 4 substantially form a straight line relative to an axis of the insert section 2 (refer to FIG. 10); and at a second articulating posture at which the tool section 3 and manipulating section 4 are substantially vertical relative to an axis of the insert section 2, the opening/closing angles and turning angles between the tool section 3 and manipulating section 4 can be coincided with each other.

Therefore, the tool section 3 can be articulated in an arbitrary direction by means of a handle manipulation of the manipulating section 4. In addition, the opening/closing angles between the first and second handle 37 and 39 and the tool section 3 can be coincided with each other at least at two articulating postures. In this manner, when the tool section 3 is articulated by articulating movement of the first and second handles 37 and 39, the tool section 3 does not make opening/closing movement.

As has been described above, according to the present embodiment, the opening/closing angles and articulating angles between the manipulating section and tool section are coincided with each other by a turn buckle mechanism at least at two articulating postures. In this manner, the opening/closing angle of the manipulating section in all the articulating postures can be reliably transmitted to that of the tool section, and thus, transmission of the needle gripping force can be made more reliably.

FIG. 32A to FIG. 35 show a seventh embodiment of the present invention. In the present embodiment, constituent elements common to those of the previously-described embodiments each are designated by like reference numerals. A duplicate description thereof is omitted here.

As shown in FIG. 32A to FIG. 32C, a first position restricting member 352 and a second position restricting member 353 serving as position restricting means are provided at the inside of the insert section 2. The first position restricting member 352 is provided at a position which is closer to the tool section 3 than a washing port 55 shown in FIG. 1, and the second position restricting member 353 is provided at a position which is closer to the manipulating section 4 than the washing port 55.

The first and second position restricting members 352 and 353 each have an analogous structure. A description will be given here with respect to the first position restricting member 352. Three through holes 354a, 354b, and 354c are provided to be spaced from each other over the axial direction at a columnar body 54 of the proximal end section of the first position restricting member 352. The first drive rod 5 is movably inserted into the through hole 354a in the axial direction. Second and third drive rods 6 and 7 are movably inserted into the remaining through holes 354b and 354c respectively in the axial direction. Therefore, these first to third drive rods 5, 6, and 7 are retractable in the axial direction between the position restricting means 352 and 353, but are not movable in radial direction of the insert section 2. These rods are restricted so that a relative interval does not change.

Further, between the first position restricting member 352 and the second position restricting member 353, a sealing member 357 serving as sealing means is provided at the internal cavity of the insert section 2 positioned at a position close to the manipulating section 4 than the washing port 55. As shown in FIG. 33, this sealing member 357 is formed in a disk shape consisting of a synthetic resin material having elasticity such as silicon material, for example, and three through holes 357a, 357b, and 357c are provided to be spaced from each other over the axial direction. The first drive rod 5 is inserted into the through hole 357a movably in the axial direction and in a sealed state. The second and third drive rods 6 and 7 are inserted into the remaining through holes 357b and 357c movably in the axial direction respectively and in a sealed state.

Therefore, although these first to third drive rods 5, 6, and 7 are movable in axial direction respectively, these rods are sealed in a closely sealed state by a sealing member 357, and are constructed so that gas or liquid does not leak in the direction of the second position restricting member 353. The sealing member 357 is positioned between the position restricting means 352 and 353, so that these first to third drive rods 5, 6, and 7 do not move in a radial direction. Thus, sealing state is not broken.

Next, working of the above-described construction will be described here.

Although described previously, as shown in FIG. 34 and FIG. 35, if the first and second handles 37 and 39 at the manipulating section 4 are articulated together in a direction indicated by the arrow "a" while in a parallel state around a pivot shaft 32, the second drive rod 6 is advanced along the insert section 2 via the fourth turn plate 46, and the third drive rod 7 is retracted along the insert section 2.

Therefore, a first turn pin 22 at the tool section 3 is advanced, and a second turn pin 23 is retracted. Thus, the second turn plate 21 is articulated around the pivot shaft 9, and the first and second tool pieces 12 and 14 are articulated in a direction indicated by the arrow "b". Conversely, when the first and second handles 37 and 39 are articulated together in a direction reversed from a direction indicated by the arrow "a" around the second pivot shaft 32, the second drive rod 6 is retracted via the fourth turn plate 46, and the third drive rod 7 is advanced.

Therefore, the first turn pin 22 at the tool section 3 is retracted, and the second turn pin 23 is advanced. Thus, the second turn plate 21 is turned around the pivot shaft 9, and the first and second tool pieces 12 and 14 are articulated in a direction reversed from a direction indicated by the arrow "b".

Namely, the first and second tool pieces 12 and 14 are articulated together with articulation of the first and second handles 37 and 39, and the first and second handles 37 and 39 and the first and second tool pieces 12 and 14 are parallel to each other. The orientation of the tool section 3 can be manipulated in an arbitrary direction by the first and second handles 37 and 39.

At this time, the second and third drive rods 6 and 7 are inserted into the through holes 354b and 354c of the first and second position restricting members 352 and 353, and their positions are restricted so that they do not move in the radial direction of the insert section 2. Thus, the second drive rod 6 and the third drive rod 7 move in the radial direction of the insert section 2 between the first position restricting member 352 and the second turn pate 21. Further, these first to third drive rods 5, 6, and 7 are sealed in a closely sealed state by the sealing member 357, and gas or liquid does not leak in the direction of the second position restricting member 353. Therefore, a washing liquid is injected from the washing port 55, whereby the internal of the insert section 2 can be washed.

As has been described above, according to the present embodiment, position restricting means for restricting mutual intervals of the drive rods is provided at an insert section, whereby the insert section is restricted to be small in diameter, and an operational error of a link mechanism can be prevented. An articulating manipulation of a manipulating section can be reliably transmitted to an articulating movement of a tool section.

FIG. 36A to FIG. 38 show an eighth embodiment of the present invention. In the present embodiment, constituent elements common to those of the previously-described embodiments each are designated by like reference numerals. A duplicate description thereof is omitted here.

Figure 36A:
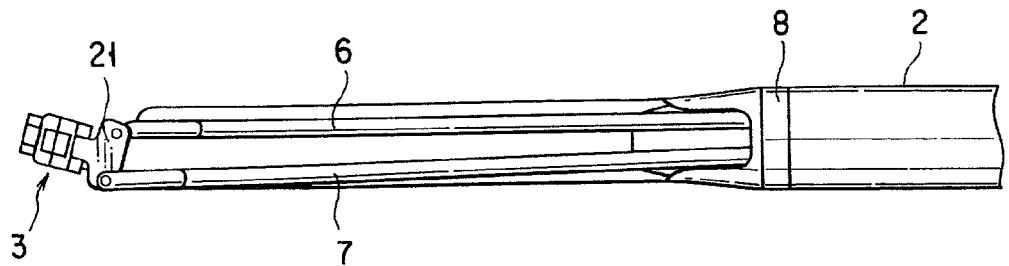
FIG. 36A is a general bottom view showing a distal end section of an insert section when a line segment connecting two pivot axis/axel (a third turn pin and a fourth turn pin) provided at a fourth turn plate shown in FIG. 6 and second and third drive rods are orthogonal to each other at a proximal end section of an insert section of a surgical instrument according to an eighth embodiment of the present invention.
Figure 36B:
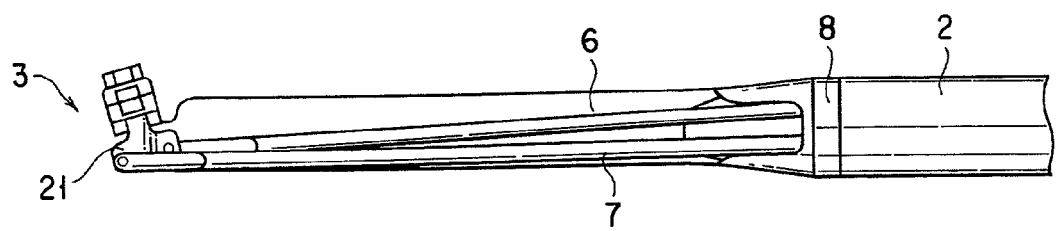
FIG. 36B is a general bottom view showing the distal end section of the insert section when a first handle is articulated in a clockwise direction.
Figure 36C:
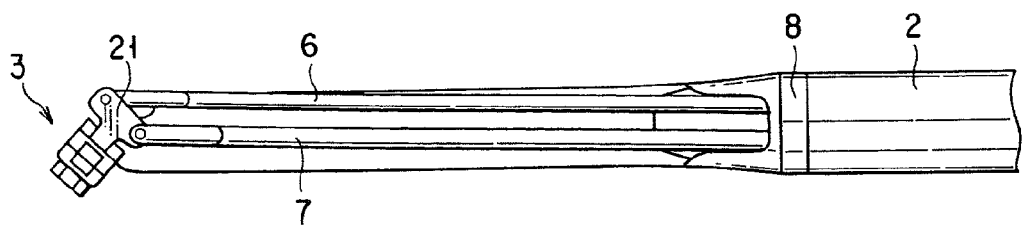
FIG. 36C is a general bottom view showing the distal end section of the insert section when the first handle is articulated in a counterclockwise direction.

As shown in FIG. 36A to FIG. 36C, in the present embodiment, a length of a third drive rod 7 is different from that of a second drive rod 6. Specifically, the length of the third drive rod 7 is formed to be longer than that of the second drive rod 6. With such a construction, as shown in FIG. 6, when a side connecting the center of the turn pins 47 and 48 provided at the fourth turn plate 46 and the second and third drive rods 6 and 7 are placed in a normal state which is perpendicular or substantially perpendicular to each other, as shown in FIG. 36A, the tool section 3 is established in a state deflected in the counterclockwise direction relative to the axial direction of the insert section 2 (FIG. 36 is a bottom view), namely, in an articulated state.

When the first handle 37 shown in FIG. 1 is articulated in the counterclockwise or clockwise direction, as shown in FIG. 36B and FIG. 36C, the tool section 3 is articulated in the counterclockwise direction and clockwise direction, respectively. As long as the deflection angle of the second turn plate 21 relative to the second and third drive rods 6 and 7 in a normal state shown in FIG. 36A is within the range between about 10 degrees and about 15 degrees relative to the axial direction of the insert section 2, the articulation range in the transverse direction of the tool section 3 can be assured up to about 120 degrees to 130 degrees. Assuming that the deflection angle in the normal state is defined as about 30 degrees, the articulation range in the transverse direction is restricted to the range of about 100 to 110 degrees. Thus, it is desirable that the deflection angle in the normal state be within the range of about 10 degrees and 15 degrees.

Figure 37:
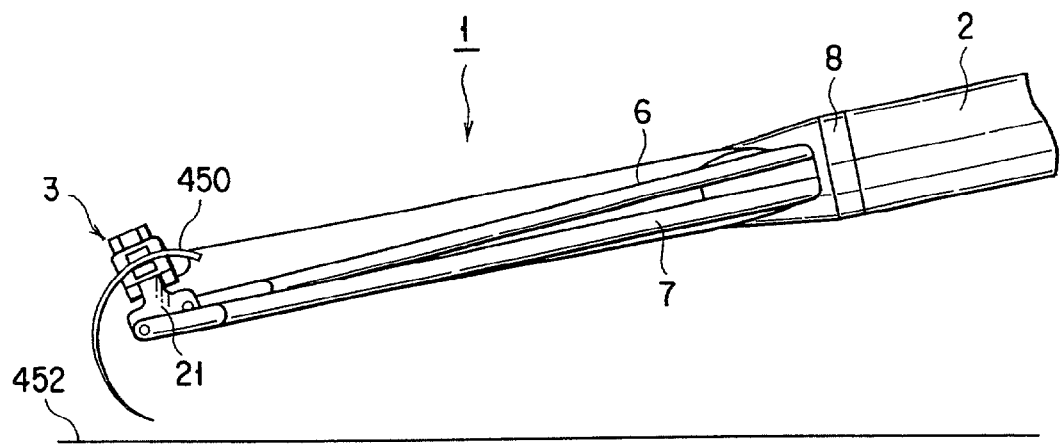
FIG. 37 is general schematic view when a suture needle is gripped at a tool section of a surgical instrument shown in FIG. 36A to FIG. 36C, and is oriented to a suture target.
Figure 38:
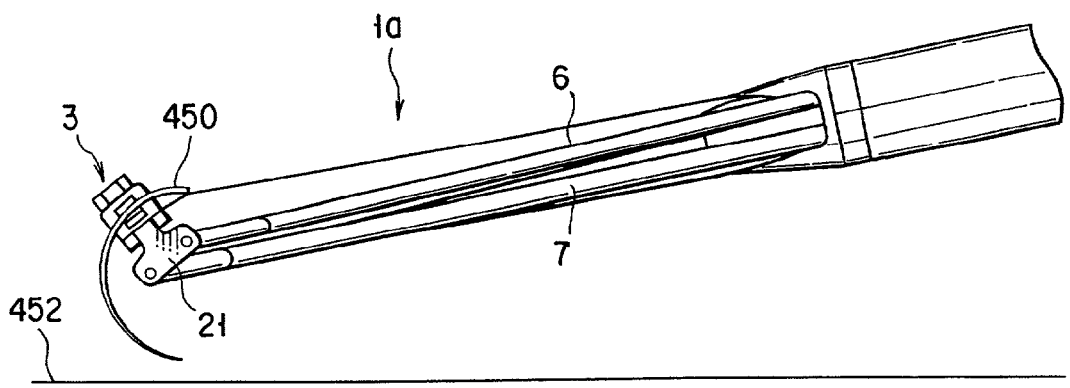
FIG. 38 is a general schematic view when a suture needle is gripped at the tool section of the surgical instrument according to the first embodiment, and is oriented to a suture target.

Further, as shown in FIG. 37, when a suture needle 450 is gripped at the tool section 3, the puncture angle relative to a suture target 452 can be increased as compared with that of the first embodiment shown in FIG. 38. In addition, the articulating angle in the transverse direction is assured up to about 120 degrees, and thus, an articulating stroke in which a target of the suture needle 450 can be sufficiently protruded from the suture target 452 is assured. In addition, it is preferable that the surgical instrument 1 according to the present embodiment be held by right hand. Therefore, according to the present embodiment, the lengths of the second and third drive rods 6 and 7 are differentiated from each other, whereby the puncture angle of the suture needle can be increased with a comparatively simple construction. In the case of actual use, operability can be improved.

Figure 39:
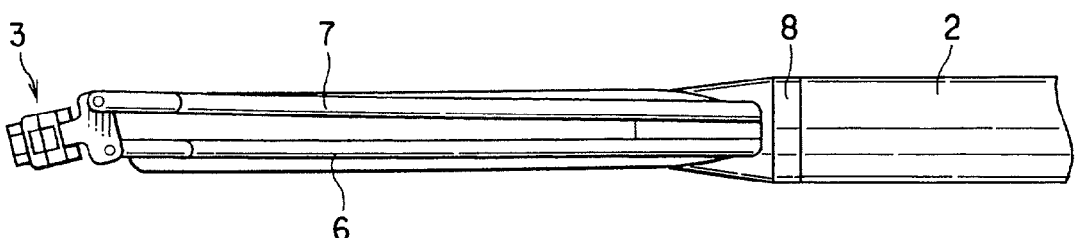
FIG. 39 is a general bottom view showing a distal end section of an insert section when a line segment connecting two pivot axis/axel (a third turn pin and a fourth turn pin) provided at a fourth turn plate shown in FIG. 6 and second and third drive rods are orthogonal to each other at a proximal end section of an insert section of a surgical instrument according to a ninth embodiment of the present invention.

FIG. 39 shows a ninth embodiment of the present invention. The present embodiment is directed to a modified example of the eighth embodiment. Like elements identical to those used in the eighth embodiment are designated by like reference numerals. A detailed description thereof is omitted here.

In the surgical instrument 1, the first and second drive rods 6 and 7 described in the eight embodiment are arranged at positions opposite to each other. That is, in the normal state shown in FIG. 6, as shown in FIG. 3, the second drive rod 6 is arranged at the right side toward the distal end direction of the insert section 2. The third drive rod 7 is arranged at the left side toward the distal end direction of the insert section 2 (FIG. 39 is a bottom view). Thus, it is preferable that the surgical instrument 1 according to the present embodiment be held by left hand. Therefore, according to the present embodiment, as in the eighth embodiment, the puncture angle of the suture needle can be increased with a comparatively simple construction. In actual use, operability can be improved.

In these eighth and ninth embodiments, although a description has been given with respect to tool of puncturing a suture needle into a suture target, these two embodiments can be carried out for a variety of tools without being limited to such tool. That is, although a description has been given with respect to a case in which a tool section is deflected in a predetermined direction, thereby making it possible to easily puncture the suture needle, the suture needle can be used to be deflected in a direction in which the needle is hardly punctured. In these eighth and ninth embodiments, although the articulating angle of the tool section 3 has been defined as about 120 degrees to 130 degrees, a variety of articulation ranges can be defined depending on the design conditions without being limited to such an angle.

Figure 40:
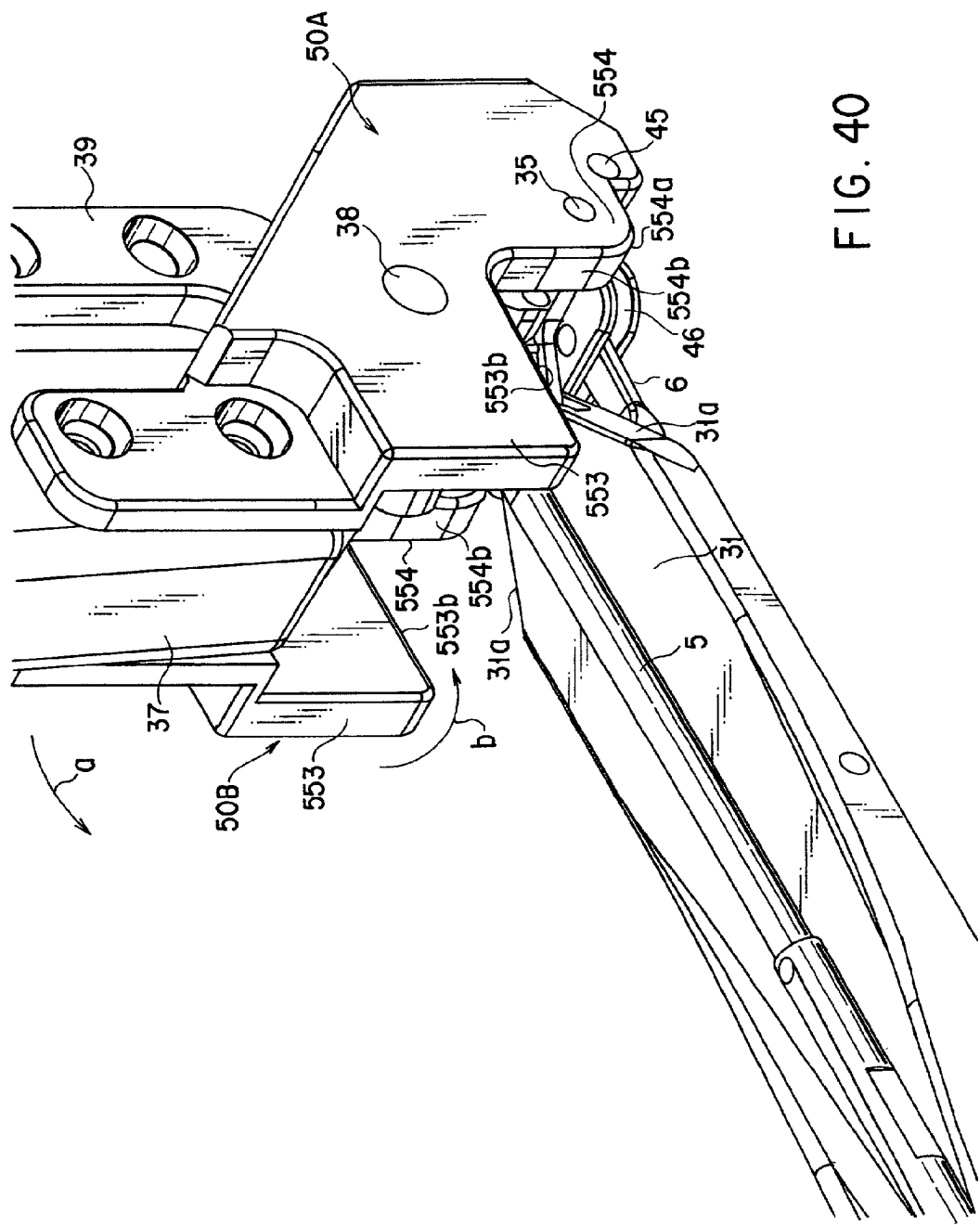
FIG. 40 is a perspective view showing a manipulating section of a surgical instrument according to a tenth embodiment of the present invention.
Figure 41:
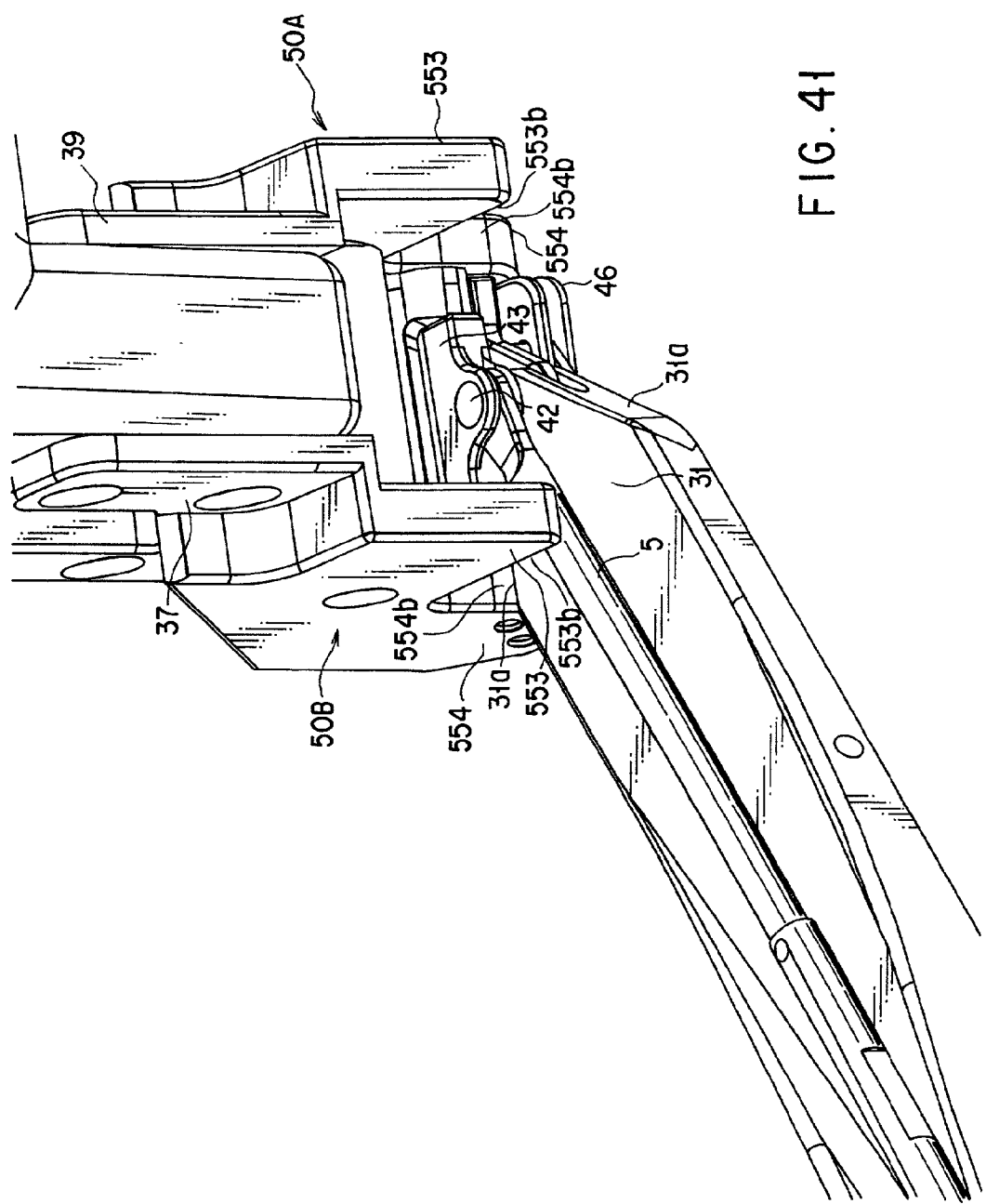
FIG. 41 is a perspective view showing the manipulating section of FIG. 40 while the articulating in a transverse direction is restricted.

FIG. 40 and FIG. 41 show a tenth embodiment of the present invention. In the present embodiment, constituent elements common to those of the previously-described embodiments each are designated by like reference numerals. A duplicate description thereof is omitted here.

Like the previously-described embodiments each, in the present embodiment as well, as shown in FIG. 40 and FIG. 41, a first cover member 50A and a second cover member 50B for covering a link or the like such as a third turn plate 34 and a fourth turn plate 46 are fixed to the proximal end section of the first handle 37 at the periphery of the pivot section of the first handle 37 and second handle 39. In the present embodiment, the first and second cover members 50A and 50B comprise: a first protrusion portion 553 that has a lower face 553b and protrudes toward the distal end direction of the insert section 2 from a second opening/closing pivot pin 38 when the first handle 37 is articulated at a right angle relative to the axle of the insert section 2; and a second protrusion portion 554 that protrudes downwardly of the second opening/closing pivot pin 38 and that has an arc shaped section 554a around the third pivot pin 35 and a front face 554b.

The arc shaped section 554a of the second protrusion portion 554 is formed at a curvature around the third pivot pin 35. Thus, within the articulation range in which the first handle 37 is articulated in the vertical direction, the articulated range in the transverse direction of the third pivot pin 35 is restricted to be always a constant distance by the abutment receiving face 31a of the support section 31.

Accordingly, the articulation range in the transverse direction of the first handle 37 is restricted constantly relative to that in the vertical direction of the first handle 37. That is, the first and second cover members 50A and 50B and the abutment receiving face 31a of the support section 31 are cooperated, thereby configuring restricting means.

As described previously, the articulation range in which the first and second handles 37 and 39 are articulated in the vertical direction around the third pivot pin 35 is within the range of substantial 90 degrees between a position horizontal to the axle of the insert section 2 and a position at which the first and second handles 37 and 39 are vertical to the axle of the insert section 2 as shown in FIG. 40.

In the state shown in FIG. 40, if the first and second handles 37 and 39 are articulated in a transverse direction, for example, in a direction indicated by the arrow "b" around the second pivot shaft 32, as shown in FIG. 41, the front face 554b of a second protrusion portion 554 of the first cover member 50B abuts against the abutment receiving face 31a of the support section 31. Therefore, even if an attempt is made to excessively turn the first and second handles 37 and 39 in a direction indicated by the arrow "b" over the limitation of their turning, their articulation range is restricted. If the first and second handles 37 and 39 are articulated in a direction reversed from a direction indicated by the arrow "b" around the second pivot shaft 32, a front face 554b of the second protrusion portion 554 of the second cover member 50B abuts against the abutment receiving face 31a of the support section 31. Thus, the articulation range in the transverse direction of the first and second handles 37 and 39 is restricted.

Therefore, when the first and second handles 37 and 39 at the manipulating section 4 articulated in the transverse direction around the second pivot shaft 32, thereby making the tool section 3 straight in the extension direction of the insert section 2 or providing an angle relative to the insert section 2, even if an attempt is made to move the first and second handles 37 and 39 in excess of the articulation range, the articulation range is restricted by the first and second cover members 50A and 50B and the abutment receiving face 31a of the support section 31. Thus, damage of the manipulating section 4 can be prevented.

Figure 42:
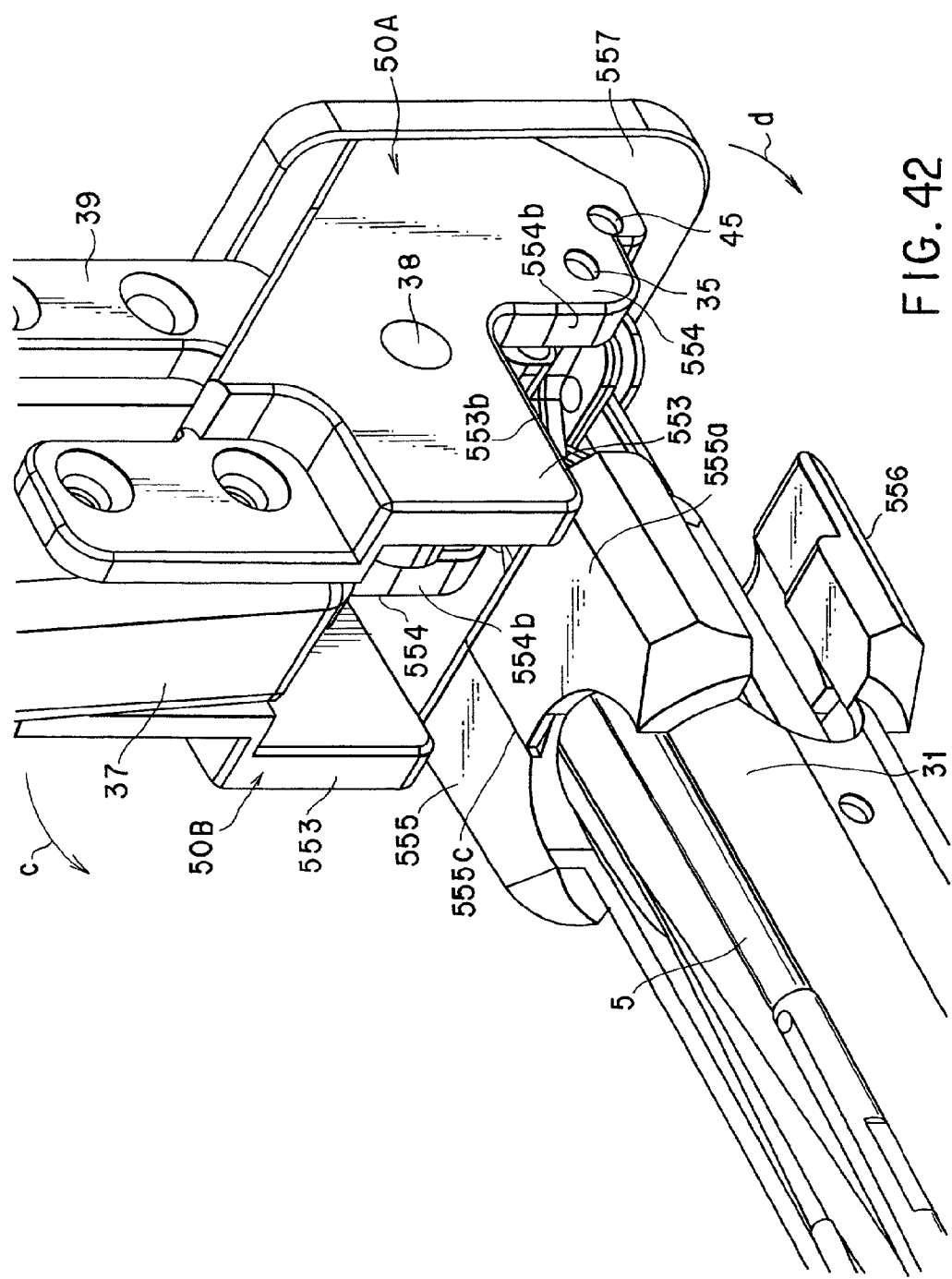
FIG. 42 is a perspective view showing a manipulating section of a surgical instrument according to an eleventh embodiment while the articulating in a vertical direction is restricted.
Figure 43:
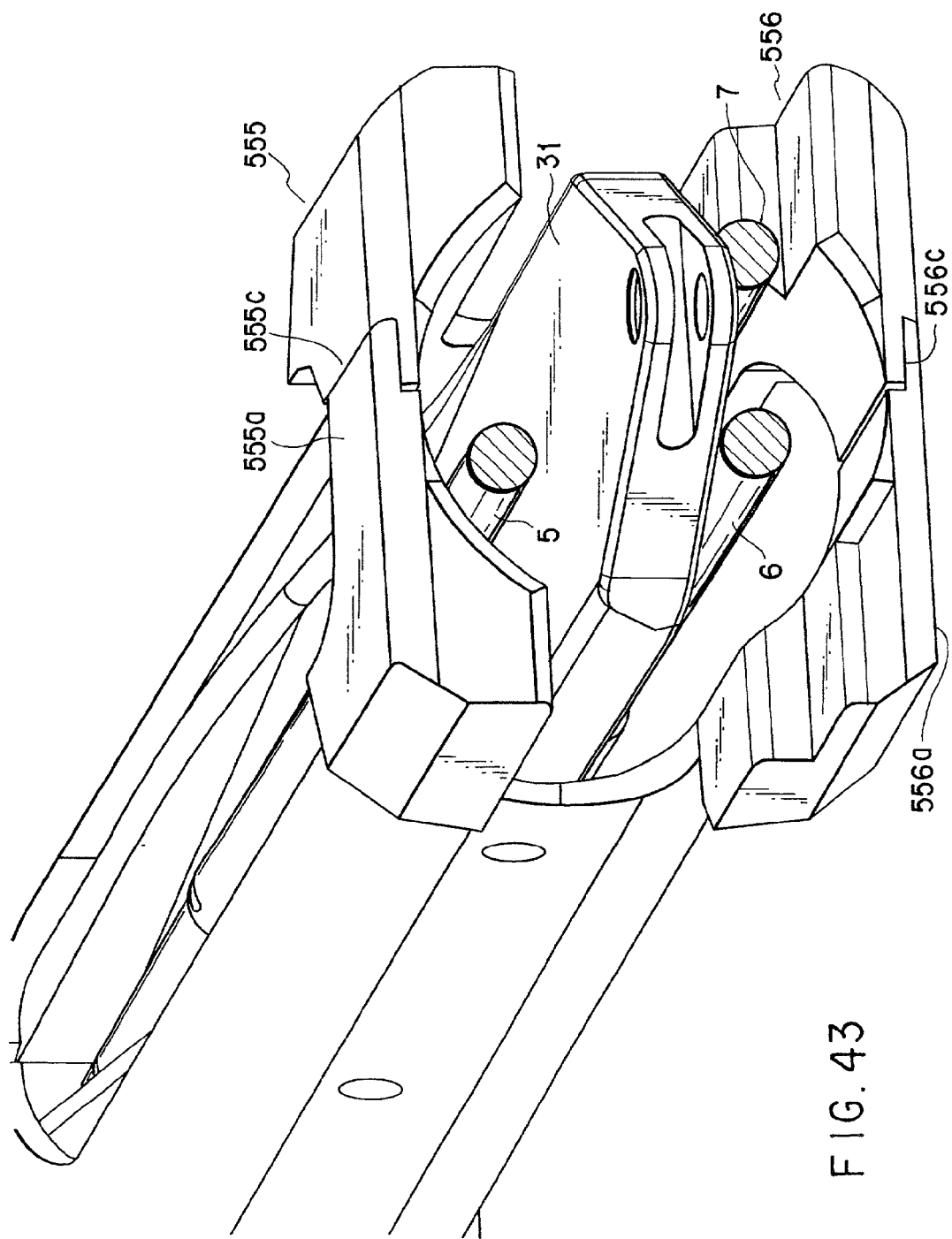
FIG. 43 is a perspective view showing a proximal end section of an insert section of the surgical instrument of FIG. 42.
Figure 44:
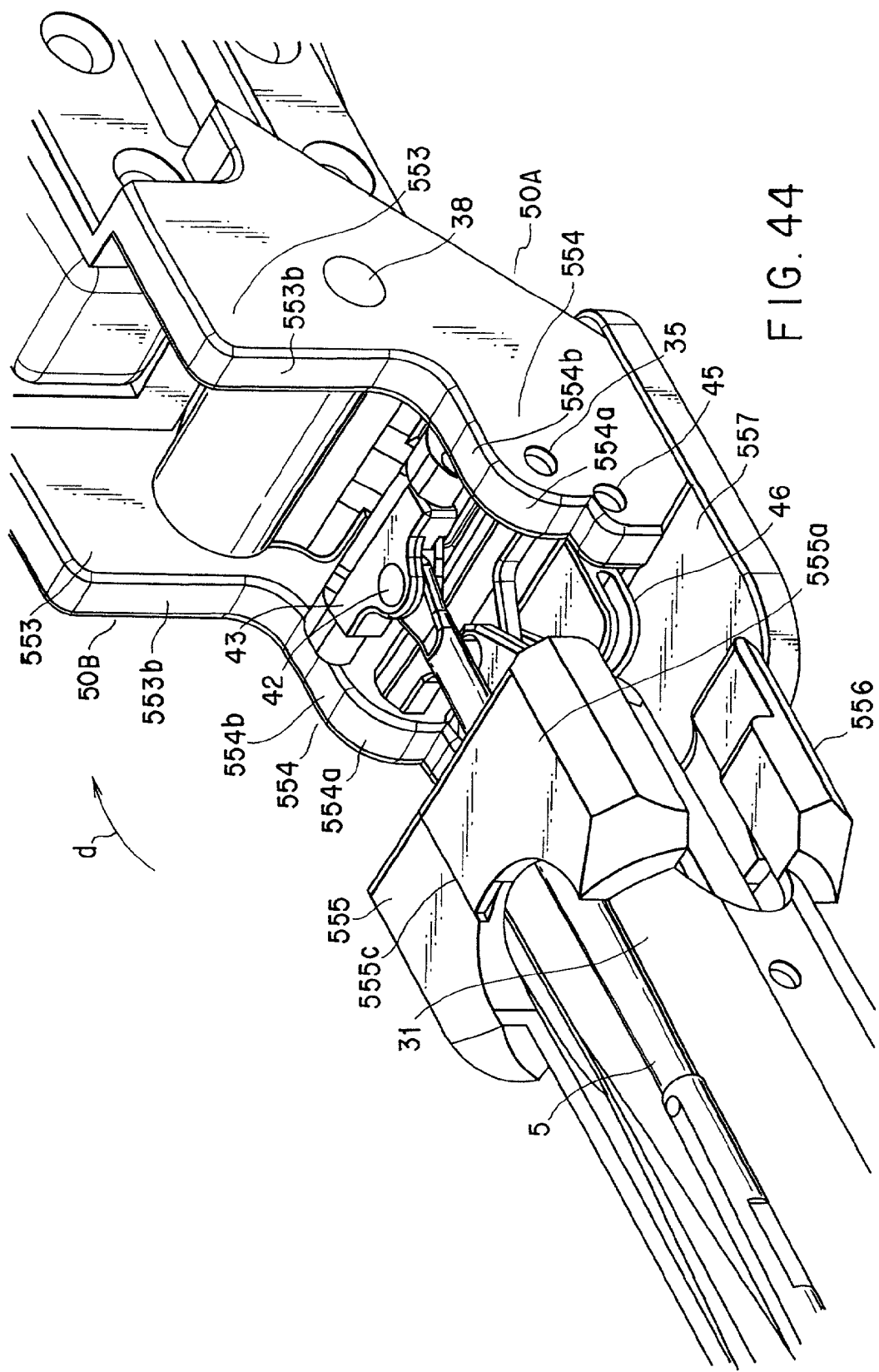
FIG. 44 is a perspective view showing the manipulating section of FIG. 42 while the articulating in the vertical direction is restricted.

FIG. 42 to FIG. 44 show an eleventh embodiment of the present invention. Like constituent elements identical to those of the tenth embodiment are designated by like reference numerals. A duplicate description is omitted here.

In the present embodiment, an upper guard housing 555 is removably and replaceably mounted at the upper part of the support section 31 provided at the proximal end section side of the insert section 2. A lower guard housing 556 is removably and replaceably mounted at the lower part of the support section 31. The upper guard housing 555 and lower guard housing 556 are identical to each other in structure, and abutment receiving faces 555a is formed on the upper face of the upper guard housing 555. Similarly, abutment receiving faces 556a is formed on the lower face of the lower guard housing 556. Further, the upper guard housing 555 and lower guard housing 556 are divided into two sections in a widthwise direction, and are engaged with stepped sections 555c and 556c at its center.

When the first handle 37 is articulated at a right angle relative to the axle of the insert section 2, a third cover member 557 orthogonal to the axle of the insert section 2 is provided at the first cover member 50A and the second cover member 50B. This third cover member 557 is formed by a rectangular flat plate, and the lower end section is protruded downwardly of a second protrusion portion 554 of the first cover member 50A and second cover member 50B.

According to the present embodiment, when the first and second handles 37 and 39 are articulated upwardly around the third pivot pin 35, a position vertical to the axle of the insert section 2 is defined as an articulation range. If the first and second handles 37 and 39 are further articulated in a direction indicated by the arrow "c" around the third pivot pin 35, as shown in FIG. 42, a lower face 553b of the first protrusion portion 553 of the first and second cover members 50A and 50B abuts against the abutment receiving face 555a of the upper guard housing 555. Therefore, even if an attempt is made to excessively turn the first and second handles 37 and 39 in the direction indicated by the arrow "c" over the limitation of their articulation, their articulation range is restricted.

When the first and second handles 37 and 39 are articulated downwardly around the third pivot pin 35, a position parallel to the axle of the insert section 2 is defined as an articulation range. If the first and second handles 37 and 39 are further articulated in a direction indicated by the arrow "d" around the third pivot pin 35, as shown in FIG. 44, a third cover member 557 abuts against an abutment receiving face 556a of the lower guard housing 556. Therefore, even if an attempt is made to mistakenly articulate the first and second handles 37 and 39 excessively in the direction indicated by the arrow "d", their articulation range is restricted.

Therefore, where the first and second handles 37 and 39 at the manipulating section 4 are articulated in a vertical direction around the third pivot pin 35, thereby placing the tool section 3 straight in the extension direction of the insert section 2, or alternatively, even if the first and second handles 37 and 39 are moved in excess of the articulation range when an angle is provided relative to the insert section 2, the first and second cover members 5A and 50B and the upper and lower guard housings 555 and 556 are cooperated, and the articulation range is restricted. Thus, damage of the manipulating section 4 can be prevented. In addition, the upper guard housing 555 and the lower guard housing 556 are removably/replaceably mounted on the support section 31, whereby these housings can be washed after removed, and can be easily replaced with the replacement housings if they are damaged.

Figure 45:
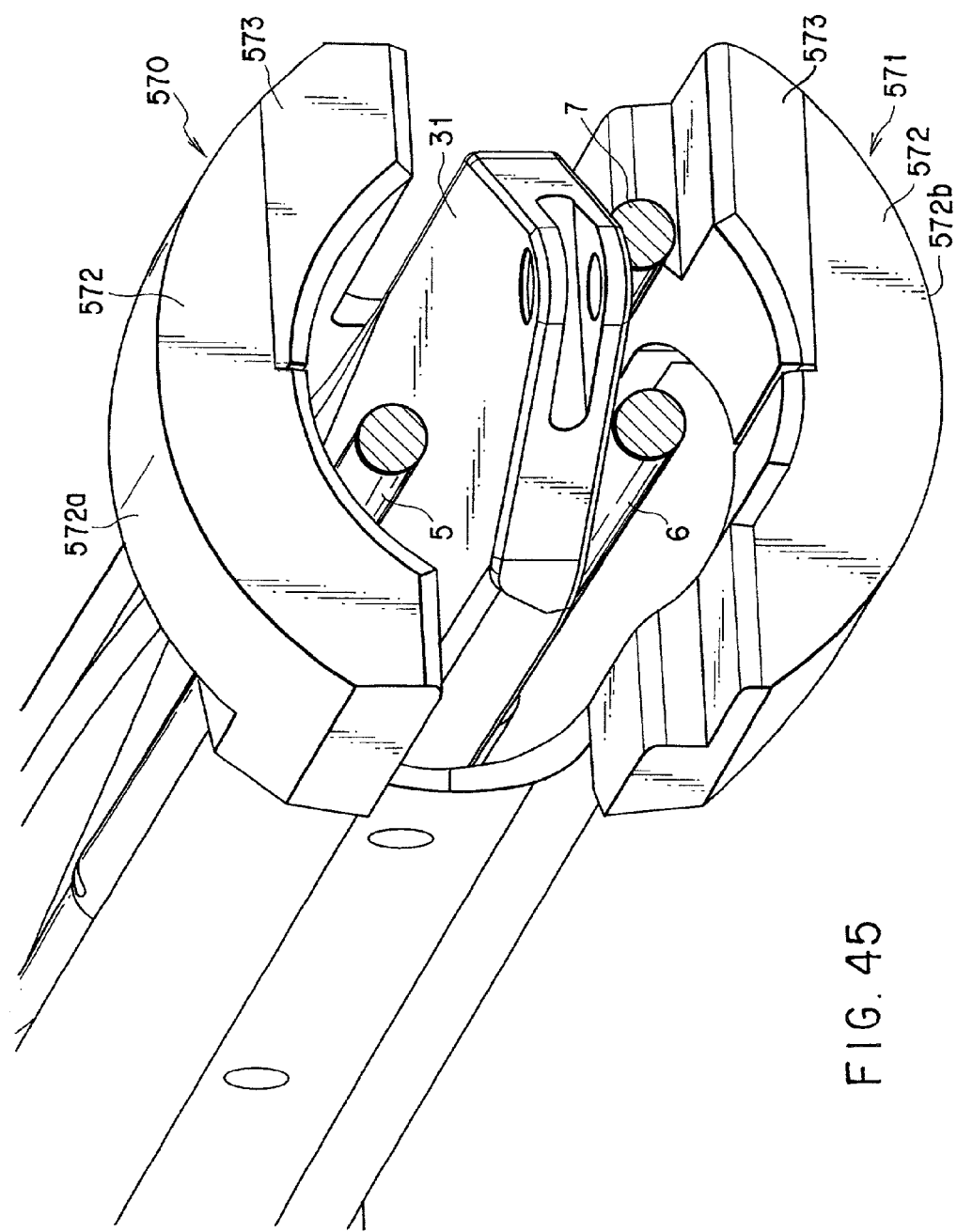
FIG. 45 is a perspective view showing a proximal end section of an insert section of a surgical instrument according to a twelfth embodiment of the present invention.

FIG. 45 shows a twelfth embodiment of the present invention. Constituent elements identical to those of the tenth and eleventh embodiments are designated by like reference numerals. A duplicate description is omitted here.

In the present embodiment, an upper guard housing 570 is removably mounted at the upper part of the support section 31 provided at the proximal end section side of the insert section 2. A lower guard housing 571 is removably mounted on the lower part of the support section 31. The upper guard housing 570 and the lower guard housing 571 are identical to each other in structure. The upper guard housing 570 and the lower guard housing 571 are divided in a widthwise direction into two sections, i.e., a first member 572 having on its upper face an arc shaped upper abutment receiving face 572a and lower abutment receiving face 572b which are high at the center and is gradually lowered toward both ends; and a second member 573 for engaging with and supporting this first member 572.

According to the present embodiment, if the first and the second handles 37 and 39 are articulated upwardly around the third pivot pin 35 and the first and the second handles 37 and 39 are turned transversely around the second pivot pin 32, upper abutment receiving face 572a of the guard housing 570 and the lower face 553b of the first protrusion portion 553 shown in FIG. 40 abut to each other. Thus, an articulation restriction range in vertical direction changes in dependence upon articulation transversely of the first and the second handles 37 and 39. Here, if desired, the first protrusion portion 553 of the first handle 37 is provided with a protrusion (not shown) abutting on upper abutment receiving face 572a at the intermediate portion of the two lower faces 553b and 553b.

Alternatively, if the first and the second handles 37 and 39 are articulated downwardly around the third pivot pin 35 and the first and the second handles 37 and 39 are articulated transversely around the second pivot pin 32, lower abutment receiving face 572b of the guard housing 570 and the third cover 557 shown in FIG. 42 abut to each other. Thus, a turn restriction range in vertical direction changes in dependence upon articulating transversely of the first and the second handles 37 and 39. Here, if desired, the third cover isn't flat plate and the intermediate portion of the third cover is provided with a protrusion (not shown) abutting on lower abutment receiving face 572b.

Therefore, according to the present embodiment, the articulation range in the vertical direction is restricted according to an articulation angle at which the first and second handles 37 and 39 are articulated transversely around the second pivot pin 32. Namely, when the articulation angle in the transverse direction of the first and second handles 37 and 39 is large relative to the axle of the insert section 2, the articulation range in the vertical direction is significantly admitted while restricting. As the articulation angle in the transverse direction decreases, the articulation range in the vertical direction is admitted to be small while restricting.

Conversely, when the articulation angle in the transverse direction is large relative to the axle of the insert section 2, the articulation range in the vertical direction is admitted to be small while restricting. As the articulation angle in the transverse direction increases, the articulation range in the vertical direction is significantly admitted while restricting.

Figure 46:
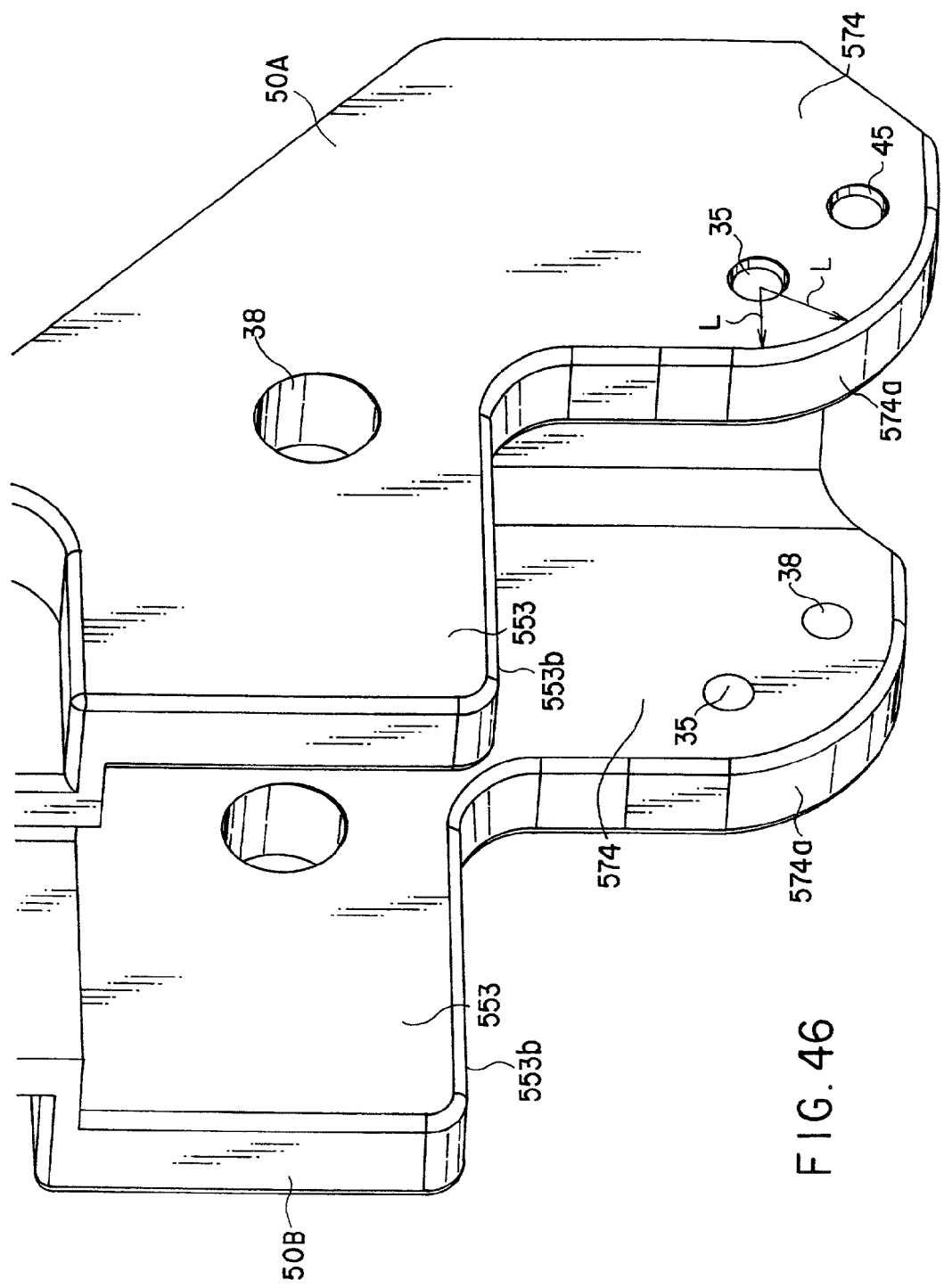
FIG. 46 is a perspective view showing a cover member of a surgical instrument according to a thirteenth embodiment of the present invention.

FIG. 46 shows a thirteenth embodiment of the present invention. Like constituent elements identical to those of the tenth to twelfth embodiments are designated by like reference numerals. A duplicate description is omitted here.

In the present embodiment, the first and second cover members 50A and 50B has a second protrusion portion 574 that protrudes downwardly of the second opening/closing pivot pin 38 and that has an arc shaped section 574a. The arc shaped section 574a is formed to have a curvature such that a distance L from the center of the third pivot pin 35 gradually increases downwardly. Therefore, the articulation range in the transverse direction is restricted according to an articulation angle at which the first and second handles 37 and 39 are articulated vertically around the third pivot pin 35. Namely, when the articulation angle in the vertical direction of the first and second handles 37 and 39 is large relative to the axle of the insert section 2, the articulation range in the transverse direction is significantly admitted while restricting. As the articulation angle in the vertical direction decreases, the articulation range in the transverse direction is admitted to be small while restricting.

Conversely, when the articulation angle in the vertical direction is large relative to the axle of the insert section 2, the articulation range in the transverse direction is admitted to be small while restricting. As the articulation angle in the vertical direction decreases, the articulation range in the transverse direction is significantly admitted while restricting.

FIG. 47 to FIG. 50 show a fourteenth embodiment of the present invention. Like constituent elements identical to those of the tenth to thirteenth embodiments are designated by like reference numerals. A duplicate description is omitted here.

Figure 47:
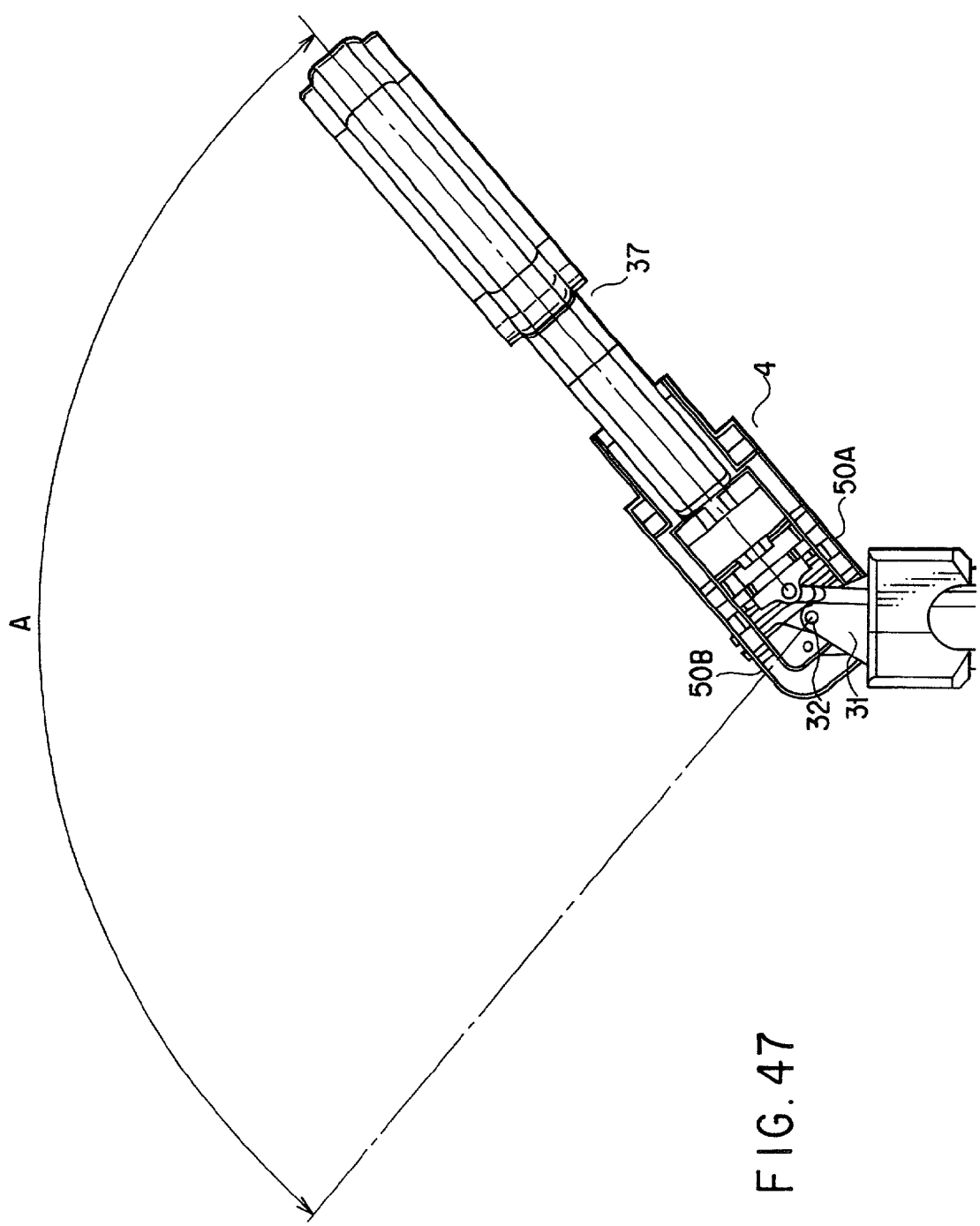
FIG. 47 is a plan view showing a manipulating section according to a fourteenth embodiment of the present invention when the manipulating section placed in parallel to an axle of an insert section is articulated in a transverse direction.
Figure 48:
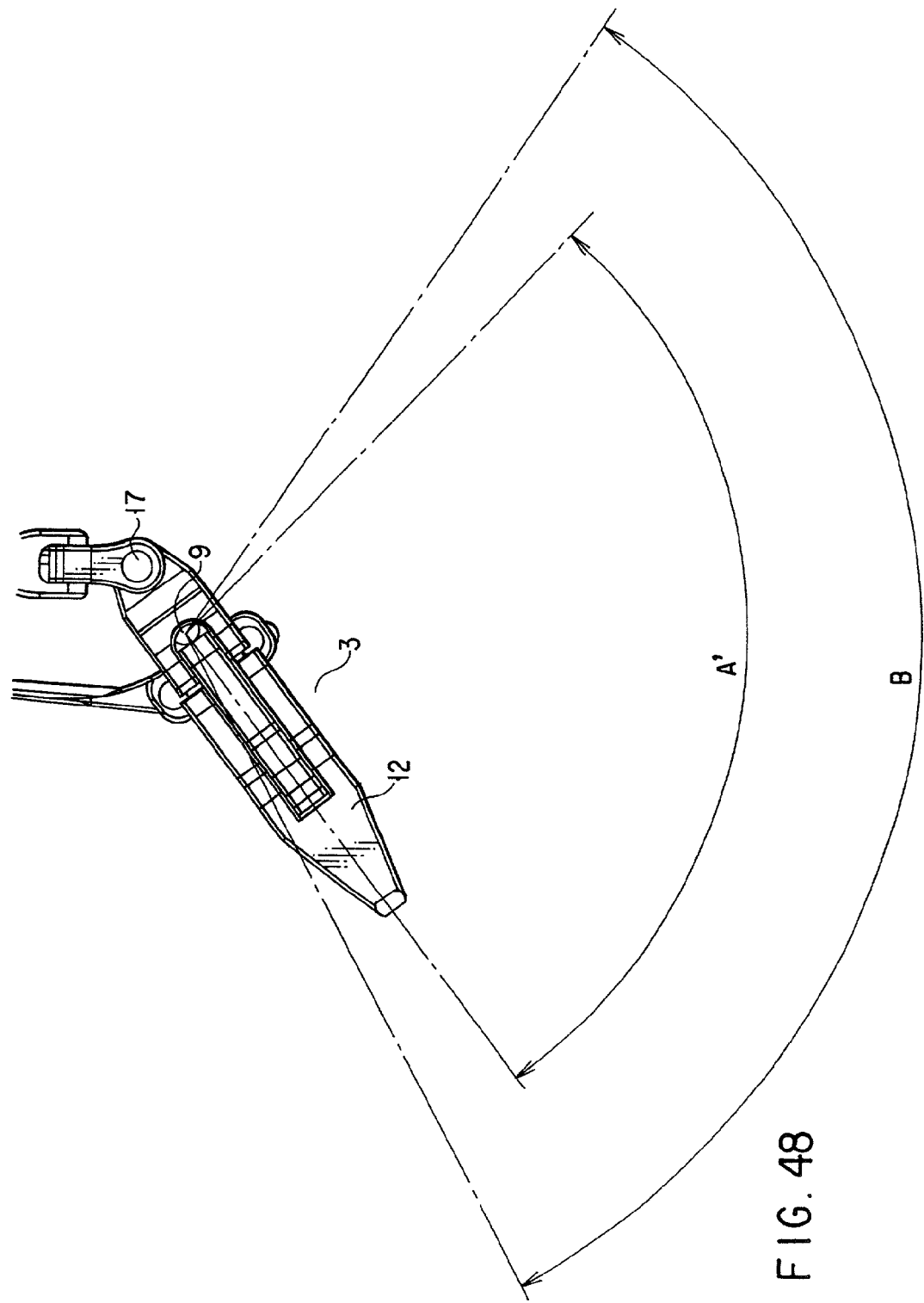
FIG. 48 is a plan view showing a tool section when the manipulating section according to the fourteenth embodiment of the present invention is articulated in the transverse direction.

FIG. 47 is a plan view showing a manipulating section 4 when the first and second handles 37 and 39 placed in parallel to the axle of the insert section 2 are articulated in a transverse direction around the second pivot shaft 32. FIG. 48 is a plan view showing a tool sections when the manipulating section 4 is articulated to be in the state shown in FIG. 47.

As in the tenth embodiment, an articulating movement range A in the transverse direction of the manipulating section 4 is set by the first and second cover members 50A and 50B and the abutment receiving face 31a of the support section 31. This articulating movement range A of the manipulating section 4 is restricted to be an articulating movement range A' that is smaller than an articulating movement enabling range B in which the tool section 3 is articulated in the transverse direction around the first pivot shaft 9. In this way, the articulating movement range A of the manipulating section 4 is restricted to be the articulating movement range A' that is smaller than the articulating movement enabling range B of the tool section 3, whereby it is prevented that the excessive load is applied to the tool section 3 due to the turning and dimensional errors of parts and assembling errors can be offset, and movement of the manipulated section 4 can be reliably transmitted to the tool section 3.

Figure 49:
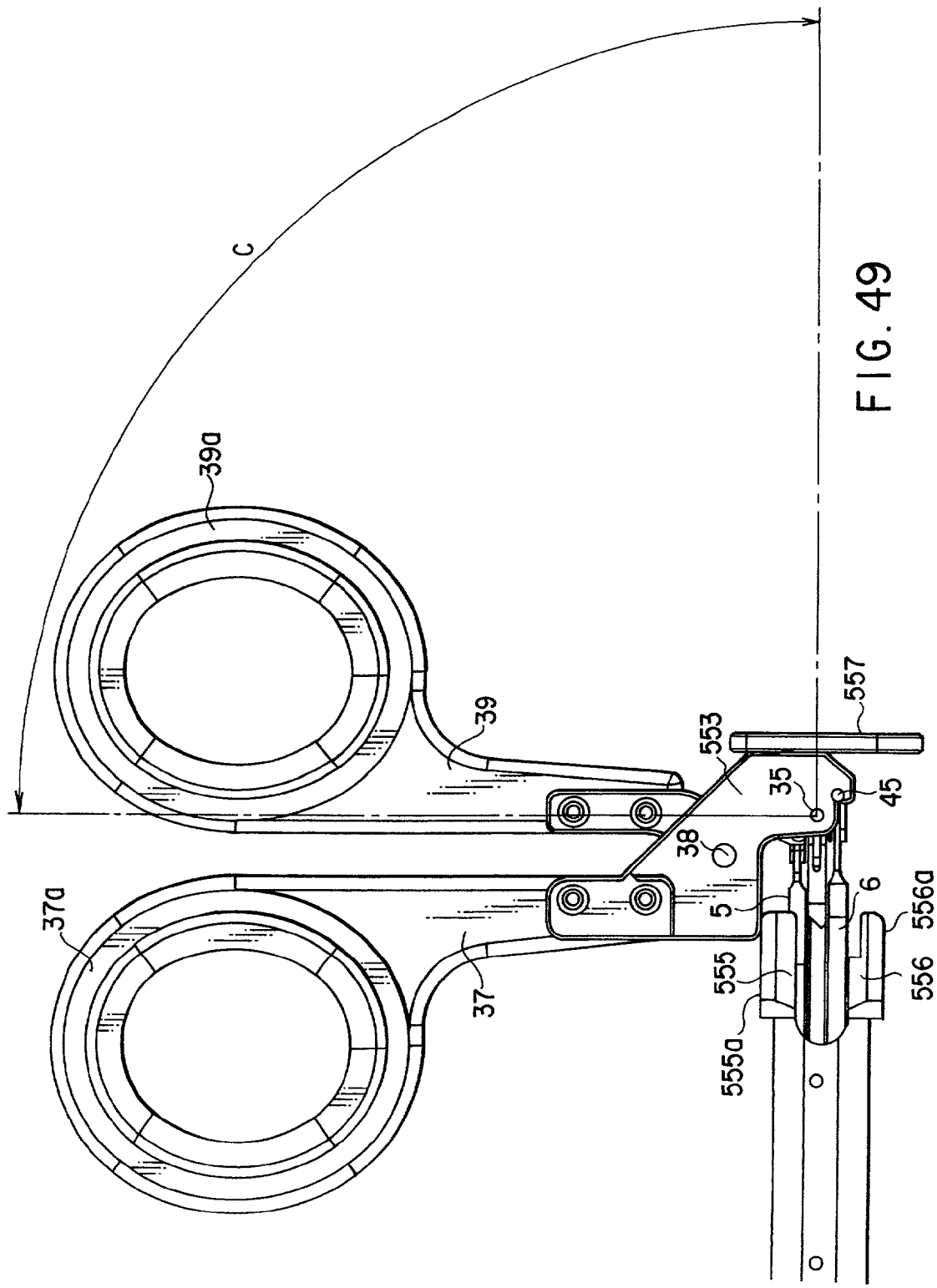
FIG. 49 is a side view showing the manipulating section according to the fourteenth embodiment of the present invention when the manipulating section is placed in parallel to the axle of the insert section.
Figure 50:
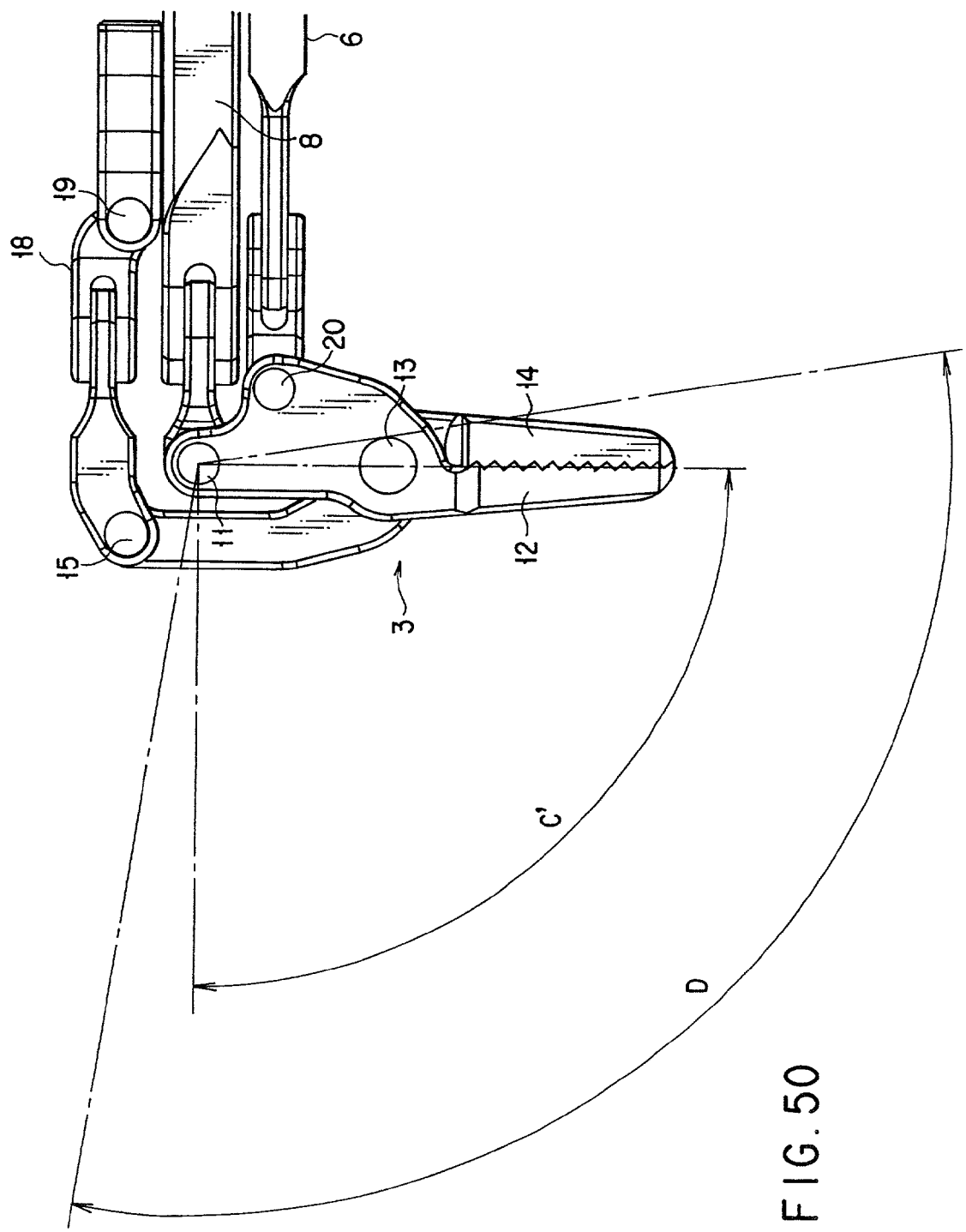
FIG. 50 is a side view showing the tool section according to the fourteenth embodiment of the present invention when the manipulating section is articulated in a vertical direction.

FIG. 49 is a side view showing a manipulating section 4 when the first and second handles 37 and 39 placed in parallel to the axle of the insert section 2 are articulated at a right angle around the third pivot pin 35. FIG. 50 is a side view showing a tool section 3 when the manipulating section 4 is articulated in a vertical direction.

As in the eleventh embodiment, an articulating movement range C in the vertical direction of the manipulating section 4 is set by the first and second cover members 50A and 50B and the abutment receiving faces 555a and 556a of the upper guard housing 555 and lower guard housing 556 provided at the support section 31. This articulating movement range C of the manipulating section 4 is restricted to be an articulating movement range C' that is smaller than an articulating movement enabling range D in which the tool section 3 is articulated in the vertical direction around the first pivot pin 11. In this way, the articulating movement range C of the manipulating section 4 is restricted to be the articulating movement range C' that is smaller than the articulating movement enabling range D of the tool section 3, whereby it is prevented that the excessive load is applied to the tool section 3 due to the turning and dimensional errors of parts and assembling errors can be offset, and movement of the manipulating section 4 can be reliably transmitted to the tool section 3.

As has been described above, according to the tenth to fourteenth embodiments, the articulation range of the manipulating section is restricted, whereby an excessive load can be prevented. As a result, durability can be improved.

Figure 51:
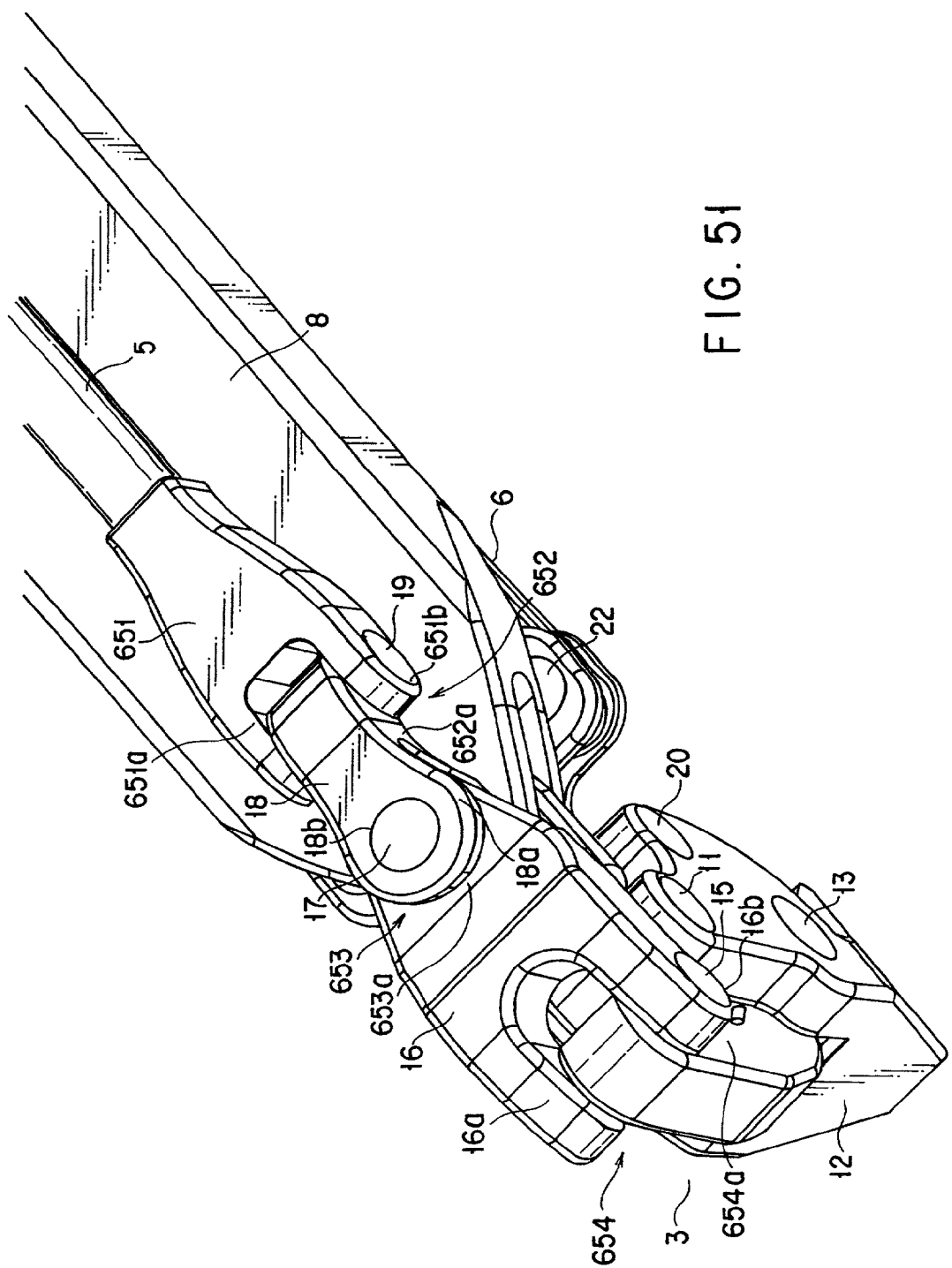
FIG. 51 is a perspective view showing a tool section of a surgical instrument according to a fifteenth embodiment of the present invention.
Figure 52:
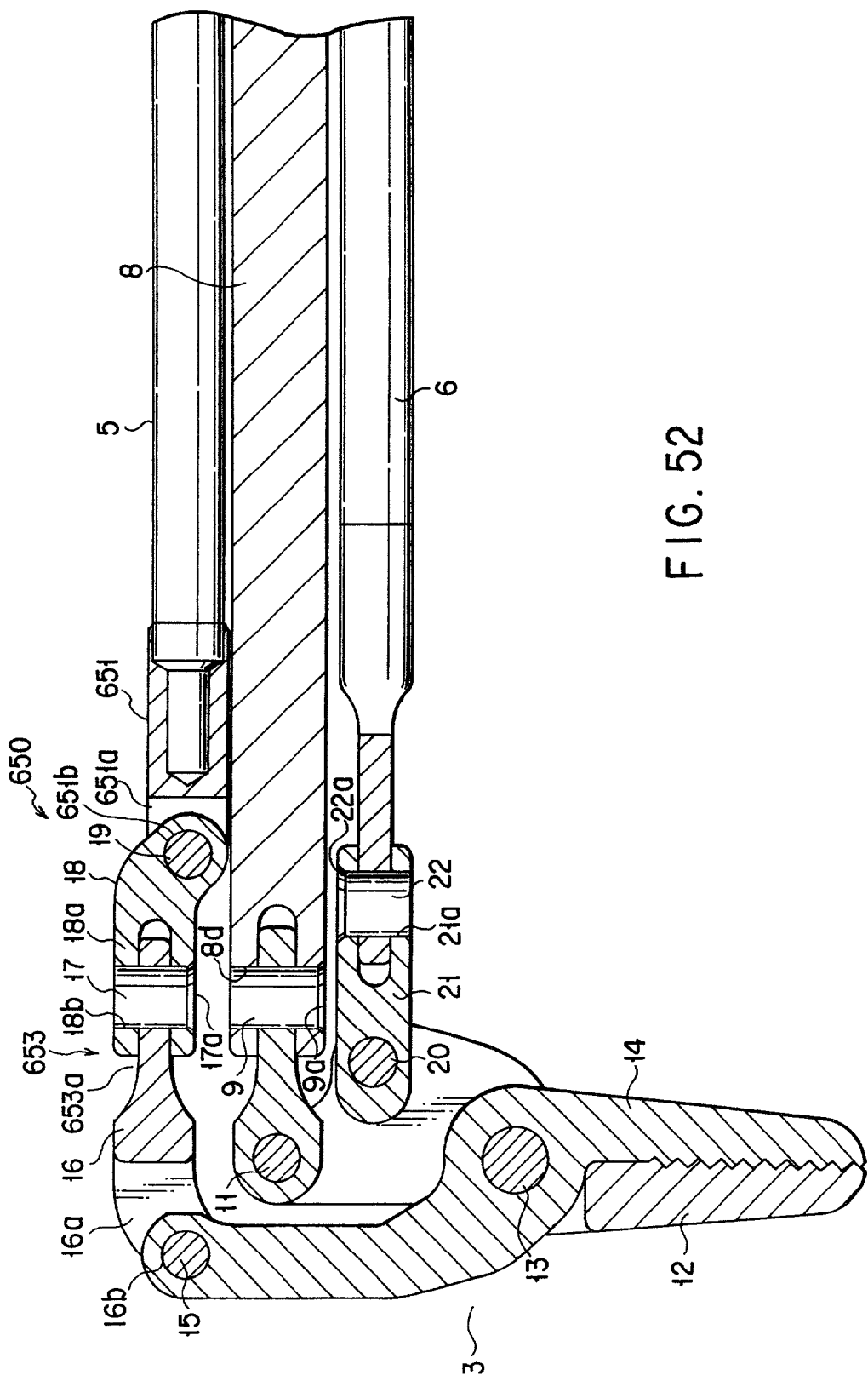
FIG. 52 is a longitudinal side view showing the tool section of the surgical instrument of FIG. 51.
Figure 53:
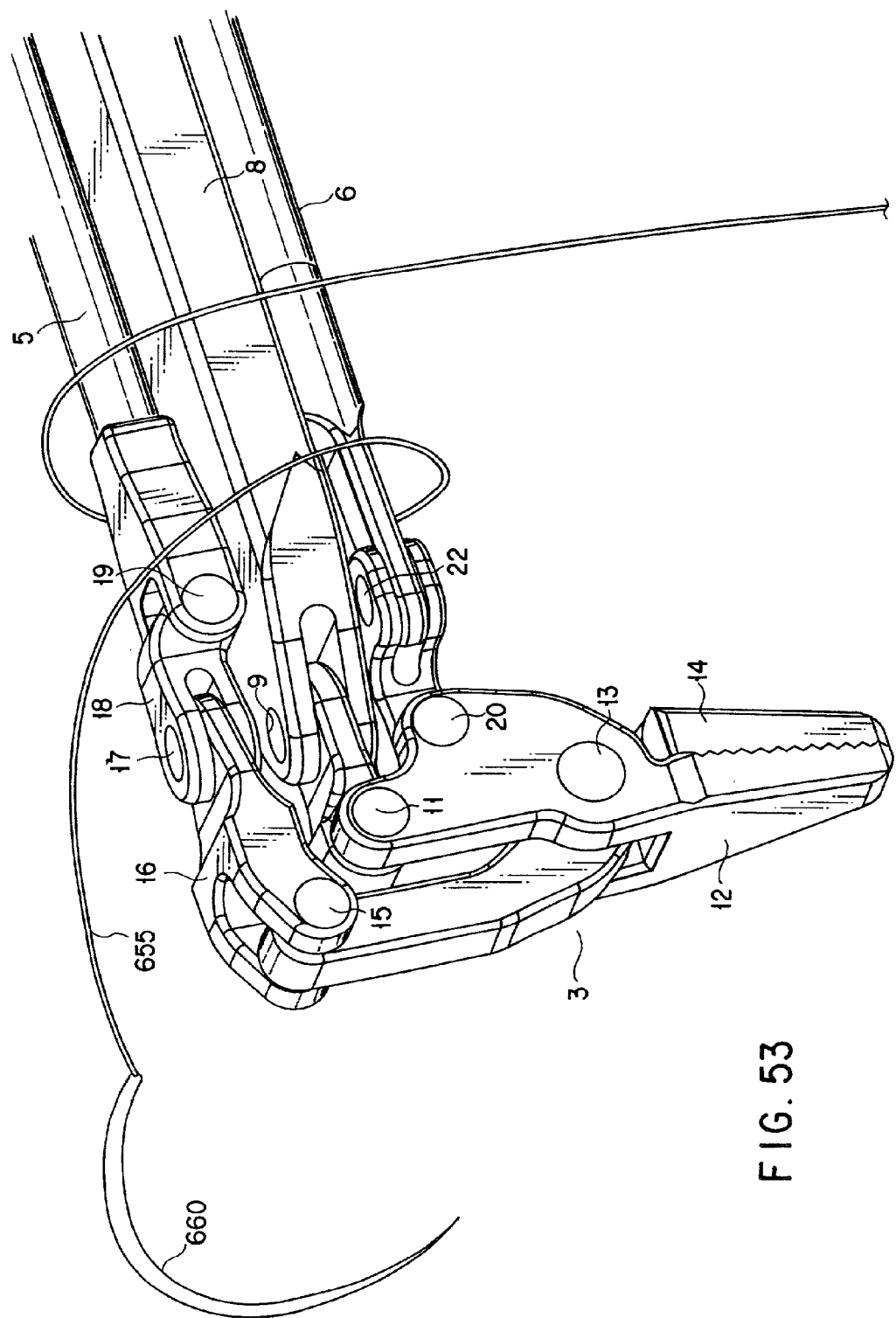
FIG. 53 is a perspective view showing the tool section, for illustrating working of the surgical instrument of FIG. 51.

FIG. 51 to FIG. 53 show a fifteenth embodiment of the present invention. In the present embodiment, like constituent elements common to those of the previously-described embodiments each are designated by like reference numerals. A duplicate description thereof is omitted here.

As shown in FIG. 51 and FIG. 52, in the present embodiment, improvement has been applied to a portion provided at the distal end section of the insert section 2 and transmitting movement of the manipulating section 4 to the tool section 3 (hereinafter, referred to transmitting means 650). Specifically, the proximal end section of a connecting member 651 serving as a transmitting member is fixed to the distal end section of the first drive rod 5. The connecting member 651 is formed to be gradually broader toward its distal end. At its distal end section, a two-way section 651a is formed in a planar view.

A pin hole 651b pivoting the third connecting pin 19 is provided at the two-way section 651a of the connecting member 651 to be pierced in the transverse direction. Further, the proximal end section of the second connecting member 18 serving as a transmitting member is pivoted at the third connecting pin 19 turnably in the vertical direction. This second connecting member 18 as well is formed to be gradually wider toward its distal end. At its distal end section a two-way section 18a is formed in a side view.

A pin hole 18a pivoting the second connecting pin 17 is provided at the two-way section 18a of the second connecting member 18 to be pierced in the vertical direction. Further, the proximal end section of the first connecting member 16 serving as a transmitting member is pivoted turnably in the transverse direction at the second connecting member 18. This first connecting member 16 as well is formed gradually wider toward its distal end. At its distal end section, a two-way section 16a is formed in a planar view.

A pin hole 16b pivoting the first connecting pin 15 is provided at the two-way section 16a of the first connecting member 16 to be pieced in the transverse direction. Further, the proximal end section of the second tool piece 14 is pivoted at the first connecting member 16 turnably in the vertical direction.

Therefore, a first step 652 is formed in the transverse direction at a connecting portion between the connecting member 651 and the second connecting member 18. A second step 653 is formed in the vertical direction at a connecting portion between the second connecting member 18 and the first connecting member 16. A third step 654 is formed in the transverse direction at a connecting portion between the first connecting member 16 and the second tool piece 14. At the first step 652, second step 653 and third step 654, their low step sites 652a, 653a, and 654a are closer to the axle of the insert section 2 than a site that is located at the distal end side of the insert section 2 and tool section 3 and that is high in step.

Therefore, when tissues are sutured by the surgical instrument, as shown in FIG. 53, there has been arised an operation step in which the suturing is effected while the suture thread 655 extending from the suture needle 660 is wound around the insert section 2. However, the transmitting means 650 is formed at a step that is lowered toward the distal end of the insert section 2. Thus, there is an advantageous effect that the intermediate portion of the suture thread 655 is not hooked on the step, and the suture thread 655 can be released smoothly from the insert section 2.

As shown in FIG. 52, the second connecting pin 17 has a divergent section 17a at one end close to the axis of the insert section 2, and is inserted from downward into the pin hole 18b. The first pivot shaft 9 has a divergent section 9a at one end close to the axis of the insert section 2, and is inserted from downward into a split 8a. In addition, the first pin 22 and the second pin 23 have divergent sections 22a and 23a (only one of which is shown) at one end close to the axis of the insert section 2, and are inserted from upward into the pin hole 21a of the second turn plate 21.

With such a construction, even if a pin fixing means (not shown) such as thread, welding, caulking, and adhesion is faulted, the divergent section 17a does not slip off upwardly, and the slip-off direction is limited to its downward direction. However, after the tool section 3 has been assembled, the support section 8 approaches downwardly of the pivot pin 17, and thus, the pivot pin 17 does not slip off.

The pivot pin 9 does not slip off upwardly by the presence of the divergent section 9a, and the slip-off direction is limited to its downward direction. After the tool section 3 has been assembled, the second turn plate 21 approaches downwardly of the pivot pin 9, and thus, the pivot pin 9 does not slip off. Similarly, the first and second turn pins 22 and 23 do not slip of downwardly by the presence of the divergent sections 22a and 23a, and the slip-off direction is limited to its upward direction. However, after the tool section 3 has been assembled, the support section 8 approaches upwardly of the first and second turn pins 22 and 23, and thus, the first and second turn pins 22 and 23 do not slip off.

What is claimed is:

1. A surgical instrument comprising:
    an insert section inserted into a patient's body;
    a tool section which is provided at a distal end of the insert section, which has first and second tool pieces connected to each other by a first opening/closing pivot pin and opened/closed by being turned relative to each other around the first opening/closing pivot pin, and which is capable of being articulated around at least one first articulating pivot pin orthogonal to a longitudinal center axis of the insert section;
    a manipulating section which is provided at a proximal end of the insert section, which has first and second manipulating bodies connected to each other by a second opening/closing pivot pin and opened/closed by being turned relative to each other around the second opening/closing pivot pin, and which is capable of being articulated around at least one second articulating pivot pin orthogonal to the longitudinal center axis of the insert section;
    an articulating link mechanism which connects the first manipulating body and the first tool piece to each other and causes the first tool piece to be articulated around the first articulating pivot pin due to articulating of the first manipulating body around the second articulating pivot pin; and
    an opening/closing link mechanism which connects the second manipulating body and the second tool piece to each other and causes the second tool piece to be turned around the first opening/closing pivot pin due to turning of the second manipulating body around the second opening/closing pivot pin,
    wherein the first opening/closing pivot pin is positioned at a first side relative to a longitudinal center axis of the insert section, the second opening/closing pivot pin is positioned at a second side relative to a longitudinal center axis of the insert section, and the first side and the second side form a substantially symmetrical position relationship to each other relative to the longitudinal center axis of the insert section,
    the articulating link mechanism and the opening/closing link mechanism comprising a total of at least three drive rods, and wherein a distance between a first pivot pin for turnably connecting the second manipulating body and the opening/closing link mechanism to each other and the second opening/closing pivot pin is defined to be equal to a distance between a second pivot pin for turnably connecting the second tool piece and the opening/closing link mechanism with each other and the first opening/closing pivot pin.

2. A surgical instrument according to claim 1, wherein the articulating link mechanism comprises at least two drive rods.

3. A surgical instrument according to claim 2, wherein the opening/closing link mechanism comprises at least one drive rod.

* * * * *